US011639505B2

(12) United States Patent
Cuero Rengifo

(10) Patent No.: US 11,639,505 B2
(45) Date of Patent: May 2, 2023

(54) UV-RESISTANT BIOLOGICAL DEVICES AND EXTRACTS AND METHODS FOR PRODUCING AND USING THE SAME

(71) Applicant: Bio Capital Holdings, LLC, Houston, TX (US)

(72) Inventor: Raul Cuero Rengifo, Cypress, TX (US)

(73) Assignee: Bio Capital Holdings, LLC, Houston, TX (US)

( * ) Notice: Subject to any disclaimer, the term of this patent is extended or adjusted under 35 U.S.C. 154(b) by 568 days.

(21) Appl. No.: 16/686,326

(22) Filed: Nov. 18, 2019

(65) Prior Publication Data

US 2020/0080093 A1 Mar. 12, 2020

Related U.S. Application Data

(63) Continuation-in-part of application No. PCT/US2018/033090, filed on May 17, 2018.

(60) Provisional application No. 62/557,217, filed on Sep. 12, 2017, provisional application No. 62/507,946, filed on May 18, 2017.

(51) Int. Cl.
| | |
|---|---|
| C12N 15/00 | (2006.01) |
| C12N 15/64 | (2006.01) |
| C12N 9/04 | (2006.01) |
| C12N 9/12 | (2006.01) |

(52) U.S. Cl.
CPC ........... *C12N 15/64* (2013.01); *C12N 9/0006* (2013.01); *C12N 9/1205* (2013.01); *C12N 2800/10* (2013.01)

(58) Field of Classification Search
CPC ............ C12Q 2600/158; C12Q 1/6886; C12Q 2600/156; C12N 15/09; C12N 15/63; C12N 2310/20; C12N 9/1205
USPC .................... 435/91.1, 252.3, 6, 14; 536/23.2
See application file for complete search history.

(56) References Cited

U.S. PATENT DOCUMENTS

2014/0170087 A1 6/2014 Cuero et al.
2016/0168578 A1 6/2016 Cuero Rengifo et al.

FOREIGN PATENT DOCUMENTS

WO 2013004607 1/2013

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
International Search Report and Written Opinion for PCT/US18/33090 dated Nov. 27, 2018 (22pp).
Chen, Z. et al., "Enhanced Expression of Transferrin Receptor Confers UV-resistance in Human and Monkey Cells," 2005, J. Radiat. Res., 46:443-451.
Veroan, A.M. et al., "Iron binding of 3-hydroxychromone, 5-hydroxychromone, and sulfated morin: Implications for the antioxidant activity of flavonols with competing metal binding sites," 2011, J. Inorg. Biochem., 105:1314-1322.
GenBank Submission YSCHXKA. Yeast (*S. cerevisiae*) hexokinase PI (HXK1) gene, complete coding sequence, 1993, <http://www.ncbi.nlm.nih.gov/nucoore/171736> accessed Aug. 5, 2018 (2 pp).
GenBank Submission X13713, Yeast SSB1 heat shock cognate gene, 2005, <http://www.ncbi.nlm.nih.gov/nuccore/X13713> accessed Aug. 5, 2018 (2 pp).
GenBank Submission YSCADH2, *Saccharomyces cerevisiae* alcohol dehydrogenase II gene, complete coding sequence, 2004, <http://www.ncbi.nim.nih.gov/nuccore/171020> accessed Aug. 6, 2018 (2pp).
Curran, K.A. et al., "Use of High Capacity Terminators in *Saccharomyces cerevisiae* to Increase mRNA half-life and Improve Gene Expression Control for Metabolic Engineering Applications," 2013, Metab. Eng., 19:38-97.
Kanchanapoom, K. et al., "The Effect of chitosan on the Organogenesis of Oil Palm Embryo-Derived Callus," 2010, Not. Bot. Hort. Agrobot. Cluj, 2010, 38:213-217.
Biogard,Technical Data Sheet, "Chitosan 6," 2017, <http://rumexo.com/downloads/agriculture/Chitosan_TDS.pdf> accessed Aug. 5, 2018 (4 pp).
Rasmussen, K. et al., "Barnacle Settlement on Hydrogels," 2002, Biofouling: J. of Bioadhesion and Biofilm Res., 18:5 pp.
Koev, S.T. et al., "Chitosan: an integrative biomaterial for lab-on-a-chip devices," 2010, Lab on a Chip, 10:3026-3042.
GenBank Submission U84259.1, *Arabidopsis thaliana* cultivar Columbia flavonol synthase mRNA, complete coding sequence, 1998, <htts://www.ncbi.nlm.nih.gov/nuccore/U84259.1/>, retrieved Oct. 17, 2018 (2 pp).

(Continued)

*Primary Examiner* — Robert B Mondesi
*Assistant Examiner* — Mohammad Y Meah
(74) *Attorney, Agent, or Firm* — Thomas | Horstemeyer, LLP

(57) ABSTRACT

Described herein are UV-resistant or UV-protective biological devices and extracts produced therefrom. The biological devices include microbial cells transformed with a DNA construct containing genes for producing UV-resistant proteins such as, for example, hexokinase, heat shock proteins, alcohol dehydrogenase, transferrin, flavonol synthase, zinc oxidase, and iron oxidase. Methods for producing and using the devices are also described herein. Finally, compositions and methods for using the devices and extracts to reduce or prevent UV-induced damage or exposure to materials, items, plants, and human and animal subjects are described herein.

19 Claims, 6 Drawing Sheets

Specification includes a Sequence Listing.

(56) References Cited

OTHER PUBLICATIONS

GenBank Submission CP002985.1, Acidithiobacillus ferrivorans SS3 complete genome, 2011, <https://www.ncbi.nlm.nih.gov/nuccore/CP002985.1/>, retrieved Oct. 17, 2018 (313 pp).

GenBank Submission CP016438.1, Streptomyces lincolnensis strain NRRL 2935, complete genome, 2016, <https:/ncbi.nlm.nih.gov/nuccore/CP016438>, retrieved Oct. 17, 2018 (1649 pp).

Sathya, M. et al., "Growth of pure and doped ZnO thin films for solar cell applications," 2012, Adv. Appl. Sci. Res., 3:2591-2598.

Helfrecht, B., "Zinc Oxide Based Ultraviolet Solar Cells for Self-Powered Smart Window Application," 2013, <http://www.nnin.org/sites/default/files/2013_reu_ra/2013nninRA_Helfrecht.pct>, accessed Oct. 17, 2018 (2 pp).

* cited by examiner

UV-RESISTANT BIOLOGICAL DEVICES AND EXTRACTS AND METHODS FOR PRODUCING AND USING THE SAME

CROSS REFERENCE TO RELATED APPLICATIONS

This application in a continuation-in-part of international application no. PCT/US2018/033090 filed on May 17, 2018, which claims priority upon U.S. provisional application Ser. No. 62/507,946 filed on May 18, 2017 and 62/557,217 filed Sep. 12, 2017. These applications are hereby incorporated by reference in their entirety.

CROSS REFERENCE TO SEQUENCE LISTING

The genetic components described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

BACKGROUND

Exposure to UV radiation causes harmful effects in a wide variety of things, both living and non-living. For example, exposure of human skin to UV radiation can cause severe sunburn and skin cancer and exposure of beneficial microorganisms to UV radiation can kill them. UV radiation can also cause materials to degrade prematurely and thus suffer mechanical failure or otherwise become unable to serve their intended purpose.

The harmful effects of UV radiation can generally be prevented or lessened through the simple step of using a compound or composition to absorb all or a portion of the UV radiation before it reaches the item it may harm. For example, chemicals in sunscreen absorb a portion of the UV radiation that would normally reach the skin and, as a result, help protect the skin from sunburn and skin cancer.

Although numerous substances capable of absorbing UV radiation are known, not all of them are suitable for all possible uses. Further, some substances may be expensive to produce or may have harmful side effects, such as toxicity or undesired chemical reactions with a protected material. Other substances simply do not last long enough in the environment in which they are used, or persist long after their period of usefulness.

Accordingly, there is a demand for new substances able to absorb UV radiation, particularly if those substances are biocompatible. The present invention addresses this demand.

SUMMARY

Described herein are UV-resistant or UV-protective biological devices and extracts produced therefrom. The biological devices include microbial cells transformed with a DNA construct containing genes for producing UV-resistant proteins such as, for example, hexokinase, heat shock proteins, alcohol dehydrogenase, transferrin, flavonol synthase, zinc oxidase, and iron oxidase. Methods for producing and using the devices are also described herein. Finally, compositions and methods for using the devices and extracts to reduce or prevent UV-induced damage or exposure to materials, items, plants, and human and animal subjects are described herein.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1A:
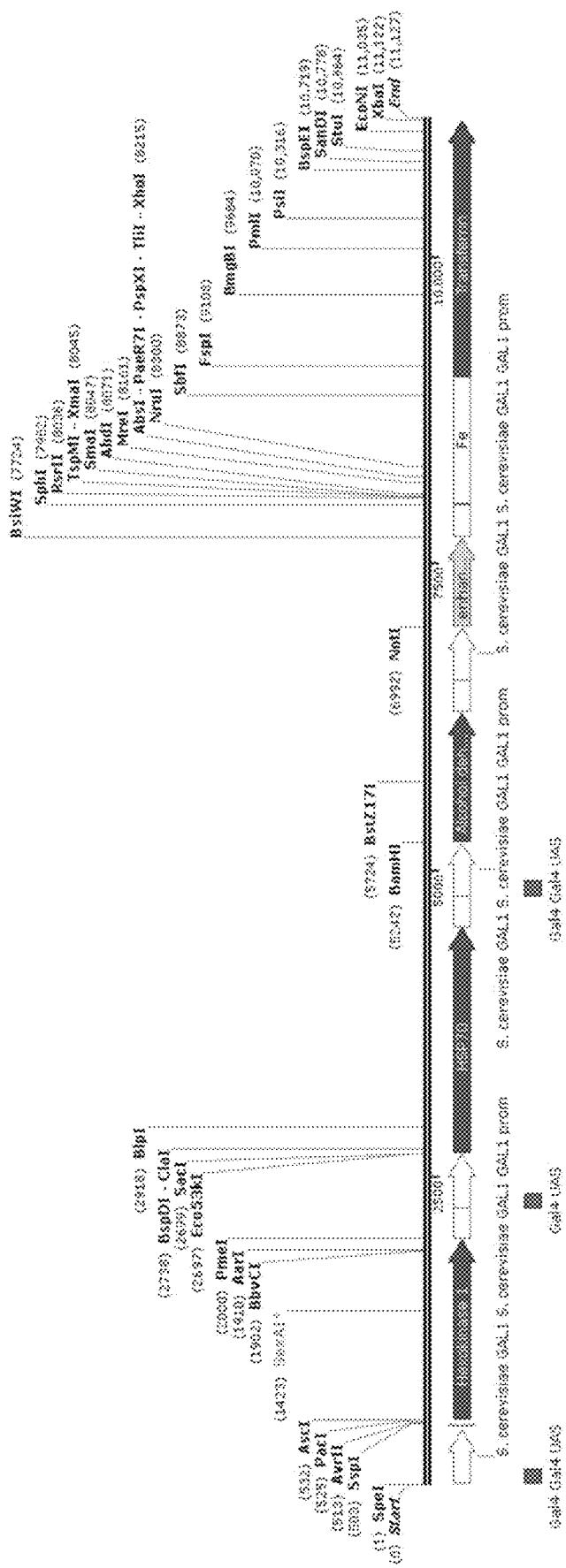
FIGS. 1A and 1B shows, respectively, a linear and circular schematic of a constructed pYES2 plasmid showing the direction, placement, and size of genetic parts used in one aspect of an exemplary DNA device described herein.

Before the present compounds, compositions, articles, devices, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "an isolated nucleic acid" includes mixtures of two or more such nucleic acids, and the like.

"Optional" or "optionally" means that the subsequently described event or circumstance can or cannot occur, and that the description includes instances where the event or circumstance occurs and instances where it does not. For example, the phrase "optionally includes a gene for a selective marker" means that the gene may or may not be present.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the endpoints of each of the ranges are significant both in relation to the other endpoint, and independently of the other endpoint.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc. of these materials are disclosed, that while specific reference of each various individual and collective combination and permutation of these compounds may not be explicitly disclosed, each is specifically contemplated and described herein. For example, if a bacterium is disclosed and discussed and a number of different compatible bacterial plasmids are discussed, each and every combination and permutation of bacterium and bacterial plasmid that is possible is specifically contemplated unless specifically indicated to the contrary. For example, if a class of molecules A, B, and C are disclosed as well as a class of molecules D, E, and F, and an example of a combination molecule, A-D, is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if a variety of additional steps can be performed, it is understood that each of these additional steps can be performed with any specific embodiment or combination of embodiments of the disclosed methods, and that each such combination is specifically contemplated and should be considered disclosed.

References in the specification and concluding claims to parts by weight of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

"Heterologous" genes and proteins are genes and proteins that have been experimentally put into a cell that are not normally expressed by that cell. A heterologous gene may be cloned or derived from a different cell type or species than the recipient cell or organism. Heterologous genes may be introduced into cells by transduction or transformation.

An "isolated" nucleic acid is one that has been separated from other nucleic acid molecules and/or cellular material (peptides, proteins, lipids, saccharides, and the like) normally present in the natural source of the nucleic acid. An "isolated" nucleic acid may optionally be free of the flanking sequences found on either side of the nucleic acid as it naturally occurs. An isolated nucleic acid can be naturally occurring, can be chemically synthesized, or can be a cDNA molecule (i.e., is synthesized from an mRNA template using reverse transcriptase and DNA polymerase enzymes.

"Transformation" or "transfection" as used herein refers to a process for introducing heterologous DNA into a host cell. Transformation can occur under natural conditions or may be induced using various methods known in the art. Many methods for transformation are known in the art and the skilled practitioner will know how to choose the best transformation method based on the types of cells being transformed. Methods for transformation include, for example, viral infection, electroporation, lipofection, chemical transformation, and particle bombardment. Cells may be stably transformed (i.e., the heterologous DNA is capable of replicating as an autonomous plasmid or as part of the host chromosome) or may be transiently transformed (i.e., the heterologous DNA is expressed only for a limited period of time).

"Competent cells" refers to microbial cells capable of taking up heterologous DNA. Competent cells can be purchased from a commercial source, or cells may be made competent using procedures known in the art. Exemplary procedures for producing competent cells are provided in the Examples.

DNA Constructs and Biological Devices

The biological devices described herein can be used to produce UV-protective proteins, extracts, and other components. The devices are generally composed of host cells, where the host cells are transformed with a DNA construct described herein that promotes the expression of proteins involved in UV resistance responses.

It is understood that one way to define the variants and derivatives of the genetic components and DNA constructs described herein is through defining the variants and derivatives in terms of homology/identity to specific known sequences. Those of skill in the art readily understand how to determine the homology of two nucleic acids. For example, the homology can be calculated after aligning two sequences so that the homology is at its highest level. Another way of calculating homology can be performed by published algorithms (see Zuker, M., 1989 *Science*, 244:48-52; Jaeger et al., 1989, *Proc. Natl. Acad. Sci. USA*, 86:7706-7710; Jaeger et al., 1989, *Methods Enzymol.*, 183:281-306, which are herein incorporated by reference for at least material related to nucleic acid alignment.)

As used herein, "conservative" mutations are mutations that result in an amino acid change in the protein produced from a sequence of DNA. When a conservative mutation occurs, the new amino acid has similar properties as the wild type amino acid and generally does not drastically change the function or folding of the protein (e.g., switching isoleucine for valine is a conservative mutation since both are small, branched, hydrophobic amino acids). "Silent mutations," meanwhile, change the nucleic acid sequence of a gene encoding a protein but do not change the amino acid sequence of the protein.

It is understood that the description of conservative mutations an homology can be combine together in any combination, such as embodiments that have at least 70%, 75%, 80%, 85%, 90%, 95%, or 99% homology to a particular sequence wherein the variants are conservative mutations. It is understood that any of the sequences described herein can be a variant or derivative having the homology values listed above. In one aspect, the separate elements of the DNA constructs disclosed herein have at least 90% homology with the sequences disclosed herein. In another aspect, the separate elements have at least 95% homology or at least 99% homology with the sequences disclosed herein.

In one aspect, a database such as, for example, GenBank, can be used to determine the sequences of genes and/or regulatory regions of interest, the species from which these elements originate, and relate homologous sequences.

In one aspect, the DNA construct comprises the following genetic components: (a) a gene that expresses hexokinase, (b) a gene that expresses a heat shock protein, (c) a gene that expresses alcohol dehydrogenase, and (d) a gene that expresses transferrin.

In another aspect, the DNA construct comprises the following genetic components: (a) a gene that expresses zinc oxidase or a gene that expresses flavonol synthase, (b) a gene that expresses hexokinase, (c) a gene that expresses a heat shock protein, (d) a gene that expresses alcohol dehydrogenase, and (e) a gene that expresses iron oxidase.

In one aspect, the DNA construct described herein can promote the expression of UV-resistant proteins. In one aspect, the DNA construct is, from 5' to 3', the following genetic components in the following order: (a) a gene that expresses hexokinase, (b) a gene that expresses a heat shock protein, (c) a gene that expresses alcohol dehydrogenase, and (d) a gene that expresses transferrin.

In still another aspect, the DNA construct is, from 5' to 3', the following genetic components in the following order: (a) a gene that expresses flavonol synthase, (b) a gene that expresses hexokinase, (c) a gene that expresses a heat shock protein, (d) a gene that expresses alcohol dehydrogenase, and (e) a gene that expresses iron oxidase.

In still another aspect, the DNA construct is, from 5' to 3', the following genetic components in the following order: (a) a gene that expresses zinc oxidase, (b) a gene that expresses hexokinase, (c) a gene that expresses a heat shock protein, (d) a gene that expresses alcohol dehydrogenase, and (e) a gene that expresses iron oxidase.

In one aspect, a regulatory sequence is already incorporated into a vector such as, for example, a plasmid, prior to genetic manipulation of the vector. In another aspect, the regulatory sequence can be incorporated into the vector through the use of restriction enzymes or any other technique known in the art.

In one aspect, the regulatory sequence is a promoter. The term "promoter" refers to a DNA sequence capable of controlling the expression of a coding sequence. In one aspect, the coding sequence to be controlled is located 3' to the promoter. In another aspect, the promoter is derived from a native gene. In an alternative aspect, the promoter is composed of multiple elements derived from different genes and/or promoters. A promoter can be assembled from elements found in nature, from artificial and/or synthetic elements, or from a combination thereof. It is understood by those skilled in the art that different promoters can direct the expression of a gene in different tissues or cell types, at different stages of development, in response to different environmental or physiological conditions, and/or in different species. In one aspect, the promoter functions as a switch to activate the expression of a gene.

In one aspect, the promoter is "constitutive." A constitutive promoter is a promoter that causes a gene to be expressed in most cell types at most times. In another aspect, the promoter is "regulated." A regulated promoter is a promoter that becomes active in response to a specific stimulus. A promoter may be regulated chemically, for example, in response to the presence of a particular metabolite (e.g., lactose or tryptophan), a metal ion, a molecule secreted by a pathogen, or the like. A promoter may also be regulated physically, for example, in response to heat, cold, water stress, salt stress, oxygen concentration, illumination (including UV exposure), wounding, or the like.

Promoters that are useful to drive expression of the nucleotide sequences described herein are numerous and familiar to those skilled in the art. Suitable promoters include, but are not limited to, the following: T3 promoter, T7 promoter, iron promoter, and GAL1 promoter. Variants of these promoters are also contemplated. In one aspect, the promoter is a GAL1 promoter. In another aspect, several promoters, either the same or different, can appear in the same device. The skilled artisan will be able to use site-directed mutagenesis and/or other mutagenesis techniques to modify the promoters to promote more efficient function. The promoter can be positioned, for example, from 10-100 nucleotides away from a ribosomal binding site. In one aspect, the promoter is positioned before the gene that expresses hexokinase, heat shock protein, alcohol dehydrogenase, transferrin, flavonol synthase, iron oxidase, zinc oxidase, or any combination thereof.

In one aspect, the promoter is a GAL1 promoter. In another aspect, the GAL1 promoter is native to the plasmid used to create the vector. In another aspect, a GAL1 promoter is positioned before the gene that expresses hexokinase, heat shock protein, alcohol dehydrogenase, flavonol synthase, and zinc oxidase. In another aspect, the promoter is a GAL1 promoter obtained from or native to the pYES2 plasmid. In another aspect, an iron promoter is positioned before the gene that expresses transferrin and iron oxidase.

In another aspect, the regulatory sequence is a terminator or stop sequence. As used herein, a terminator is a sequence of DNA that marks the end of a gene or operon to be transcribed. In a further aspect, the terminator is an intrinsic terminator or a Rho-dependent transcription terminator. As used herein, an "intrinsic terminator" is a sequence wherein a hairpin structure can form in the nascent transcript and wherein the hairpin disrupts the mRNA/DNA/RNA polymerase complex. As used herein, a "Rho-dependent" transcription terminator requires a Rho factor protein complex to disrupt the mRNA/DNA/RNA polymerase complex. In one aspect, the terminator is a CYC1 terminator. In still another aspect, multiple terminators can be included in the same DNA construct.

In a further aspect, the regulatory sequence includes both a promoter and a terminator or stop sequence. In a still further aspect, the regulatory sequence can include multiple promoters or terminators. Other regulatory elements, such as enhancers, are also contemplated. Enhancers may be located from about 1 to about 2,000 nucleotides in the 5' direction from the start codon of the DNA to be transcribed, or may be located 3' to the DNA to be transcribed. Enhancers may be "cis-acting," that is, located on the same molecule of DNA as the gene whose expression they affect.

In certain aspects, the DNA construct can include a gene that expresses a reporter protein. The selection of the reporter protein can vary. For example, the reporter protein can be a yellow fluorescent protein, a red fluorescent protein, a green fluorescent protein, or a cyan fluorescent protein. The amount of fluorescence that is produced by the biological device can be correlated to the amount of DNA incorporated into the host cells. The fluorescence produced by the device can be detected and quantified using techniques known in the art. For example, spectrofluorometers are typically used to measure fluorescence.

In one aspect, the DNA construct is, from 5' to 3', the following genetic components in the following order: (1) a gene that expresses hexokinase having SEQ ID NO. 4 or at least 70% homology thereto, (2) a gene that expresses a heat shock protein having SEQ ID NO. 5 or at least 70% homology thereto, (3) a gene that expresses alcohol dehydrogenase having SEQ ID NO. 6 or at least 70% homology thereto, (4) an iron promoter having SEQ ID NO. 7 or at least 70% homology thereto, and (5) a gene that expresses transferrin having SEQ ID NO. 8 or at least 70% homology thereto.

In another aspect, the DNA construct is, from 5' to 3', the following genetic components in the following order: (1) a gene that expresses flavonol synthase having SEQ ID NO. 9 or at least 70% homology thereto, (2) a gene that expresses hexokinase having SEQ ID NO. 4 or at least 70% homology thereto, (3) a gene that expresses a heat shock protein having SEQ ID NO. 5 or at least 70% homology thereto, (4) a gene that expresses alcohol dehydrogenase having SEQ ID NO. 6 or at least 70% homology thereto, (5) an iron promoter having SEQ ID NO. 7 or at least 70% homology thereto, and (6) a gene that expresses iron oxidase having SEQ ID NO. 10 or at least 70% homology thereto.

In another aspect, the DNA construct is, from 5' to 3', the following genetic components in the following order: (1) a gene that expresses zinc oxidase having SEQ ID NO. 11 or at least 70% homology thereto, (2) a gene that expresses hexokinase having SEQ ID NO. 4 or at least 70% homology thereto, (3) a gene that expresses a heat shock protein having SEQ ID NO. 5 or at least 70% homology thereto, (4) a gene that expresses alcohol dehydrogenase having SEQ ID NO. 6 or at least 70% homology thereto, (5) an iron promoter having SEQ ID NO. 7 or at least 70% homology thereto, and (6) a gene that expresses fl having SEQ ID NO. 10 or at least 70% homology thereto.

In another aspect, the DNA construct is, from 5' to 3', the following genetic components in the following order: (1) a GAL1 promoter, (2) a gene that expresses hexokinase having SEQ ID NO. 4 or at least 70% homology thereto, (3) a CYC1 terminator, (4) a GAL1 promoter, (5) a gene that expresses a heat shock protein having SEQ ID NO. 5 or at least 70% homology thereto, (6) a CYC1 terminator, (7) a GAL1 promoter, (8) a gene that expresses alcohol dehydrogenase having SEQ ID NO. 6 or at least 70% homology thereto, (9) a CYC1 terminator, (10) a GAL1 promoter, (11) a yellow fluorescent reporter protein having SEQ ID NO. 12 or at least 70% homology thereto, (12) a CYC1 terminator, (13) an iron promoter having SEQ ID NO. 7 or at least 70% homology thereto, and (14) a gene that expresses transferrin having SEQ ID NO. 8 or at least 70% homology thereto (FIG. 1). In another aspect, the DNA construct is SEQ ID NO. 1.

Figure 2A:
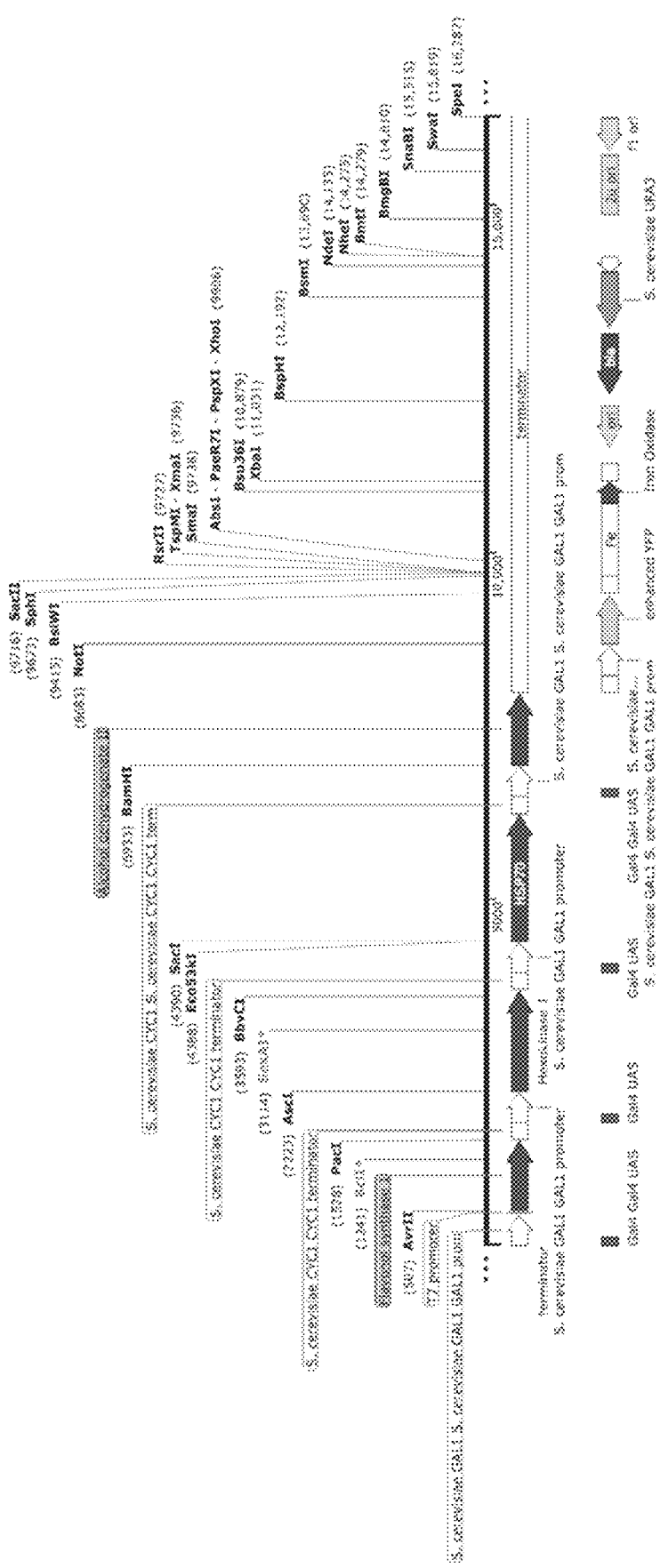
FIGS. 2A and 2B shows, respectively, a linear and circular schematic of a constructed pYES2 plasmid showing the direction, placement, and size of genetic parts used of an exemplary DNA device described herein.
Figure 2B:
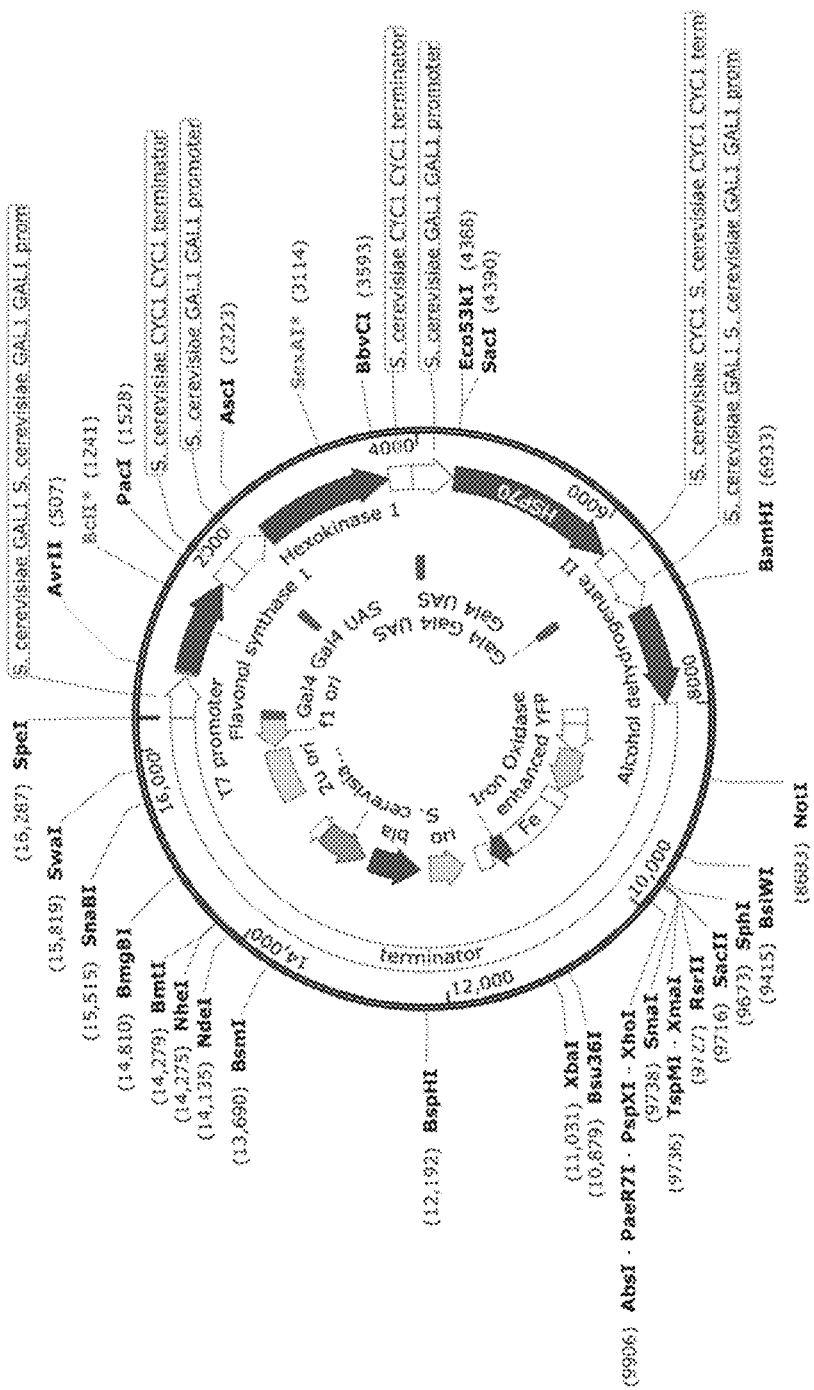

In another aspect, the DNA construct is, from 5' to 3', the following genetic components in the following order: (1) a GAL1 promoter, (2) a gene that expresses flavonol synthase having SEQ ID NO. 9 or at least 70% homology thereto, (3) a CYC1 terminator, (4) a GAL1 promoter, (5) a gene that expresses hexokinase having SEQ ID NO. 4 or at least 70% homology thereto, (6) a CYC1 terminator, (7) a GAL1 promoter, (8) a gene that expresses a heat shock protein having SEQ ID NO. 5 or at least 70% homology thereto, (9) a CYC1 terminator, (10) a GALL promoter, (11) a gene that expresses alcohol dehydrogenase having SEQ ID NO. 6 or at least 70% homology thereto, (12) a CYC1 terminator, (13) a GAL1 promoter, (14) a yellow fluorescent reporter protein having SEQ ID NO. 12 or at least 70% homology thereto, (15) a CYC1 terminator, (16) an iron promoter having SEQ ID NO. 7 or at least 70% homology thereto, and (17) a gene that expresses iron oxidase having SEQ ID NO. 10 or at least 70% homology thereto (FIG. 2). In another aspect, the DNA construct is SEQ ID NO. 2.

Figure 3A:
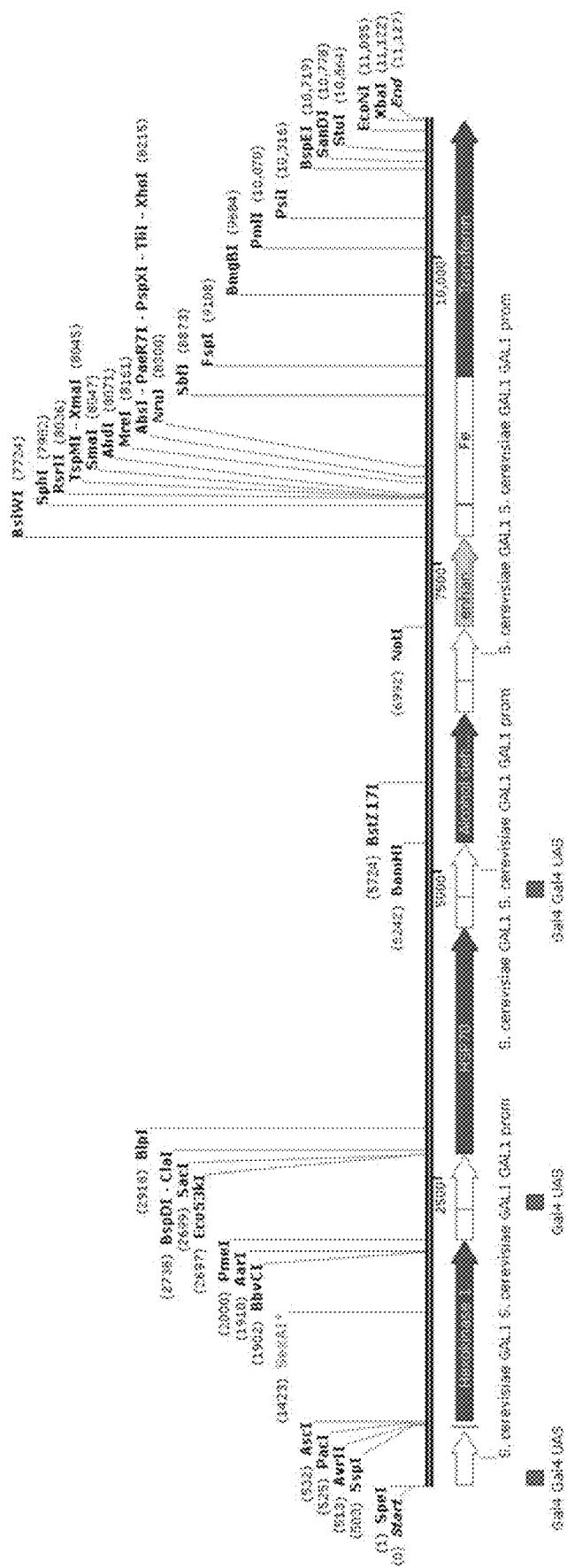
FIGS. 3A and 3B shows, respectively, a linear and circular schematic of a constructed pYES2 plasmid showing the direction, placement, and size of genetic parts used of an exemplary DNA device described herein.
Figure 3B:
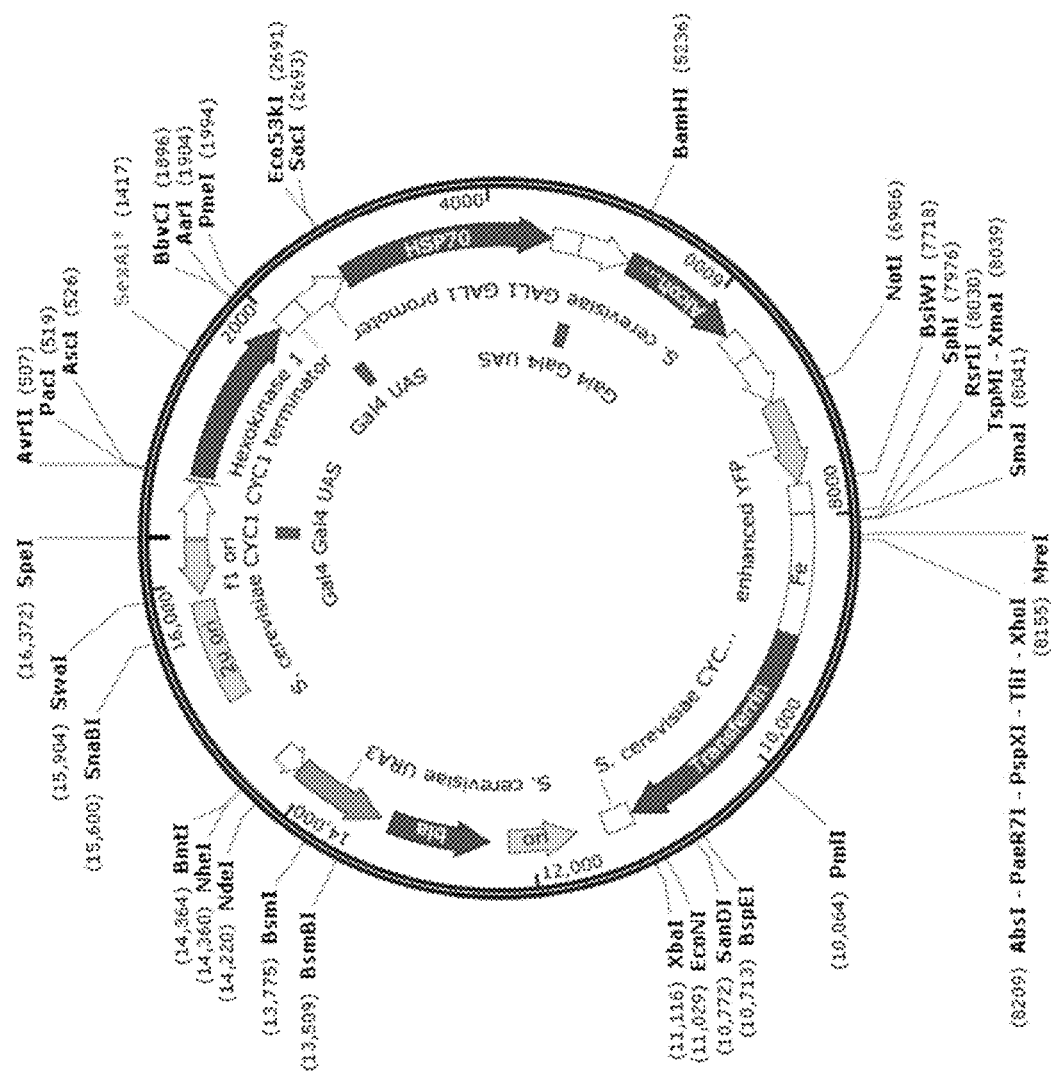

In another aspect, the DNA construct is, from 5' to 3', the following genetic components in the following order: (1) a GAL1 promoter, (2) a gene that expresses zinc oxidase having SEQ ID NO. 11 or at least 70% homology thereto, (3) a CYC1 terminator, (4) a GAL1 promoter, (5) a gene that expresses hexokinase having SEQ ID NO. 4 or at least 70% homology thereto, (6) a CYC1 terminator, (7) a GAL1 promoter, (8) a gene that expresses a heat shock protein having SEQ ID NO. 5 or at least 70% homology thereto, (9) a CYC1 terminator, (10) a GAL1 promoter, (11) a gene that expresses alcohol dehydrogenase having SEQ ID NO. 6 or at least 70% homology thereto, (12) a CYC1 terminator, (13) a GAL1 promoter, (14) a yellow fluorescent reporter protein having SEQ ID NO. 12 or at least 70% homology thereto, (15) a CYC1 terminator, (16) an iron promoter having SEQ ID NO. 7 or at least 70% homology thereto, and (17) a gene that expresses iron oxidase having SEQ ID NO. 10 or at least 70% homology thereto (FIG. 3). In another aspect, the DNA construct is SEQ ID NO. 3.

The DNA construct described herein can be part of a vector. In one aspect, the vector is a plasmid, a phagemid, a cosmid, a yeast artificial chromosome, a bacterial artificial chromosome, a virus, a phage, or a transposon.

In general, plasmid vectors containing replicon and control sequences that are derived from species compatible with the host cell are used in connection with these hosts. Vectors capable of high levels of expression of recombinant genes and proteins are well known in the art. The vector ordinarily carries a replication origin as well as marking sequences that are capable of providing phenotypic selection in transformed cells. Plasmid vectors useful for the transformation of a variety of host cells are well known and are commercially available. Such vectors include, but are not limited to, pWLNEO, pSV2CAT, pOG44, pXT1, pSG (Stratagene), pSVK3, pBSK, pBR322, pYES, pYES2, pBSKII, and pUC vectors.

Plasmids are double-stranded, autonomously-replicating, genetic elements that are not integrated into host cell chromosomes. Further, these genetic elements are usually not part of the host cell's central metabolism. In bacteria, plasmids may range from 1 kilobase (kb) to over 200 kb. Plasmids can be engineered to encode a number of useful traits including the production of secondary metabolites, antibiotic resistance, the production of useful proteins, degradation of complex molecules and/or environmental toxins, and others. Plasmids have been the subject of much research in the field of genetic engineering, as plasmids are convenient expression vectors for foreign DNA in, for example, microorganisms. Plasmids generally contain regulatory elements such as promoters and terminators and also usually have independent replication origins. Ideally, plasmids will be present in multiple copies per host cell and will contain selectable markers (such as genes for antibiotic resistance) to allow the ordinarily skilled artisan to select host cells that have been successfully transfected with the plasmids (for example, by culturing the host cells in a medium containing the antibiotic).

In one aspect, the vector encodes a selection marker. In a further aspect, the selection marker is a gene that confers resistance to an antibiotic. In certain aspects, during fermentation of host cells transformed with the vector, the cells are contacted with the antibiotic. For example, the antibiotic may be included in the culture medium. Cells that have not been successfully transformed cannot survive in the presence of the antibiotic; only cells containing the vector that confers antibiotic resistance can survive. Optionally, only cells containing the vector to be expressed will be cultured, as this will result in the highest production efficiency of the desired gene products (e.g., proteins having a UV-protective effect). Cells that do not contain the vector would otherwise compete with transformed cells for resources. In one aspect, the antibiotic is tetracycline, neomycin, kanamycin, ampicillin, hygromycin, chloramphenicol, amphotericin B, bacitracin, carbapenam, cephalosporin, ethambutol, fluoroquinolones, isonizid, methicillin, oxacillin, vancomycin, streptomycin, quinolines, rifampin, rifampicin, sulfonamides, cephalothin, erythromycin, streptomycin, gentamicin, penicillin, other commonly-used antibiotics, or a combination thereof.

In one aspect, when the vector is a plasmid, the plasmid can also contain a multiple cloning site or polylinker. In a further aspect, the polylinker contains recognition sites for multiple restriction enzymes. The polylinker can contain up to 2, 3, 4, 5, 6, 7, 8, 9, 10, 11, 12, 13, 14, 15, 16, 17, 18, 19, 20, or more than 20 recognition sites for restriction enzymes. Further, restriction sites may be added, disabled, or removed as required, using techniques known in the art. In one aspect, the plasmid contains restriction sites for any known restriction enzyme such as, for example, HindIII, KpnI, SacI, BamHI, BstXI, EcoRI, BsaBI, NotI, XhoI, SphI, SbaI, ApaI, SalI, ClaI, EcoRV, PstI, SmaI, XmaI, SpeI, EagI, SacII, or any combination thereof. In a further aspect, the plasmid contains more than one recognition site for the same restriction enzyme.

In one aspect, the restriction enzyme can cleave DNA at a palindromic or an asymmetrical restriction site. In a further aspect, the restriction enzyme cleaves DNA to leave blunt ends; in an alternative aspect, the restriction enzyme cleaves DNA to leave "sticky" or overhanging ends. In another aspect, the enzyme can cleave DNA a distance of from 20 bases to over 1000 bases away from the restriction site. A variety of restriction enzymes are commercially available and their recognition sequences, as well as instructions for use (e.g., amount of DNA needed, precise volumes of reagents, purification techniques, as well as information about salt concentration, pH, optimum temperature, incubation time, and the like) are made available by commercial enzyme suppliers.

In one aspect, a plasmid with a polylinker containing one or more restriction sites can be digested with one restriction enzyme and a nucleotide sequence of interest can be ligated into the plasmid using a commercially available DNA ligase enzyme. Several such enzymes are available, often as kits containing all reagents and instructions required for use. In another aspect, a plasmid with a polylinker containing two or more restriction sites can be simultaneously digested with two restriction enzymes and a nucleotide sequence of interest can be ligated into the plasmid using a DNA ligase enzyme. Using two restriction enzymes provides an asymmetric cut in the DNA, allowing for insertion of a nucleotide sequence of interest in a particular direction and/or on a particular strand of the double-stranded plasmid. Since RNA synthesis from a DNA template proceeds from 5' to 3', often starting just after a promoter, the order and direction of elements inserted into a plasmid is especially important. If a plasmid is to be simultaneously digested with multiple restriction enzymes, these enzymes must be compatible in terms of buffer, salt concentration, and other incubation parameters.

In some aspects, prior to ligation using a ligase enzyme, a plasmid that has been digested with a restriction enzyme is treated with an alkaline phosphatase enzyme to remove 5' terminal phosphate groups. This prevents self-ligation of the plasmid and thus facilitates ligation of heterologous nucleic acid fragments into the plasmid.

In one aspect, the nucleic acids (e.g., genes that express hexokinase, alcohol dehydrogenase, and the like) used in the DNA constructs described herein can be amplified using the polymerase chain reaction (PCR) prior to being ligated into a plasmid or other vector. Typically, PCR-amplification techniques make use of primers or short, chemically-synthesized oligonucleotides that are complementary to regions on each respective strand flanking the DNA or nucleotide sequence to be amplified. A person having ordinary skill in the art will be able to design or choose primers based on the desired experimental conditions. In general, primers should be designed to provide for efficient and faithful replication of the target nucleic acids. Two primers are required for the amplification of each gene, one for the sense strand (that is, the strand containing the gene of interest) and one for the antisense strand (that is, the strand complementary to the gene of interest). Pairs of primers should have similar melting temperatures that are close to the PCR reaction's annealing temperature. In order to facilitate the PCR reaction, the following features should be avoided in primers: mononucleotide repeats, complementarity with other primers in the mixture, self-complementarity, and internal hairpins and/or loops. Methods of primer design are known in the art; additionally, computer programs exist that can assist the ordinarily skilled practitioner with primer design. Primers can optionally incorporate restriction enzyme recognition sites at their 5' ends to assist in later ligation into plasmids or other vectors.

PCR can be carried out using purified DNA, unpurified DNA that has been integrated into a vector, or unpurified genomic DNA. The process for amplifying target DNA using PCR consists of introducing an excess of two primers having the characteristics described above to a mixture containing the sequence to be amplified, followed by a series of thermal cycles in the presence of a heat-tolerant or thermophilic DNA polymerase, such as, for example, any of Taq, Pfu, Pwo, Tfl, rTth, Tli, or Tma polymerases. A PCR "cycle" involves denaturation of the DNA through heating, followed by annealing of the primers to the target DNA, followed by extension of the primers using the thermophilic DNA polymerase and a supply of deoxynucleotide triphosphates (i.e., dCTP, dATP, dGTP, and TTP), along with buffers, salts, and other reagents as needed. In one aspect, the DNA segments created by primer extension during the PCR process can serve as templates for additional PCR cycles. Many PCR cycles can be performed to generate a large concentration of target DNA or gene. PCR can optionally be performed in a device or machine with programmable temperature cycles for denaturation, annealing, and extension steps. Further, PCR can be performed on multiple genes simultaneously in the same reaction vessel or microcentrifuge tube since the primers chosen will be specific to selected genes. PCR products can be purified by techniques known in the art such as, for example, gel electrophoresis followed by extraction from the gel using commercial kits and reagents.

In a further aspect, the vector can include an origin of replication, allowing it to use the host cell's replication machinery to create copies of itself.

As used herein, "operably linked" refers to the association of nucleic acid sequences on a single nucleic acid fragment so that the function of one affects the function of another. For example, if sequences for multiple genes are inserted into a single plasmid, their expression may be operably linked. Alternatively, a promoter is said to be operably linked with a coding sequence when it is capable of affecting the expression of the coding sequence.

As used herein, "expression" refers to transcription and/or accumulation of an mRNA derived from a gene or DNA fragment. Expression may also be used to refer to translation of mRNA into a peptide, polypeptide, or protein.

In one aspect, the gene that expresses hexokinase is isolated from yeast. In one aspect, the yeast species is, for example, *Saccharomyces cerevisiae*. In one aspect, the *S. cerevisiae* is a strain of yeast such as, for example, S288C, ySR127, YJM1355, YJM453, YJM1202, YJM326, YJM1526, YJM470, YJM456, YJM1387, YJM682, or another commonly-used strain. In a further aspect, the gene that expresses hexokinase has SEQ ID NO. 4 or at least 70% homology thereof, at least 75% homology thereof, at least 80% homology thereof, at least 85% homology thereof, at least 90% homology thereof, or at least 95% homology thereof. In one aspect, the gene that expresses hexokinase is isolated from *Saccharomyces cerevisiae* and can be found in GenBank with accession number M14410.1.

Other sequences expressing hexokinase or related or homologous genes can be identified in a database such as, for example, GenBank. In one aspect, sequences useful herein include those with the GI numbers listed in Table 1.

TABLE 1

Hexokinase Genes

| Source Organism | Sequence Description | GI Number |
|---|---|---|
| *Saccharomyces cerevisiae* | hexokinase PI | M14410.1 |
| *Saccharomyces cerevisiae* | chromosome VI sequence | CP020128.1 |
| *Saccharomyces cerevisiae* | chromosome VI sequence | CP014737.1 |
| *Saccharomyces cerevisiae* | chromosome VI sequence | CP011552.1 |
| *Saccharomyces cerevisiae* | hexokinase 1 | NM_001180018.3 |
| *Saccharomyces cerevisiae* | chromosome VI sequence | BK006940.2 |
| *Saccharomyces cerevisiae* | chromosome VI sequence | D50617.1 |
| *Saccharomyces cerevisiae* | hexokinase 1 | DQ332072.1 |
| *Saccharomyces cerevisiae* | chromosome VI sequence | CP004946.2 |
| *Saccharomyces cerevisiae* | chromosome VI sequence | CP008547.1 |
| *Saccharomyces cerevisiae* | chromosome VI sequence | CP008530.1 |
| *Saccharomyces cerevisiae* | chromosome VI sequence | CP007901.1 |
| *Saccharomyces cerevisiae* | chromosome VI sequence | CP004902.2 |
| *Saccharomyces cerevisiae* | chromosome VI sequence | CP004929.2 |
| *Saccharomyces cerevisiae* | chromosome VI sequence | CP004898.2 |
| *Saccharomyces cerevisiae* | chromosome VI sequence | CP008462.1 |
| *Saccharomyces cerevisiae* | chromosome VI sequence | CP004975.2 |
| *Saccharomyces cerevisiae* | chromosome VI sequence | CP004904.2 |
| *Saccharomyces cerevisiae* | chromosome VI sequence | CP004903.2 |
| *Saccharomyces cerevisiae* | chromosome VI sequence | CP004952.2 |
| *Saccharomyces cerevisiae* | chromosome VI sequence | CP004910.2 |
| *Saccharomyces cerevisiae* | hexokinase isoenzyme 1 | JF898945.1 |
| *Saccharomyces cerevisiae* | chromosome VI sequence | CP008105.1 |
| *Saccharomyces cerevisiae* | chromosome VI sequence | CP008071.1 |
| *Saccharomyces cerevisiae* | chromosome VI sequence | CP004909.2 |
| *Saccharomyces cerevisiae* | chromosome VI sequence | CP004927.2 |
| *Saccharomyces cerevisiae* | chromosome VI sequence | CP008241.1 |
| *Saccharomyces cerevisiae* | chromosome VI sequence | CP008292.1 |
| *Saccharomyces cerevisiae* | chromosome VI sequence | CP008275.1 |
| *Saccharomyces cerevisiae* | chromosome VI sequence | CP008224.1 |
| *Saccharomyces cerevisiae* | chromosome VI sequence | CP008411.1 |
| *Saccharomyces cerevisiae* | chromosome VI sequence | CP008377.1 |
| *Saccharomyces cerevisiae* | chromosome VI sequence | CP008428.1 |
| *Saccharomyces cerevisiae* | chromosome VI sequence | CP008581.1 |
| *Saccharomyces cerevisiae* | chromosome VI sequence | CP008598.1 |
| *Saccharomyces cerevisiae* | chromosome VI sequence | CP008173.1 |
| *Saccharomyces cerevisiae* | chromosome VI sequence | CP008156.1 |
| *Saccharomyces cerevisiae* | chromosome VI sequence | CP008683.1 |
| *Saccharomyces cerevisiae* | chromosome VI sequence | CP008088.1 |
| *Saccharomyces cerevisiae* | chromosome VI sequence | CP008020.1 |
| *Saccharomyces cerevisiae* | chromosome VI sequence | CP007986.1 |
| *Saccharomyces cerevisiae* | chromosome VI sequence | CP007969.1 |
| *Saccharomyces cerevisiae* | chromosome VI sequence | CP007952.1 |
| *Saccharomyces cerevisiae* | chromosome VI sequence | CP007918.1 |
| *Saccharomyces cerevisiae* | chromosome VI sequence | CP007884.1 |
| *Saccharomyces cerevisiae* | chromosome VI sequence | CP007867.1 |
| *Saccharomyces cerevisiae* | chromosome VI sequence | CP004925.2 |
| *Saccharomyces cerevisiae* | chromosome VI sequence | CP004934.2 |
| *Saccharomyces cerevisiae* | chromosome VI sequence | CP004913.2 |
| *Saccharomyces cerevisiae* | chromosome VI sequence | CP004893.2 |
| *Saccharomyces cerevisiae* | chromosome VI sequence | CP004951.2 |
| *Saccharomyces cerevisiae* | chromosome VI sequence | CP004890.2 |
| *Saccharomyces cerevisiae* | chromosome VI sequence | CP004949.1 |
| *Saccharomyces cerevisiae* | chromosome VI sequence | CP004948.1 |
| *Saccharomyces cerevisiae* | chromosome VI sequence | CP004940.1 |
| *Saccharomyces cerevisiae* | hexokinase isoenzyme 1 | JF898949.1 |
| *Saccharomyces cerevisiae* | hexokinase isoenzyme 1 | JF898946.1 |
| *Saccharomyces cerevisiae* | chromosome VI sequence | CP008258.1 |
| *Saccharomyces cerevisiae* | chromosome VI sequence | CP008394.1 |
| *Saccharomyces cerevisiae* | chromosome VI sequence | CP008496.1 |
| *Saccharomyces cerevisiae* | chromosome VI sequence | CP008445.1 |
| *Saccharomyces cerevisiae* | chromosome VI sequence | CP008513.1 |
| *Saccharomyces cerevisiae* | hexokinase isoenzyme 1 | JF898948.1 |
| *Saccharomyces cerevisiae* | chromosome VI sequence | CP020162.1 |
| *Saccharomyces cerevisiae* | chromosome VI sequence | CP004979.2 |

TABLE 1-continued

Hexokinase Genes

| Source Organism | Sequence Description | GI Number |
| --- | --- | --- |
| Saccharomyces cerevisiae | chromosome VI sequence | CP004919.2 |
| Saccharomyces cerevisiae | chromosome VI sequence | CP004918.2 |
| Saccharomyces cerevisiae | chromosome VI sequence | CP004908.2 |
| Saccharomyces cerevisiae | chromosome VI sequence | CP004917.2 |
| Saccharomyces cerevisiae | chromosome VI sequence | CP004907.2 |
| Saccharomyces cerevisiae | chromosome VI sequence | CP004897.2 |
| Saccharomyces cerevisiae | chromosome VI sequence | CP004916.2 |
| Saccharomyces cerevisiae | chromosome VI sequence | CP004906.2 |
| Saccharomyces cerevisiae | chromosome VI sequence | CP004896.2 |
| Saccharomyces cerevisiae | chromosome VI sequence | CP008326.1 |
| Saccharomyces cerevisiae | chromosome VI sequence | CP008309.1 |
| Saccharomyces cerevisiae | chromosome VI sequence | CP008360.1 |
| Saccharomyces cerevisiae | chromosome VI sequence | CP008343.1 |
| Saccharomyces cerevisiae | chromosome VI sequence | CP008479.1 |
| Saccharomyces cerevisiae | chromosome VI sequence | CP008564.1 |
| Saccharomyces cerevisiae | chromosome VI sequence | CP008666.1 |
| Saccharomyces cerevisiae | chromosome VI sequence | CP008649.1 |
| Saccharomyces cerevisiae | chromosome VI sequence | CP008615.1 |
| Saccharomyces cerevisiae | chromosome VI sequence | CP008122.1 |
| Saccharomyces cerevisiae | chromosome VI sequence | CP008054.1 |
| Saccharomyces cerevisiae | chromosome VI sequence | CP008037.1 |
| Saccharomyces cerevisiae | chromosome VI sequence | CP007935.1 |
| Saccharomyces cerevisiae | chromosome VI sequence | CP007850.1 |
| Saccharomyces cerevisiae | chromosome VI sequence | CP007816.1 |
| Saccharomyces cerevisiae | chromosome VI sequence | CP004915.2 |
| Saccharomyces cerevisiae | chromosome VI sequence | CP004905.2 |
| Saccharomyces cerevisiae | chromosome VI sequence | CP004944.2 |
| Saccharomyces cerevisiae | chromosome VI sequence | CP004914.2 |
| Saccharomyces cerevisiae | chromosome VI sequence | CP004963.2 |
| Saccharomyces cerevisiae | chromosome VI sequence | CP004923.2 |
| Saccharomyces cerevisiae | chromosome VI sequence | CP004932.2 |
| Saccharomyces cerevisiae | chromosome VI sequence | CP004922.2 |
| Saccharomyces cerevisiae | chromosome VI sequence | CP004972.2 |
| Saccharomyces cerevisiae | chromosome VI sequence | CP004931.2 |
| Saccharomyces cerevisiae | chromosome VI sequence | CP007833.1 |

In one aspect, the gene that expresses a heat shock protein is isolated from yeast. In one aspect, the yeast species is, for example, *Saccharomyces cerevisiae*. In one aspect, the *S. cerevisiae* is a strain of yeast such as, for example, S288C, ySR127, YJM1355, YJM453, YJM1202, YJM326, YJM1526, YJM470, YJM456, YJM1387, YJM682, or another commonly-used strain. In a further aspect, the gene that expresses a heat shock protein is HSP70 and has SEQ ID NO. 5 or at least 70% homology thereof, at least 75% homology thereof, at least 80% homology thereof, at least 85% homology thereof, at least 90% homology thereof, or at least 95% homology thereof. In one aspect, the gene that expresses a heat shock protein is isolated from *Saccharomyces cerevisiae* and can be found in GenBank with accession number X13713.

Other sequences expressing heat shock proteins or related or homologous genes can be identified in a database such as, for example, GenBank. In one aspect, sequences useful herein include those with the GI numbers listed in Table 2.

TABLE 2

Heat Shock Protein Genes

| Source Organism | Sequence Description | GI Number |
| --- | --- | --- |
| Saccharomyces cerevisiae | chromosome IV sequence | CP020126.1 |
| Saccharomyces cerevisiae | chromosome IV sequence | CP004710.2 |
| Saccharomyces cerevisiae | chromosome IV sequence | CP011550.1 |
| Saccharomyces cerevisiae | HSP70 family ATPase SSB1 | BK006938.2 |
| Saccharomyces cerevisiae | chromosome IV sequence | NM_001180289.1 |
| Saccharomyces cerevisiae | chromosome IV sequence | FN393064.1 |
| Saccharomyces cerevisiae | SSB1 heat shock cognate gene | Z74277.1 |
| Saccharomyces cerevisiae | chromosome IV sequence | X13713.1 |
| Saccharomyces cerevisiae | chromosome IV sequence | EF058944.1 |
| Saccharomyces cerevisiae | chromosome IV sequence | CP020228.1 |
| Saccharomyces cerevisiae | chromosome IV sequence | CP020160.1 |
| Saccharomyces cerevisiae | chromosome IV sequence | CP004738.2 |
| Saccharomyces cerevisiae | chromosome IV sequence | CP004688.2 |
| Saccharomyces cerevisiae | chromosome IV sequence | CP004678.2 |
| Saccharomyces cerevisiae | chromosome IV sequence | CP004727.2 |
| Saccharomyces cerevisiae | chromosome IV sequence | CP004717.2 |
| Saccharomyces cerevisiae | chromosome IV sequence | CP004687.2 |
| Saccharomyces cerevisiae | chromosome IV sequence | CP004667.2 |
| Saccharomyces cerevisiae | chromosome IV sequence | CP004746.2 |

TABLE 2-continued

Heat Shock Protein Genes

| Source Organism | Sequence Description | GI Number |
| --- | --- | --- |
| Saccharomyces cerevisiae | chromosome IV sequence | CP004716.2 |
| Saccharomyces cerevisiae | chromosome IV sequence | CP004676.2 |
| Saccharomyces cerevisiae | chromosome IV sequence | CP008239.1 |
| Saccharomyces cerevisiae | chromosome IV sequence | CP008324.1 |
| Saccharomyces cerevisiae | chromosome IV sequence | CP008273.1 |
| Saccharomyces cerevisiae | chromosome IV sequence | CP008256.1 |
| Saccharomyces cerevisiae | chromosome IV sequence | CP008222.1 |
| Saccharomyces cerevisiae | chromosome IV sequence | CP008409.1 |
| Saccharomyces cerevisiae | chromosome IV sequence | CP008392.1 |
| Saccharomyces cerevisiae | chromosome IV sequence | CP008375.1 |
| Saccharomyces cerevisiae | chromosome IV sequence | CP008358.1 |
| Saccharomyces cerevisiae | chromosome IV sequence | CP008341.1 |
| Saccharomyces cerevisiae | chromosome IV sequence | CP008494.1 |
| Saccharomyces cerevisiae | chromosome IV sequence | CP008443.1 |
| Saccharomyces cerevisiae | chromosome IV sequence | CP008579.1 |
| Saccharomyces cerevisiae | chromosome IV sequence | CP008511.1 |
| Saccharomyces cerevisiae | chromosome IV sequence | CP008647.1 |
| Saccharomyces cerevisiae | chromosome IV sequence | CP008630.1 |
| Saccharomyces cerevisiae | chromosome IV sequence | CP008596.1 |
| Saccharomyces cerevisiae | chromosome IV sequence | CP008188.1 |
| Saccharomyces cerevisiae | chromosome IV sequence | CP008171.1 |
| Saccharomyces cerevisiae | chromosome IV sequence | CP008154.1 |
| Saccharomyces cerevisiae | chromosome IV sequence | CP008681.1 |
| Saccharomyces cerevisiae | chromosome IV sequence | CP008137.1 |
| Saccharomyces cerevisiae | chromosome IV sequence | CP008120.1 |
| Saccharomyces cerevisiae | chromosome IV sequence | CP008086.1 |
| Saccharomyces cerevisiae | chromosome IV sequence | CP008052.1 |
| Saccharomyces cerevisiae | chromosome IV sequence | CP008035.1 |
| Saccharomyces cerevisiae | chromosome IV sequence | CP008001.1 |
| Saccharomyces cerevisiae | chromosome IV sequence | CP007984.1 |
| Saccharomyces cerevisiae | chromosome IV sequence | CP007950.1 |
| Saccharomyces cerevisiae | chromosome IV sequence | CP007899.1 |
| Saccharomyces cerevisiae | chromosome IV sequence | CP007882.1 |
| Saccharomyces cerevisiae | chromosome IV sequence | CP007831.1 |
| Saccharomyces cerevisiae | chromosome IV sequence | CP004745.2 |
| Saccharomyces cerevisiae | chromosome IV sequence | CP004684.2 |
| Saccharomyces cerevisiae | chromosome IV sequence | CP004743.2 |
| Saccharomyces cerevisiae | chromosome IV sequence | CP004713.2 |
| Saccharomyces cerevisiae | chromosome IV sequence | CP004692.2 |
| Saccharomyces cerevisiae | chromosome IV sequence | CP004742.2 |
| Saccharomyces cerevisiae | chromosome IV sequence | CP004722.2 |
| Saccharomyces cerevisiae | chromosome IV sequence | CP004672.2 |
| Saccharomyces cerevisiae | chromosome IV sequence | CP004701.2 |
| Saccharomyces cerevisiae | chromosome IV sequence | CP004681.2 |
| Saccharomyces cerevisiae | chromosome IV sequence | CP004690.2 |
| Saccharomyces cerevisiae | chromosome IV sequence | CP004670.2 |
| Saccharomyces cerevisiae | chromosome IV sequence | CP011082.1 |
| Saccharomyces cerevisiae | chromosome IV sequence | CP004729.1 |
| Saccharomyces cerevisiae | heat shock protein 70 | M25395.1 |
| Saccharomyces cerevisiae | chromosome IV sequence | CP020211.1 |
| Saccharomyces cerevisiae | chromosome IV sequence | CP004748.2 |
| Saccharomyces cerevisiae | chromosome IV sequence | CP004697.2 |
| Saccharomyces cerevisiae | chromosome IV sequence | CP004677.2 |
| Saccharomyces cerevisiae | chromosome IV sequence | CP004726.2 |
| Saccharomyces cerevisiae | chromosome IV sequence | CP004706.2 |
| Saccharomyces cerevisiae | chromosome IV sequence | CP008307.1 |
| Saccharomyces cerevisiae | chromosome IV sequence | CP008290.1 |
| Saccharomyces cerevisiae | chromosome IV sequence | CP008477.1 |
| Saccharomyces cerevisiae | chromosome IV sequence | CP008460.1 |
| Saccharomyces cerevisiae | chromosome IV sequence | CP008426.1 |
| Saccharomyces cerevisiae | chromosome IV sequence | CP008562.1 |
| Saccharomyces cerevisiae | chromosome IV sequence | CP008664.1 |
| Saccharomyces cerevisiae | chromosome IV sequence | CP008613.1 |
| Saccharomyces cerevisiae | chromosome IV sequence | CP008103.1 |
| Saccharomyces cerevisiae | chromosome IV sequence | CP008069.1 |
| Saccharomyces cerevisiae | chromosome IV sequence | CP008018.1 |
| Saccharomyces cerevisiae | chromosome IV sequence | CP007967.1 |
| Saccharomyces cerevisiae | chromosome IV sequence | CP007933.1 |
| Saccharomyces cerevisiae | chromosome IV sequence | CP007916.1 |
| Saccharomyces cerevisiae | chromosome IV sequence | CP007865.1 |
| Saccharomyces cerevisiae | chromosome IV sequence | CP007848.1 |
| Saccharomyces cerevisiae | chromosome IV sequence | CP007814.1 |
| Saccharomyces cerevisiae | chromosome IV sequence | CP004695.2 |
| Saccharomyces cerevisiae | chromosome IV sequence | CP004675.2 |
| Saccharomyces cerevisiae | chromosome IV sequence | CP004744.2 |
| Saccharomyces cerevisiae | chromosome IV sequence | CP004724.2 |

TABLE 2-continued

Heat Shock Protein Genes

| Source Organism | Sequence Description | GI Number |
|---|---|---|
| Saccharomyces cerevisiae | chromosome IV sequence | CP004714.2 |
| Saccharomyces cerevisiae | chromosome IV sequence | CP004704.2 |
| Saccharomyces cerevisiae | chromosome IV sequence | CP004674.2 |
| Saccharomyces cerevisiae | chromosome IV sequence | CP004733.2 |
| Saccharomyces cerevisiae | chromosome IV sequence | CP008205.1 |

In one aspect, the gene that expresses alcohol dehydrogenase is isolated from yeast. In one aspect, the yeast species is, for example, Saccharomyces cerevisiae. In one aspect, the S. cerevisiae is a strain of yeast such as, for example, S288C, ySR127, YJM1355, YJM453, YJM1202, YJM326, YJM1526, YJM470, YJM456, YJM1387, YJM682, or another commonly-used strain. In a further aspect, the gene that expresses alcohol dehydrogenase has SEQ ID NO. 6 or at least 70% homology thereof, at least 75% homology thereof, at least 80% homology thereof, at least 85% homology thereof, at least 90% homology thereof, or at least 95% homology thereof. In one aspect, the gene that expresses alcohol dehydrogenase is isolated from Saccharomyces cerevisiae and can be found in GenBank with GI number J01314.1.

Other sequences expressing alcohol dehydrogenase or related or homologous genes can be identified in a database such as, for example, GenBank. In one aspect, sequences useful herein include those with the GI numbers listed in Table 3.

TABLE 3

Alcohol Dehydrogenase Genes

| Source Organism | Sequence Description | GI Number |
|---|---|---|
| Saccharomyces cerevisiae | alcohol dehydrogenase II gene | J01314.1 |
| Saccharomyces cerevisiae | chromosome XIII sequence | CP005453.2 |
| Saccharomyces cerevisiae | chromosome XIII sequence | CP020135.1 |
| Saccharomyces cerevisiae | chromosome XIII sequence | CP005452.2 |
| Saccharomyces cerevisiae | chromosome XIII sequence | CP005450.2 |
| Saccharomyces cerevisiae | chromosome XIII sequence | BK006946.2 |
| Saccharomyces cerevisiae | alcohol dehydrogenase II gene | NM_001182812.1 |
| Saccharomyces cerevisiae | alcohol dehydrogenase II gene | EF059086.1 |
| Saccharomyces cerevisiae | chromosome XIII sequence | Z49212.1 |
| Saccharomyces cerevisiae | glucose-repressible ADH2 | KJ137139.1 |
| Saccharomyces cerevisiae | alcohol dehydrogenase II gene | M38457.1 |
| Saccharomyces cerevisiae | glucose-repressible ADH2 | KJ137141.1 |
| Saccharomyces cerevisiae | glucose-repressible ADH2 | KJ137132.1 |
| Saccharomyces cerevisiae | chromosome XIII sequence | CP005464.2 |
| Saccharomyces cerevisiae | chromosome XIII sequence | CP005483.2 |
| Saccharomyces cerevisiae | chromosome XIII sequence | CP005432.2 |
| Saccharomyces cerevisiae | chromosome XIII sequence | CP020203.1 |
| Saccharomyces cerevisiae | chromosome XIII sequence | CP005482.2 |
| Saccharomyces cerevisiae | chromosome XIII sequence | CP005472.2 |
| Saccharomyces cerevisiae | chromosome XIII sequence | LN907796.1 |
| Saccharomyces cerevisiae | chromosome XIII sequence | CP005456.1 |
| Saccharomyces cerevisiae | chromosome XIII sequence | CP005455.1 |
| Saccharomyces cerevisiae | chromosome XIII sequence | CP005440.1 |
| Saccharomyces cerevisiae | chromosome XIII sequence | CP005465.2 |
| Saccharomyces cerevisiae | chromosome XIII sequence | CP005405.2 |
| Saccharomyces cerevisiae | chromosome XIII sequence | CP005414.2 |
| Saccharomyces cerevisiae | chromosome XIII sequence | CP005403.2 |
| Saccharomyces cerevisiae | chromosome XIII sequence | CP005412.2 |
| Saccharomyces cerevisiae | chromosome XIII sequence | CP011559.1 |
| Saccharomyces cerevisiae | chromosome XIII sequence | CP005426.1 |
| Saccharomyces cerevisiae | chromosome XIII sequence | CP005406.1 |
| Saccharomyces cerevisiae | alcohol dehydrogenase II gene | JX901290.1 |
| Saccharomyces cerevisiae | chromosome XIII sequence | CP005451.2 |
| Saccharomyces cerevisiae | chromosome XIII sequence | CP005436.1 |
| Saccharomyces cerevisiae | glucose-repressible ADH2 | KJ137135.1 |
| Saccharomyces cerevisiae | chromosome XIII sequence | CP008010.1 |
| Saccharomyces cerevisiae | chromosome XIII sequence | CP020169.1 |
| Saccharomyces cerevisiae | chromosome XIII sequence | CP005449.2 |
| Saccharomyces cerevisiae | chromosome XIII sequence | CP005429.2 |
| Saccharomyces cerevisiae | chromosome XIII sequence | CP005419.2 |
| Saccharomyces cerevisiae | chromosome XIII sequence | CP005409.2 |
| Saccharomyces cerevisiae | chromosome XIII sequence | CP005428.2 |
| Saccharomyces cerevisiae | chromosome XIII sequence | CP005418.2 |
| Saccharomyces cerevisiae | chromosome XIII sequence | CP005408.2 |
| Saccharomyces cerevisiae | chromosome XIII sequence | CP005477.2 |
| Saccharomyces cerevisiae | chromosome XIII sequence | CP005417.2 |
| Saccharomyces cerevisiae | chromosome XIII sequence | CP005425.2 |
| Saccharomyces cerevisiae | chromosome XIII sequence | CP008265.1 |
| Saccharomyces cerevisiae | chromosome XIII sequence | CP008367.1 |
| Saccharomyces cerevisiae | chromosome XIII sequence | CP008554.1 |
| Saccharomyces cerevisiae | chromosome XIII sequence | CP008537.1 |
| Saccharomyces cerevisiae | chromosome XIII sequence | CP008520.1 |
| Saccharomyces cerevisiae | chromosome XIII sequence | CP008129.1 |
| Saccharomyces cerevisiae | chromosome XIII sequence | CP007993.1 |
| Saccharomyces cerevisiae | chromosome XIII sequence | CP005444.2 |
| Saccharomyces cerevisiae | chromosome XIII sequence | CP005434.2 |
| Saccharomyces cerevisiae | chromosome XIII sequence | CP005424.2 |
| Saccharomyces cerevisiae | chromosome XIII sequence | CP005404.2 |
| Saccharomyces cerevisiae | chromosome XIII sequence | CP005423.2 |
| Saccharomyces cerevisiae | chromosome XIII sequence | CP005422.2 |
| Saccharomyces cerevisiae | chromosome XIII sequence | CP005402.2 |
| Saccharomyces cerevisiae | chromosome XIII sequence | CP005421.2 |
| Saccharomyces cerevisiae | chromosome XIII sequence | CP005411.2 |
| Saccharomyces cerevisiae | chromosome XIII sequence | CP005420.2 |
| Saccharomyces cerevisiae | chromosome XIII sequence | CP005427.1 |
| Saccharomyces cerevisiae | chromosome XIII sequence | CP005416.1 |
| Saccharomyces cerevisiae | glucose-repressible ADH2 | KJ137136.1 |
| Saccharomyces cerevisiae | glucose-repressible ADH2 | KJ137134.1 |
| Saccharomyces cerevisiae | glucose-repressible ADH2 | KJ137133.1 |
| Saccharomyces cerevisiae | glucose-repressible ADH2 | KJ137142.1 |
| Saccharomyces cerevisiae | glucose-repressible ADH2 | KJ137138.1 |
| Saccharomyces cerevisiae | chromosome XIII sequence | CP005475.2 |
| Saccharomyces cerevisiae | chromosome XIII sequence | CP008401.1 |
| Saccharomyces cerevisiae | chromosome XIII sequence | CP008503.1 |
| Saccharomyces cerevisiae | chromosome XIII sequence | CP005398.2 |
| Saccharomyces cerevisiae | chromosome XIII sequence | CP005478.2 |
| Saccharomyces cerevisiae | chromosome XIII sequence | CP005437.2 |
| Saccharomyces cerevisiae | chromosome XIII sequence | CP005407.2 |
| Saccharomyces cerevisiae | chromosome XIII sequence | CP005454.2 |
| Saccharomyces cerevisiae | chromosome XIII sequence | CP005462.2 |
| Saccharomyces cerevisiae | chromosome XIII sequence | CP005461.2 |
| Saccharomyces cerevisiae | chromosome XIII sequence | CP005401.2 |
| Saccharomyces cerevisiae | chromosome XIII sequence | CP005396.1 |
| Saccharomyces cerevisiae | chromosome XIII sequence | CP005479.2 |
| Saccharomyces cerevisiae | chromosome XIII sequence | CP005469.2 |
| Saccharomyces cerevisiae | chromosome XIII sequence | CP005399.2 |
| Saccharomyces cerevisiae | chromosome XIII sequence | CP005397.2 |
| Saccharomyces cerevisiae | chromosome XIII sequence | CP005415.2 |
| Saccharomyces cerevisiae | chromosome XIII sequence | CP005395.2 |
| Saccharomyces cerevisiae | chromosome XIII sequence | CP008248.1 |
| Saccharomyces cerevisiae | chromosome XIII sequence | CP008333.1 |

TABLE 3-continued

Alcohol Dehydrogenase Genes

| Source Organism | Sequence Description | GI Number |
|---|---|---|
| Saccharomyces cerevisiae | chromosome XIII sequence | CP008316.1 |
| Saccharomyces cerevisiae | chromosome XIII sequence | CP008299.1 |
| Saccharomyces cerevisiae | chromosome XIII sequence | CP008282.1 |
| Saccharomyces cerevisiae | chromosome XIII sequence | CP008231.1 |
| Saccharomyces cerevisiae | chromosome XIII sequence | CP008418.1 |
| Saccharomyces cerevisiae | chromosome XIII sequence | CP008384.1 |
| Saccharomyces cerevisiae | chromosome XIII sequence | CP008350.1 |
| Saccharomyces cerevisiae | chromosome XIII sequence | CP008486.1 |
| Saccharomyces cerevisiae | chromosome XIII sequence | CP008469.1 |

In one aspect, the gene that expresses an iron promoter is isolated from a bacterium. In one aspect, the bacterium species is a *Mycobacterium* species such as, for example, *M. avium, M. yongonense, M. chimaera, M. intracellulare, M. kansasii, M. marinum, M. ulcerans*, or *M. tuberculosis*. In a further aspect, the gene that expresses iron promoter has SEQ ID NO. 7 or at least 70% homology thereof, at least 75% homology thereof, at least 80% homology thereof, at least 85% homology thereof, at least 90% homology thereof, or at least 95% homology thereof. In one aspect, the gene that expresses an iron promoter is isolated from *Mycobacterium avium* subsp. *paratuberculosis* MAP4 and can be found in GenBank with GI number CP005928.

Other sequences expressing an iron promoter or related or homologous genes can be identified in a database such as, for example, GenBank. In one aspect, sequences useful herein include those with the GI numbers listed in Table 4.

TABLE 4

Iron Promoter Genes

| Source Organism | Sequence Description | GI Number |
|---|---|---|
| Mycobacterium avium subsp. paratuberculosis | genomic DNA | CP015495.1 |
| Mycobacterium avium subsp. paratuberculosis | genomic DNA | CP010114.1 |
| Mycobacterium avium subsp. paratuberculosis | genomic DNA | CP010113.1 |
| Mycobacterium avium subsp. paratuberculosis | genomic DNA | CP005928.1 |
| Mycobacterium avium subsp. paratuberculosis | genomic DNA | AF280067.2 |
| Mycobacterium avium subsp. paratuberculosis | genomic DNA | AE016958.1 |
| Mycobacterium avium subsp. hominissuis | genomic DNA | AP012555.1 |
| Mycobacterium avium subsp. hominissuis | | CP018363.1 |
| Mycobacterium avium subsp. avium | genomic DNA | CP009614.1 |
| Mycobacterium avium subsp. avium | genomic DNA | CP009482.1 |
| Mycobacterium avium subsp. avium | genomic DNA | CP009493.1 |
| Mycobacterium avium | genomic DNA | CP000479.1 |
| Mycobacterium avium | genomic DNA | CP016396.1 |
| Mycobacterium avium | genomic DNA | D78144.1 |
| Mycobacterium avium subsp. paratuberculosis | genomic DNA | AJ584651.1 |
| Mycobacterium avium subsp. avium | genomic DNA | AB325677.1 |
| Mycobacterium colombiense | genomic DNA | CP020821.1 |
| Mycobacterium chimaera | genomic DNA | CP019221.1 |
| Mycobacterium yongonense | genomic DNA | CP015965.1 |
| Mycobacterium yongonense | genomic DNA | CP015964.1 |
| Mycobacterium chimaera | genomic DNA | LT703505.1 |
| Mycobacterium chimaera | genomic DNA | CP012885.2 |
| Mycobacterium intracellulare | genomic DNA | CP009499.1 |
| Mycobacterium sp. 05-1390 | genomic DNA | CP003347.1 |
| Mycobacterium indicus pranii | genomic DNA | CP002275.1 |
| Mycobacterium sp. MOTT36Y | genomic DNA | CP003491.1 |
| Mycobacterium intracellulare | genomic DNA | CP003324.1 |
| Mycobacterium intracellulare | genomic DNA | CP003323.1 |
| Mycobacterium intracellulare | genomic DNA | CP003322.1 |
| Mycobacterium simiae | genomic DNA | CP010996.1 |
| Mycobacterium shigaense | genomic DNA | AP018164.1 |
| Mycobacterium gordonae | genomic DNA | Y10378.1 |
| Mycobacterium kansasii | genomic DNA | CP019888.1 |
| Mycobacterium kansasii | genomic DNA | CP019887.1 |
| Mycobacterium kansasii | genomic DNA | CP019886.1 |
| Mycobacterium kansasii | genomic DNA | CP019885.1 |
| Mycobacterium kansasii | genomic DNA | CP019884.1 |
| Mycobacterium kansasii | genomic DNA | CP019883.1 |
| Mycobacterium kansasii | genomic DNA | CP009483.1 |
| Mycobacterium kansasii | genomic DNA | CP006835.1 |
| Mycobacterium marinum | genomic DNA | AB716948.1 |
| Mycobacterium marinum | genomic DNA | HG917972.2 |
| Mycobacterium marinum | genomic DNA | CP000854.1 |
| Mycobacterium marinum | genomic DNA | AB716942.1 |
| Mycobacterium ulcerans | genomic DNA | AP017635.1 |
| Mycobacterium ulcerans | genomic DNA | AP017624.1 |
| Mycobacterium liflandii | genomic DNA | CP003899.1 |
| Mycobacterium marinum | genomic DNA | AY225215.1 |
| Mycobacterium ulcerans | genomic DNA | CP000325.1 |
| Mycobacterium sp. 012931 | genomic DNA | AB716954.1 |
| Mycobacterium ulcerans | genomic DNA | AJ300576.1 |
| Mycobacterium haemophilum | genomic DNA | CP011883.2 |
| Mycobacterium tuberculosis | genomic DNA | CP010340.1 |
| Mycobacterium tuberculosis | genomic DNA | CP005386.1 |
| Mycobacterium canettii | genomic DNA | FO203510.1 |
| Mycobacterium canettii | genomic DNA | FO203508.1 |
| Mycobacterium tuberculosis | genomic DNA | GQ150314.1 |
| Mycobacterium tuberculosis | genomic DNA | AP018036.1 |
| Mycobacterium tuberculosis | genomic DNA | AP018035.1 |
| Mycobacterium tuberculosis | genomic DNA | AP018034.1 |
| Mycobacterium tuberculosis | genomic DNA | CP017598.1 |
| Mycobacterium tuberculosis | genomic DNA | CP017597.1 |
| Mycobacterium tuberculosis | genomic DNA | CP017596.1 |
| Mycobacterium tuberculosis | genomic DNA | CP017595.1 |
| Mycobacterium tuberculosis | genomic DNA | CP017594.1 |
| Mycobacterium tuberculosis | genomic DNA | CP017593.1 |
| Mycobacterium tuberculosis | genomic DNA | AP018033.1 |
| Mycobacterium tuberculosis | genomic DNA | CP020381.2 |
| Mycobacterium tuberculosis | genomic DNA | CP009195.1 |
| Mycobacterium tuberculosis | genomic DNA | CP009187.1 |
| Mycobacterium tuberculosis | genomic DNA | CP009186.1 |
| Mycobacterium tuberculosis | genomic DNA | CP009183.1 |
| Mycobacterium tuberculosis | genomic DNA | CP009206.1 |
| Mycobacterium tuberculosis | genomic DNA | CP009199.1 |
| Mycobacterium tuberculosis | genomic DNA | CP009202.1 |
| Mycobacterium tuberculosis | genomic DNA | CP009193.1 |
| Mycobacterium tuberculosis | genomic DNA | CP009192.1 |
| Mycobacterium tuberculosis | genomic DNA | CP009191.1 |
| Mycobacterium tuberculosis | genomic DNA | CP009190.1 |
| Mycobacterium tuberculosis | genomic DNA | CP009197.1 |
| Mycobacterium tuberculosis | genomic DNA | CP009196.1 |
| Mycobacterium tuberculosis | genomic DNA | CP009194.1 |
| Mycobacterium tuberculosis | genomic DNA | CP009189.1 |
| Mycobacterium tuberculosis | genomic DNA | CP009188.1 |
| Mycobacterium tuberculosis | genomic DNA | CP009185.1 |
| Mycobacterium tuberculosis | genomic DNA | CP009184.1 |
| Mycobacterium tuberculosis | genomic DNA | CP009182.1 |
| Mycobacterium tuberculosis | genomic DNA | CP009181.1 |
| Mycobacterium tuberculosis | genomic DNA | CP009180.1 |
| Mycobacterium tuberculosis | genomic DNA | CP009179.1 |
| Mycobacterium tuberculosis | genomic DNA | CP009178.1 |
| Mycobacterium tuberculosis | genomic DNA | CP009177.1 |
| Mycobacterium tuberculosis | genomic DNA | CP009176.1 |
| Mycobacterium tuberculosis | genomic DNA | CP009175.1 |
| Mycobacterium tuberculosis | genomic DNA | CP009174.1 |
| Mycobacterium tuberculosis | genomic DNA | CP009173.1 |
| Mycobacterium tuberculosis | genomic DNA | CP009172.1 |
| Mycobacterium tuberculosis | genomic DNA | CP009207.1 |
| Mycobacterium tuberculosis | genomic DNA | CP009204.1 |
| Mycobacterium tuberculosis | genomic DNA | CP009203.1 |

In one aspect, the gene that expresses transferrin is isolated from a mammal. In one aspect, the mammal species is a primate species such as, for example, a human, gorilla, bonobo, chimpanzee, gibbon, orangutan, macaque, baboon, lemur, Old World Monkey, or New World Monkey. In another aspect, the mammal species is a rodent species such as, for example, a ground squirrel, marmot, mouse, guinea pig, jerboa, chinchilla, degu, mole rat, or beaver. In still another aspect, the mammal species is a pika, tree shrew, or camel. In a further aspect, the gene that expresses transferrin has SEQ ID NO. 8 or at least 70% homology thereof, at least 75% homology thereof, at least 80% homology thereof, at least 85% homology thereof, at least 90% homology thereof, or at least 95% homology thereof. In one aspect, the gene that expresses transferrin is isolated from *Homo sapiens* and can be found in GenBank with GI number DQ923758.

Other sequences expressing transferrin or related or homologous genes can be identified in a database such as, for example, GenBank. In one aspect, sequences useful herein include those with the GI numbers listed in Table 5.

TABLE 5

Transferrin Genes

| Source Organism | Sequence Description | GI Number |
|---|---|---|
| *Homo sapiens* | transferrin | NM_001063.3 |
| *Homo sapiens* | transferrin | DQ923758.1 |
| *Gorilla gorilla* | transferrin variant X1 | XM_019022854.1 |
| *Gorilla gorilla* | transferrin | NM_001303546.1 |
| *Homo sapiens* | transferrin | S95936.1 |
| *Homo sapiens* | transferrin variant X2 | XM_017007090.1 |
| *Homo sapiens* | transferrin variant X1 | XM_017007089.1 |
| *Homo sapiens* | transferrin | M12530.1 |
| *Homo sapiens* | transferrin | AB590492.1 |
| *Homo sapiens* | transferrin | AK222755.1 |
| *Homo sapiens* | epididymis secretory sperm binding protein | GQ472199.1 |
| *Pan paniscus* | serotransferrin | XM_008976094.1 |
| *Homo sapiens* | transferrin | BC059367.1 |
| *Homo sapiens* | transferrin | KJ897654.1 |
| *Homo sapiens* | transferrin | CR936810.1 |
| *Pan troglodytes* | transferrin | NM_001144835.1 |
| *Nomascus leucogenys* | transferrin | XM_003265239.3 |
| *Pongo pygmaeus* | transferrin | KM972646.1 |
| *Nomascus leucogenys* | transferrin | NM_001308674.1 |
| *Pongo abelii* | transferrin | NM_001133958.1 |
| *Homo sapiens* | serotransferrin precursor | AK295419.1 |
| *Symphalangus syndactylus* | transferrin | KM972647.1 |
| *Hylobates lar* | transferrin | KM972649.1 |
| *Allenopithecus nigroviridis* | transferrin | KM972653.1 |
| *Homo sapiens* | transferrin | BX648533.1 |
| *Homo sapiens* | transferrin | AF118063.1 |
| *Trachypitecus francoisi* | transferrin | KM972656.1 |
| *Lophocebus albigena* | transferrin | KM972652.1 |
| *Colobus angolensis palliatus* | serotransferrin variant X1 | XM_011958201.1 |
| *Chlorocebus sabaeus* | transferrin variant X1 | XM_008009084.1 |
| *Macaca nemestrina* | transferrin | XM_011721456.1 |
| *Macaca fascicularis* | transferrin | AB169522.1 |
| *Colobus guereza* | transferrin | KM972655.1 |
| *Macaca fascicularis* | serotransferrin | XM_005545793.2 |
| *Cerocebus atys* | transferrin | XM_012061466.1 |
| *Mandrillus lecuophaeus* | transferrin variant X2 | XM_011970225.1 |
| *Macaca mulatta* | serotransferrin | NM_001318182.1 |
| *Mandrillus leucophaeus* | transferrin variant X1 | XM_011970224.1 |
| *Macaca fascicularis* | transferrin | AB170458.1 |
| *Pongo abelii* | transferrin | XM_009239319.1 |
| *Saimiri sciureus* | transferrin | KM972659.1 |

TABLE 5-continued

Transferrin Genes

| Source Organism | Sequence Description | GI Number |
|---|---|---|
| *Saimiri boliviensis* | transferrin | XM_003925066.2 |
| *Aotus nancymaae* | transferrin | NM_001308518.1 |
| *Papio anubis* | transferrin | KM972651.1 |
| *Cercopithecus ascanius* | transferrin | KM972654.1 |
| *Chlorocebus sabaeus* | transferrin variant X2 | XM_008009085.1 |
| *Papio anubis* | serotransferrin | XM_003895098.3 |
| *Rhinopithecus bieti* | serotransferrin variant X2 | XM_017872421.1 |
| *Rhinopithecus bieti* | serotransferrin variant X1 | XM_017872420.1 |
| *Lagothrix lagotricha* | transferrin | KM972663.1 |
| *Callithrix jacchus* | transferrin | XM_008983803.2 |
| *Callithrix geoffroyi* | transferrin | KM972658.1 |
| *Callicebus moloch* | transferrin | KM972661.1 |
| *Alouatta sara* | transferrin | KM972662.1 |
| *Homo sapiens* | serotransferrin precursor | AK295334.1 |
| *Cebus capucinus imitator* | transferrin variant X2 | XM_017505719.1 |
| *Homo sapiens* | serotransferrin precursor | AK303753.1 |
| *Saguinus fuscicollis* | transferrin | KM972657.1 |
| *Cebus capucinus imitator* | transferrin variant X1 | XR_001818300.1 |
| *Colobus angolensis* | serotransferrin variant X2 | XM_011958202.1 |
| *Tarsius syrichta* | serotransferrin-like protein | XM_008057562.1 |
| *Propithecus coquereli* | serotransferrin-like protein | XM_012664058.1 |
| *Microcebus murinus* | serotransferrin-like protein | XM_012766832.2 |
| *Galeopterus variegatus* | serotransferrin-like protein | XM_008581124.1 |
| *Ochotona princeps* | transferrin variant X1 | XM_004588321.2 |
| *Ictidomys tridecemileatus* | serotransferrin | XM_005327026.1 |
| *Oryctolagus cuniculus* | transferrin | NM_001101694.1 |
| *Marmota monax* | transferrin | AY288100.1 |
| *Ochotona princeps* | transferrin variant X2 | XM_004588320.2 |
| *Marmota marmota* | transferrin | XM_015487041.1 |
| *Jaculus jaculus* | transferrin variant X2 | XM_004664199.1 |
| *Chinchilla lanigera* | serotransferrin | XM_005406809.2 |
| *Nannospalax galili* | serotransferrin-like protein | XM_017802840.1 |
| *Octodon degus* | serotransferrin | XM_004625212.1 |
| *Tupaia chinensis* | transferrin | XM_014584459.1 |
| *Heterocephalus glaber* | serotransferrin | XM_004834254.3 |
| *Cavia porcellus* | serotransferrin | XM_003476728.3 |
| *Fukomys damarensis* | serotransferrin variant X2 | XM_010625485.2 |
| *Fukomys damarensis* | serotransferrin variant X1 | XM_010625484.2 |
| *Peromyscus maniculatus bairdii* | serotransferrin | XM_006978668.2 |
| *Rhinopithecus roxellana* | transferrin | XM_010379532.1 |
| Synthetic construct | fusion protein gene | JX091745.1 |
| *Castor canadensis* | serotransferrin-like protein | XM_020165722.1 |
| *Mus musculus* | transferrin | NM_133977.2 |
| *Mus musculus* | transferrin | AK142599.1 |
| *Mus musculus* | transferrin | AK168419.1 |
| *Mus musculus* | transferrin | AK149559.1 |
| *Mus musculus* | transferrin | AK085754.1 |
| *Camelus ferus* | transferrin | XM_006179717.2 |
| *Camelus dromedarius* | transferrin | XM_010975530.1 |
| *Camelus bactrianus* | transferrin | XM_010947720.1 |
| *Mus musculus* | transferrin | AK149595.1 |
| *Mus musculus* | transferrin | BC022986.1 |
| *Mus musculus* | transferrin | BC012313.1 |
| *Mus musculus* | transferrin | BC092046.1 |
| *Mus musculus* | transferrin | BC058218.1 |
| *Mus musculus* | transferrin | BC058216.1 |

TABLE 5-continued

Transferrin Genes

| Source Organism | Sequence Description | GI Number |
|---|---|---|
| Mus musculus | transferrin | BC020295.1 |
| Mus musculus | transferrin | AK168405.1 |
| Mus musculus | transferrin | AK150782.1 |

In one aspect, the gene that expresses flavonol synthase is isolated from a plant. In a further aspect, the gene that expresses flavonol synthase is isolated from a plant in the mustard family, or *Brassicaceae*. In one aspect, the mustard family species can be, for example, an *Arabidopsis* species (such as *A. thaliana*), pink shepherd's purse, saltwater cress, false flax, nakedstem wallflower, radish, wild cabbage (including any of the cultivars broccoli, cabbage, cauliflower, kale, Brussels sprouts, collard greens, or kohlrabi), turnip (including the Napa cabbage and bok choy cultivars), or canola (also known as rapeseed). In another aspect, the flavonol synthase is flavonol synthase 1. In a further aspect, the gene that expresses flavonol synthase has SEQ ID NO. 9 or at least 70% homology thereof, at least 75% homology thereof, at least 80% homology thereof, at least 85% homology thereof, at least 90% homology thereof, or at least 95% homology thereof. In one aspect, the gene that expresses flavonol synthase is isolated from *Fragaria x ananassa* (strawberry) and can be found in GenBank with GI number AAZ78661.1.

Other sequences expressing flavonol synthase or related or homologous genes can be identified in a database such as, for example, GenBank. In one aspect, sequences useful herein include those with the GI numbers listed in Table 6.

TABLE 6

Flavonol Synthase Genes

| Source Organism | Sequence Description | GI Number |
|---|---|---|
| Arabidopsis thaliana | flavonol synthase 1 | NM_120951.3 |
| Arabidopsis thaliana | flavonol synthase 1 | NM_001203337.1 |
| Arabidopsis thaliana | flavonol synthase | BT000494.1 |
| Arabidopsis thaliana | genomic DNA | AY058068.1 |
| Arabidopsis thaliana | flavonol synthase | U84259.1 |
| Arabidopsis thaliana | genomic DNA | AY086328.1 |
| Arabidopsis thaliana | flavonol synthase | U84260.1 |
| Arabidopsis lyrata | flavonol synthase/flavanone 3-hydroxylase | XM_021022274.1 |
| Camelina sativa | flavonol synthase/flavanone 3-hydroxylase | XM_010424737.2 |
| Camelina sativa | flavonol synthase/flavanone 3-hydroxylase-like protein | XM_010493211.2 |
| Capsella rubella | hypothetical protein | XM_006288082.1 |
| Camelina sativa | flavonol synthase/flavanone 3-hydroxylase-like protein | XM_010454576.2 |
| Eutrema salsugineum | hypothetical protein | XM_006399307.1 |
| Parrya nudicaulis | flavonol synthase | HQ215235.1 |
| Parrya nudicaulis | flavonol synthase | HQ215236.1 |
| Raphanus sativus | flavonol synthase/flavanone 3-hydroxylase | XM_018586825.1 |
| Brassica oleracea | flavonol synthase/flavanone 3-hydroxylase | XM_013751217.1 |
| Brassica rapa | flavonol synthase/flavanone 3-hydroxylase | XM_009124234.2 |
| Brassica napus | flavonol synthase/flavanone 3-hydroxylase | XM_013860217.1 |
| Arabidopsis thaliana | genomic DNA | CP002688.1 |
| Arabidopsis thaliana | flavone synthase, ecotype Col-2 | AM887647.1 |
| Arabidopsis thaliana | genomic DNA | AL590346.1 |
| Arabidopsis thaliana | flavonol synthase | U84258.1 |
| Arabidopsis thaliana | genomic DNA | AB006697.1 |

TABLE 6-continued

Flavonol Synthase Genes

| Source Organism | Sequence Description | GI Number |
|---|---|---|
| Arabidopsis thaliana | flavonol synthase 1 | EU287459.1 |
| Arabidopsis thaliana | flavonol synthase G68R variant | EU287458.1 |
| Arabidopsis thaliana | flavone synthase, ecotype Ita-0 | AM887658.1 |
| Arabidopsis thaliana | flavone synthase, ecotype La-0 | AM887653.1 |
| Arabidopsis thaliana | flavone synthase, ecotype Tul-0 | AM887651.1 |
| Arabidopsis thaliana | flavone synthase, ecotype Gr-5 | AM887648.1 |
| Arabidopsis thaliana | flavone synthase, ecotype Mr-0 | AM887645.1 |
| Arabidopsis thaliana | flavone synthase, ecotype Rub-1 | AM887643.1 |
| Arabidopsis thaliana | flavone synthase, ecotype Cha-0 | AM887641.1 |
| Arabidopsis thaliana | flavone synthase, ecotype Ws-0 | AM887640.1 |
| Arabidopsis thaliana | flavone synthase, ecotype Kas-1 | AM887639.1 |
| Arabidopsis thaliana | flavonol synthase 1 | U72631.1 |
| Arabidopsis thaliana | flavone synthase, ecotype Can-0 | AM887657.1 |
| Arabidopsis thaliana | flavone synthase, ecotype Cvi-0 | AM887642.1 |
| Arabidopsis lyrata | flavone synthase | AM887659.1 |
| Arabis alpina | genomic DNA | LT669795.1 |
| Eutrema salsugineum | hypothetical protein | XM_006401952.1 |
| Parrya nudicaulis | flavonol synthase | HQ215393.1 |
| Parrya nudicaulis | flavonol synthase | HQ215392.1 |
| Parrya nudicaulis | flavonol synthase | HQ215387.1 |
| Parrya nudicaulis | flavonol synthase | HQ215406.1 |
| Parrya nudicaulis | flavonol synthase | HQ215405.1 |
| Parrya nudicaulis | flavonol synthase | HQ215402.1 |
| Parrya nudicaulis | flavonol synthase | HQ215401.1 |
| Parrya nudicaulis | flavonol synthase | HQ215400.1 |
| Parrya nudicaulis | flavonol synthase | HQ215399.1 |
| Parrya nudicaulis | flavonol synthase | HQ215398.1 |
| Parrya nudicaulis | flavonol synthase | HQ215397.1 |
| Parrya nudicaulis | flavonol synthase | HQ215396.1 |
| Parrya nudicaulis | flavonol synthase | HQ215395.1 |
| Parrya nudicaulis | flavonol synthase | HQ215394.1 |
| Parrya nudicaulis | flavonol synthase | HQ215391.1 |
| Parrya nudicaulis | flavonol synthase | HQ215385.1 |
| Parrya nudicaulis | flavonol synthase | HQ215384.1 |
| Parrya nudicaulis | flavonol synthase | HQ215408.1 |
| Parrya nudicaulis | flavonol synthase | HQ215409.1 |
| Parrya nudicaulis | flavonol synthase | HQ215403.1 |
| Parrya nudicaulis | flavonol synthase | HQ215388.1 |
| Arabidopsis lyrata | flavonol synthase 5 | XM_021022487.1 |
| Arabidopsis thaliana | flavonol synthase | EU287457.1 |

In one aspect, the gene that expresses iron oxidase is isolated from a yeast such as, for example, *Komagataella phaffii* (also known as *Pichia pastoris*). In another aspect, the gene that expresses iron oxidase is isolated from a bacterium of the *Acidithiobacillus* genus such as, for example, *A. ferrivorans* or *ferrooxidans*. In still another aspect, the gene that expresses iron oxidase is isolated from an insect such as a parasitic wasp or a fruit fly (e.g., *Drosophila* species *D. virilis*, *D. serrata*, *D. miranda*, *D. pseudoobscura*, *D. willistoni*, *D. mojavensis*, *D. erecta*, *D. persimilis*, *D. rhopaloa*, *D. eugracilis*, *D. biarmipes*, or *D. grimshawi*). In a different aspect, the gene that expresses iron oxidase is isolated from an Apicomplexan parasite such as, for example, *Eimeria necatrix*, *E. mitis*, or *E. maxima*. In still another aspect, the gene that expresses iron oxidase is isolated from a fungus. In a further aspect, the gene that expresses iron oxidase has SEQ ID NO. 10 or at least 70% homology thereof, at least 75% homology thereof, at least 80% homology thereof, at least 85% homology thereof, at least 90% homology thereof, or at least 95% homology thereof. In a still further aspect, the gene that expresses iron oxidase is a longer sequence that incorporates SEQ ID NO. 10. In one aspect, the gene that expresses iron oxidase can be isolated from *Acidithiobacillus ferrivorans* and can be found in GenBank with accession number AEM49324.1.

Other sequences expressing iron oxidase or related or homologous genes can be identified in a database such as, for example, GenBank. In one aspect, sequences useful herein include those with the GI numbers listed in Table 7.

TABLE 7

Iron Oxidase Genes

| Source Organism | Sequence Description | GI Number |
|---|---|---|
| Acidithiobacillus ferrivorans | genomic DNA | LT841305.1 |
| Acidithiobacillus ferrivorans | genomic DNA | CP002985.1 |
| Acidithiobacillus sp. NU-1 | high potential iron-sulfur protein | LC115034.1 |
| Acidithiobacillus ferrivorans | high potential iron-sulfur protein | KC533886.1 |
| Acidithiobacillus ferrooxidans | genomic DNA | CP001219.1 |
| Acidithiobacillus ferrooxidans | genomic DNA | CP001132.1 |
| Acidithiobacillus ferrooxidans | putative cytochrome C1 and hip gene (high-redox potential iron-sulfur protein) | AJ320262.1 |
| Acidithiobacillus ferrooxidans | extracellular iron oxidase gene | KP202695.1 |
| Acidithiobacillus ferrooxidans | high potential iron-sulfur protein | AJ621387.2 |
| Acidithiobacillus ferrooxidans | high potential iron-sulfur protein | AJ621388.2 |
| Acidithiobacillus ferrooxidans | high potential iron-sulfur protein | AJ621389.1 |
| Acidithiobacillus ferrooxidans | high potential iron-sulfur protein | FN688768.1 |
| Acidithiobacillus ferrooxidans | high potential iron-sulfur protein | AJ621386.2 |
| Drosophila virilis | genomic DNA | XM_002051073.2 |
| Drosophila serrata | myc protein | XM_020952897.1 |
| Komagataella phaffii | genomic DNA | CP014716.1 |
| Komagataella phaffii | genomic DNA | CP014709.1 |
| Eimeria necatrix | hypothetical protein | XM_013579952.1 |
| Capsaspora owczarzaki | hypothetical protein | XM_004365711.2 |
| Komagataella phaffii | GS115 subunit of TFIID and SAGA complexes | XM_002491459.1 |
| Pichia pastoris | genomic DNA | FN392320.1 |
| Mus pahari | zinc finger homeobox 3 | XM_021220667.1 |
| Amphimedon queenslandica | serine/threonine-protein phosphatase 6 | XM_019994058.1 |
| Harpegnathos saltator | hypothetical protein | XM_019844601.1 |
| Aptenodytes forsteri | mediator complex subunit 12 | XM_019474213.1 |
| Drosophila miranda | CREBRF homolog variant X2 | XM_017287684.1 |
| Drosophila miranda | CREBRF homolog variant X1 | XM_017287683.1 |
| Drosophila pseudoobscura pseudoobscura | uncharacterized protein | XM_003736903.2 |
| Drosophila pseudoobscura pseudoobscura | uncharacterized protein | XM_001360048.3 |
| Drosophila willistoni | uncharacterized protein | XM_002071081.2 |
| Drosophila mojavensis | uncharacterized protein | XM_002010833.2 |
| Drosophila erecta | uncharacterized protein | XM_001976758.2 |
| Trichogramma pretiosum | basic salivary proline-rich protein 1-like variant X2 | XM_014377751.1 |
| Trichogramma pretiosum | basic salivary proline-rich protein 1-like variant X1 | XM_014377750.1 |
| Eimeria mitis | hypothetical protein | XM_013498177.1 |
| Eimeria mitis | hypothetical protein | XM_013497016.1 |
| Eimeria mitis | hypothetical protein | XM_013496741.1 |
| Eimeria mitis | hypothetical protein | XM_013495477.1 |
| Eimeria mitis | hypothetical protein | XM_013494226.1 |
| Eimeria maxima | hypothetical protein | XM_013477429.1 |
| Sordaria macrospora | k-hell hypothetical protein | XM_003345950.1 |
| Drosophila persimilis | uncharacterized protein | XM_002019945.1 |
| Grapholita molesta | microsatellite sequence | KX711552.1 |
| Drosophila rhopaloa | BEACH domain-containing protein IvsC, variant X5 | XM_017123494.1 |
| Drosophila rhopaloa | BEACH domain-containing protein IvsC, variant X4 | XM_017123493.1 |
| Drosophila rhopaloa | BEACH domain-containing protein IvsC, variant X3 | XM_017123492.1 |
| Drosophila rhopaloa | BEACH domain-containing protein IvsC, variant X2 | XM_017123491.1 |
| Drosophila rhopaloa | BEACH domain-containing protein IvsC, variant X1 | XM_017123490.1 |
| Drosophila eugracilis | insulin-like receptor | XM_017208806.1 |
| Drosophila biarmipes | putative uncharacterized protein | XM_017091657.1 |
| Acyrthosiphon pisum | Krueppel-like factor 6 | XM_003240097.3 |
| Neodiprion lecontei | uncharacterized protein | XM_015666154.1 |
| Trichogramma pretiosum | putative uncharacterized protein | XM_014364909.1 |
| Eimeria necatrix | hypothetical protein | XM_013582418.1 |
| Eimeria mitis | hypothetical protein | XM_013497930.1 |
| Eimeria mitis | hypothetical protein | XM_013496691.1 |
| Eimeria mitis | hypothetical protein | XM_013496040.1 |
| Eimeria maxima | hypothetical protein | XM_013478862.1 |
| Enterobius vermicularis | genomic DNA | LM416156.1 |
| Drosophila persimilis | uncharacterized protein | XM_002024972.1 |
| Drosophila grimshawi | uncharacterized protein | XM_001990136.1 |

In one aspect, the gene that expresses zinc oxidase is isolated from bacteria. In a further aspect, the bacteria are *Streptomyces* bacteria such as, for example, *S. lincolnensis*, *S. collinus*, *S. avermitilis*, *S. parvulus*, *S. ambofaciens*, *S. scabiei*, *S. davawensis*, *S. pluripotens*, *S. pactum*, *S. puniciscabiei*, *S. griseochromogenes*, *S. incarnatus*, *S. aureocfaciens*, *S. reticuli*, *S. hygroscopicus*, *S. fulvissimus*, *S. katrae*, *S. silaceus*, *S. venezuelae*, or *S. albireticuli*. In another aspect, the bacteria are *Clostridium* bacteria such as *C. sporogenes* or *C. botulinum*. In still another aspect, the bacteria are selected from one of the following genera: *Polaribacter, Kitasatospora, Actinobacteria, Azospirillum, Collimonas*, or *Micromonospora*. In a different aspect, the gene that expresses zinc oxidase is isolated from algae. In one aspect, the algal species is, for example, *Guillardia theta*. In an alternative aspect, the gene that expresses zinc oxidase is isolated from fish. In one aspect, the fish is salmon. In a further aspect, the gene that expresses zinc oxidase has SEQ ID NO. 11 or at least 70% homology thereof, at least 75% homology thereof, at least 80% homology thereof, at least 85% homology thereof, at least 90% homology thereof, or at least 95% homology thereof. In a still further aspect, the gene that expresses zinc oxidase is a longer sequence that incorporates SEQ ID NO. 11. In one aspect, the gene that expresses zinc oxidase is isolated from *Streptomyces zinciresistens* and can be found in GenBank with GI number EGX59011.1.

Other sequences expressing zinc oxidase or related or homologous genes can be identified in a database such as, for example, GenBank. In one aspect, sequences useful herein include those with the GI numbers listed in Table 8.

TABLE 8

Zinc Oxidase Genes

| Source Organism | Sequence Description | GI Number |
|---|---|---|
| Streptomyces lincolnensis | genomic DNA | CP016438.1 |
| Streptomyces sp. 4F | genomic DNA | CP013142.1 |
| Streptomyces collinus | genomic DNA | CP006259.1 |

TABLE 8-continued

Zinc Oxidase Genes

| Source Organism | Sequence Description | GI Number |
|---|---|---|
| *Streptomyces avermitilis* | genomic DNA | BA000030.4 |
| *Streptomyces* sp. 3124.6 | genomic DNA | LT670819.1 |
| *Streptomyces parvulus* | genomic DNA | CP015866.1 |
| *Streptomyces ambofaciens* | genomic DNA | CP012949.1 |
| *Streptomyces ambofaciens* | genomic DNA | CP012382.1 |
| *Streptomyces scabiei* | genomic DNA | FN554889.1 |
| *Streptomyces davawensis* | genomic DNA | HE971709.1 |
| *Polaribacter* sp. SA4-12 | genomic DNA | CP019334.1 |
| *Streptomyces* sp. CdTB01 | genomic DNA | CP013743.1 |
| *Kitasatospora setae* | genomic DNA | AP010968.1 |
| *Streptomyces pluripotens* | genomic DNA | CP021080.1 |
| *Streptomyces pactum* | genomic DNA | CP019724.1 |
| *Polaribacter* sp. Hel1 | genomic DNA | LT629794.1 |
| *Streptomyces* sp. TLI | genomic DNA | LT629775.1 |
| *Streptomyces pactum* | genomic DNA | CP016795.1 |
| *Streptomyces puniciscabiei* | genomic DNA | CP017248.1 |
| *Streptomyces griseochromogenes* | genomic DNA | CP016279.1 |
| *Streptomyces incarnatus* | genomic DNA | CP011497.1 |
| *Streptomyces aureofaciens* | genomic DNA | CP020567.1 |
| *Streptomyces* sp. S10(2016) | genomic DNA | CP015098.1 |
| *Streptomyces reticuli* | genomic DNA | LN997842.1 |
| *Actinobacteria bacterium* IMCC25003 | genomic DNA | CP015603.1 |
| *Polaribacter* sp. KT25b | genomic DNA | LT629752.1 |
| *Streptomyces hygroscopicus* subsp. *limoneus* | genomic DNA | CP013219.1 |
| *Streptomyces* sp. Mg1 | genomic DNA | CP011664.1 |
| *Azospirillum brasiliense* | genomic DNA | CP007796.1 |
| *Streptomyces hygroscopicus* subsp. *jinggangensis* | genomic DNA | CP003720.1 |
| *Streptomyces hygroscopicus* subsp. *jinggangensis* | genomic DNA | CP003275.1 |
| *Collimonus arenae* | genomic DNA | CP009962.1 |
| *Polaribacter* sp. MED152 | genomic DNA | CP004349.1 |
| *Streptomyces* sp. S8 | genomic DNA | CP015362.1 |
| *Micromonospora echinofusca* | genomic DNA | LT607733.1 |
| *Streptomyces* sp. PBG53 | genomic DNA | CP011799.1 |
| *Streptomyces fulvissimus* | genomic DNA | CP005080.1 |
| *Streptomyces katrae* | genomic DNA | CP020042.1 |
| *Streptomyces silaceus* | genomic DNA | CP015588.1 |
| *Streptomyces venezuelae* | genomic DNA | CP018074.1 |
| *Salmo solar* | calmodulin | XM_014213459.1 |
| *Streptomyces venezuelae* | genomic DNA | FR845719.1 |
| *Salmo solar* | calmodulin | BT059493.1 |
| *Salmo solar* | calmodulin | BT045544.1 |
| *Streptomyces albireticuli* | genomic DNA | CP021744.1 |
| *Streptomyces* sp. 3211 | genomic DNA | CP020039.1 |
| *Clostridium sporogenes* | genomic DNA | CP011663.1 |
| *Clostridium sporogenes* | genomic DNA | CP009225.1 |
| *Clostridium botulinum* | genomic DNA | CP006902.1 |
| *Guillardia theta* | hypothetical protein | XM_005830304.1 |

In one aspect, the DNA constructs disclosed herein include a reporter protein. In a further aspect, the reporter protein is a yellow fluorescent reporter protein. In a still further aspect, the gene that expresses the yellow fluorescent reporter protein has SEQ ID NO. 12 or at least 70% homology thereof, at least 75% homology thereof, at least 80% homology thereof, at least 85% homology thereof, at least 90% homology thereof, or at least 95% homology thereof.

Exemplary methods for producing the DNA constructs described herein are provided in the Examples. Restriction enzymes and purification techniques known in the art can be used to prepare the DNA constructs. After the vector incorporating the DNA construct has been produced, it can be incorporated into host cells using the methods described below.

Biological Devices

In one aspect, a "biological device" is formed when a microbial cell is transfected with the DNA construct described herein. The biological devices are generally composed of microbial host cells, where the host cells are transformed with a DNA construct described herein.

In one aspect, the DNA construct is carried by the expression vector into the cell and is separate from the host cell's genome. In another aspect, the DNA construct is incorporated into the host cell's genome. In still another aspect, incorporation of the DNA construct into the host cell enables the host cell to produce UV-protective proteins.

The host cells as referred to herein include their progeny, which are any and all subsequent generations formed by cell division. It is understood that not all progeny may be identical due to deliberate or inadvertent mutations. A host cell may be "transfected" or "transformed," which refers to a process by which exogenous nucleic acid is transferred or introduced into the host cell. A transformed cell includes the primary subject cell and its progeny. The host cells can be naturally-occurring cells or "recombinant" cells. Recombinant cells are distinguishable from naturally-occurring cells in that naturally-occurring cells do not contain heterologous nucleic acid sequences introduced using molecular biology techniques. In one aspect, the host cell is a prokaryotic cell such as, for example, *Escherichia coli*. In other aspects, the host cell is a yeast such as, for example, *Saccharomyces cerevisiae*. Host cells transformed with the DNA construct described herein are referred to as biological devices.

The DNA construct is first delivered into the host cell. This delivery can be accomplished in vitro, using well-developed laboratory procedures for transforming cell lines. Transformation of bacterial cell lines can be achieved using a variety of techniques. One method involves calcium chloride. The exposure to the calcium ions renders the cells able to take up the DNA construct. Another method is electroporation. In this technique, a high-voltage electric field is applied briefly to cells, producing transient holes in the cell membrane through which the vector containing the DNA construct enters. Exemplary procedures for transforming yeast and bacteria with specific DNA are provided in the Examples. In certain aspects, two or more types of DNA can be incorporated into the host cells. Thus, different metabolites can be produced from the same plant at enhanced rates.

Once the DNA construct has been incorporated into the host cell, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth promoting substances. The addition of peptone provides a readily available source of nitrogen and carbon. A variety of other carbon sources are contemplated, including, but not limited to: monosaccharides such as glucose and fructose, disaccharides such as lactose and sucrose, oligosaccharides, polysaccharides such as starch, and mixtures thereof. Unpurified mixtures extracted from feedstocks are also contemplated and can include molasses, barley malt, and related compounds and compositions. Other glycolytic and tricarboxylic acid cycle intermediates are also contemplated as carbon sources, as are one-carbon substrates such as carbon dioxide and/or methanol in the cases of compatible organisms. The carbon source utilized is limited only by the particular organism being cultured.

Furthermore, the use of different media results in different growth rates and different stationary phase densities. Secondary metabolite production is highest when cells are in stationary phase. A rich media results in a short doubling time and higher cell density at stationary phase. Minimal media results in slow growth and low final cell densities.

Efficient agitation and aeration increase final cell densities. A skilled artisan will be able to determine which type of media is best suited to culture a particular species and/or strain of host cell.

Culturing or fermenting host cells may be accomplished by any technique known in the art. In one aspect, batch fermentation can be conducted. In batch fermentation, the composition of the culture medium is set at the beginning of culturing and the system is closed to future artificial alterations. In some aspects, a limited form of batch fermentation can be carried out, wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial host cells are immobilized on a substrate. Fermentation can be carried out on any scale and may include methods in which literal "fermentation" is carried out as well as other culture methods that are non-fermentative.

UV-Resistant Microbes

In one aspect, a yeast or bacterium, particularly a beneficial yeast or bacterium such as one used in a fermentation process, can be engineered to be UV-resistant by transforming or transfecting the yeast or bacteria with a nucleic acid able to express a protein up-regulated by UV exposure. In one aspect, the nucleic acids can be under the control of a constitutive promoter. In another aspect, the nucleic acids can be under control of a UV-inducible promoter. In some aspects, when the yeast or bacterium needs to perform another function, such as fermentation, the nucleic acids can be under control of UV-inducible promoters so as not to impede the other function when UV protection is not required.

In a further aspect, UV-resistant microbes can be used in fermentation processes, such as the production of alcohol or fuel ethanol, or in the production of chemical and pharmaceutical products, including biological drug products.

Preparation of UV-Protective Extracts

In one aspect, provided herein are UV-protective extracts produced by the biological devices disclosed herein. In one aspect, the present UV-protective microbial extracts are able to wholly or partially block the passage of UV radiation.

The extent to which UV radiation is blocked can depend on a variety of factors including the particular microbe used, the amount of extract applied, and the formulation of the extract.

In a further aspect, the UV protective extract can be prepared by exposing a culture of a biological device such as those disclosed herein to UV radiation, then extracting components from the culture. In one aspect, the components are extracted via centrifugation. In another aspect, the culture of the biological device is applied to a subject or surface after UV irradiation and without extraction. The UV radiation can be of any wavelength, but in one aspect, it can be shortwave radiation (i.e., ultraviolet C having a wavelength of approximately 100 to 280 nm), medium wave radiation (i.e., ultraviolet B, having a wavelength of approximately 280 to 315 nm), or longwave radiation (i.e., ultraviolet A having a wavelength of 315 to 400 nm). In one aspect, the culture of the biological device can be irradiated with a 254 nm shortwave UV source. In another aspect, the culture of the biological device can be irradiated with a 365 nm longwave UV source. In still another aspect, the culture of the biological device can be irradiated with both a 254 nm and a 365 nm UV source. In yet another aspect, the culture of the biological device can be irradiated with a natural UV source such as, for example, the sun, providing a range of wavelengths for irradiation.

In one aspect, culture of the biological device may proceed until the culture is dense, but not so dense as to trigger deleterious responses (e.g., a response triggered by lack of a food source) and not so dense as to prevent UV radiation from reaching a substantial portion of cells in the culture. Once the desired culture density has been reached, the culture can then be irradiated with UV radiation. Prior to irradiation, in one aspect, the culture is transferred to one or more vessels designed to allow a substantial portion of the biological device to be irradiated.

In one aspect, the irradiation continues for the length of time needed to induce a radiation response in the biological devices and ends at or before a time at which a substantial portion of the biological devices are fatally irradiated. In a further aspect, the extract can be collected after exposing a culture of a biological device to UV irradiation for a period of time ranging from about 12 hours to about 72 hours, or about 12, 24, 36, 48, 60, or 72 hours. In an alternative aspect, the biological devices may continue to be cultured for a time after UV exposure at least sufficient to allow some radiation response in the biological devices. In a further aspect, if irradiation did not cause death of a substantial portion of the organisms in culture, culture may continue until the radiation response has ceased in a majority of the organisms.

In one aspect, radiation response can include upregulation of at least one of the following: a hexokinase, a heat shock protein, an alcohol dehydrogenase, transferrin, a flavonol synthase, a zinc oxidase, an iron oxidase, or a combination thereof.

It will be understood that up-regulation or down-regulation of one or more of these proteins may not be directly responsible for UV-protective properties, such that increased or decreased amounts of these proteins in the extract may have little or no effect on the UV-protective properties of the extract. Further in this aspect, up-regulation or down-regulation of one of these proteins may have downstream effects that ultimately produce a UV-protective effect. In an alternative aspect, up-regulation or down-regulation of one or more of these proteins may be directly responsible for the UV-protective properties of the extract.

In one aspect, the extract is prepared in a manner able to isolate at least one UV-protective component. In some aspects, the extract can include centrifuged bacterial or yeast components. In one aspect, the extract is formulated at a variety of concentrations in any acceptable carrier to allow its use for a particular purpose. In some aspects, the extract is formulated in an evaporable carrier, such as water or alcohol, to allow the extract to dry on the surface of the material to be protected from UV radiation. In an alternative aspect, the extract is formulated in a lotion, gel, oil, or cream for application to human or animal skin.

In one aspect, the extract can be prepared by centrifuging the culture of biological devices in a manner able to precipitate most proteins, including UV-resistant and/or UV-protective proteins, then discarding the supernatant while retaining the pellet as the extract. Further in this aspect, the pellet can be used as-is or dried. Still further in this aspect, the pelleted material can be diluted to a given concentration using any acceptable carrier, such as water, alcohol, lotion, gel, oil, or cream. In one aspect, the carrier is non-denaturing. In an alternative aspect, the carrier is denaturing. In a still further aspect, the carrier also includes materials to inhibit further bacterial growth and/or protein degradation.

In an alternative aspect, the supernatant contains UV-protective compounds and is not discarded. In yet another aspect, the UV-protective and/or UV-resistant compounds and proteins are extracted by another method known in the art for isolating proteins and/or metabolites.

In a further aspect, the biological device culture may not be pelletized but instead may be killed, for example by lysis or exposure to lethal levels of UV radiation, and the culture medium can be used as-is or in an evaporated form. Further in this aspect, materials to inhibit further microorganism growth and/or protein degradation can also be introduced.

In another aspect, cells from any of the cultures described above can be isolated with or without extraction and/or lysis and used in wet or dry form.

In another aspect, isolated proteins from the biological device culture can be used in place of a more general extract to produce a UV-protective effect. Such proteins can be isolated by techniques known in the art.

Applications of UV-Protective Extracts

The extract may be applied to any material that may benefit from a reduction in UV radiation. The exact formulation of the extract plus any carriers can be adjusted based on the desired use. In one aspect, the extract is formulated with only non-toxic components if it is to be used on a human or animal or with another microorganism, such as in a fermentation process or on an agricultural product. In another aspect, the extract can be mixed with other substances to provide UV-protective properties to the overall composition. In still another aspect, if coated on the material to be protected, the extract itself can be covered with a further protective coating to project, for example, against mechanical wear and damage.

In the case when the extract is applied to the surface of an article, it can be applied using techniques known in the art such spraying or coating. In other aspects, the extract can be intimately mixed with a substance or material that ultimately produces the article. For example, the extract can be mixed with molten glass so that the extract is dispersed throughout the final glass product.

In one aspect, the extract is formulated or applied in such a manner as to block approximately 50%, 60%, 70%, 80%, 90%, 95%, or 99% of the UV radiation that encounters the extract, where any value can be a lower and upper end-point of a range (e.g., 60% to 95%). In a further aspect, the extract can also be formulated to block these percentages of particular UV wavelengths, or, more generally, to block these percentages of UVA, UVB, or UVC radiation.

Extracts according to the present disclosure can be used for a variety of purposes. These purposes include, but are not limited to, the following:

1. blocking UV radiation or other types of radiation;
2. protecting human skin against damage and/or skin cancer induced by UV radiation or other types of radiation;
3. protecting against side effects of radiation used in cancer treatments;
4. protecting animals from deleterious effects of UV radiation or other radiation;
5. protecting plastic, fiberglass, glass, rubber, or other solid surfaces from UV radiation or other radiation;
6. providing a UV radiation screen or screen for other types of radiation;
7. protecting astronauts and/or other persons or organisms as well as equipment during space trips;
8. enhancement of industrial fermentation processes or other processes requiring energy by allowing the use of UV radiation in connection with the process to supply additional energy and thus to increase the ultimate energy-requiring output of the cells without substantially killing the fermenting organism;
9. protection of experimentation, fermentation, biochemical, and/or biological processes under the presence of UV radiation, for example in extraterrestrial conditions such as on the moon or Mars; and
10. protection of agricultural plants, particularly agricultural plants in which the revenue-producing part of the plant is above ground, such as fruits, vine vegetables, beans and peas, and leaf vegetables.

In one particular embodiment, an extract prepared according to the procedure described above, can be applied to an agricultural plant. In one aspect, the plant can be one that produces fruit or vegetable, such as, for example, a watermelon or a tomato. Further in this aspect, the extract can be applied during at least a part of the plant's growth to increase the amounts of one or more nutrients of the fruit or vegetable, such as a vitamin, mineral, or other recommended dietary component. In one specific aspect, the amount of lycopene can be increased (which may be accompanied by a decrease in carotene or other less-valuable nutrients formed by competing pathways). In another aspect, the amount of a flavor-enhancing component, such as glucose, can be increased. Further in this aspect, an increase in glucose can help protect against water loss.

In one aspect, the extract can be applied for about 25%, 50%, 75%, 90%, 95%, or 99% of the fruit or vegetable's on-plant life, where the on-plant life includes the time span from the formation of a separate body that will constitute the fruit or vegetable (in some aspects, excepting flowers) until the fruit or vegetable is harvested. In one aspect, the extract can be first applied when the fruit or vegetable is sufficiently large to no longer be substantially protected from UV radiation by leaves. In another aspect, the extract can first be applied five days, one week, or two weeks prior to harvest. Further in this aspect, application at this later stage can be particularly useful with fruits or vegetables in which an increase in a nutrient or flavor-enhancing component can be obtained by protecting the fruit or vegetable from UV radiation later in its on-plant life.

In one aspect, the extract can be applied once or multiple times to each fruit or vegetable. In another aspect, it can be applied weekly, or it can be reapplied after the fruit or vegetable is exposed to rain or after a turning process. In another aspect, the agricultural plant can be another food crop that grows above ground and is exposed to natural UV radiation, wherein the agricultural product produced can be a fruit, leaf, seed, flower, grain, nut, stem, vegetable, or mushroom.

In another aspect, it is desirable for agricultural plants that do not produce parts typically consumed by humans to be protected from UV irradiation. In a further aspect, these other agricultural plants can includes sources of fibers such as, for example, cotton and linen (flax), of cork, of wood or lumber, of feedstocks for producing ethanol or biodiesel (including, but not limited to, sugar beet, sugarcane, cassava, sorghum, corn, wheat, oil palm, coconut, rapeseed, peanut, sunflower, soybean, and the like), of animal feedstocks or fodder, or of decorative or horticultural plants.

In one aspect, any part of the plant can be coated, including, but not limited to, the part of the plant that is collected during harvest. In an alternative aspect, the harvested part of the plant is not coated, but another part can be coated with the extracts disclosed herein. In addition to the aspects already described, in one aspect, coating a plant with the extracts described herein can prolong the life of the plant, increase production capacity of a desired product, can increase the growth rate of the plant relative to an untreated plant of the same type, can increase production of a desired metabolite that might otherwise decrease due to UV-induced stress, can increase yield of a crop of such plants, and the like.

In a further aspect, application can be accomplished with a commercial sprayer. In another aspect, application can be only on the upper portions of the fruit or vegetable, which are exposed to substantially greater amounts of UV radiation than the lower portions of the fruit or vegetable.

In another aspect, provided herein is a pharmaceutical composition containing the extracts produced by the biological devices described herein. In one aspect, the pharmaceutical composition can be applied to a subject, wherein the subject is exposed to radiation. In one aspect, the radiation is applied as a strategy to treat cancer. In another aspect, the pharmaceutical composition is used to prevent radiation-induced cellular and DNA damage. In another aspect, dosage ranges of the extract in the pharmaceutical composition can vary from 0.01 g extract/mL of pharmaceutical composition to 1 g extract/mL of pharmaceutical composition, or can be 0.01, 0.02, 0.025, 0.05, 0.075, or 1 g extract/mL of pharmaceutical composition. In an alternative aspect, provided herein is a cosmetic composition containing the extracts produced by the biological devices described herein. Further in this aspect, the cosmetic composition can be a cleanser, lotion, cream, shampoo, hair treatment, makeup, lip treatment, nail treatment, or related composition. In still a further aspect, the compositions containing the extracts can have both pharmaceutical and cosmetic applications. In yet another aspect, the compositions containing the extracts can be used in veterinary medicine.

The cosmetic compositions can be formulated in any physiologically acceptable medium typically used to formulate topical compositions. The cosmetic compositions can be in any galenic form conventionally used for a topical application such as, for example, in the form of dispersions of aqueous gel or lotion type, emulsions of liquid or semi-liquid consistency of the milk type, obtained by dispersing a fatty phase in an aqueous phase (O/W) or vice versa (W/O), or suspensions or emulsions of soft, semi-solid or solid consistency of the cream or gel type, or alternatively multiple emulsions (W/O/VV or O/W/O), microemulsions, vesicular dispersions of ionic and/or non-ionic type, or wax/aqueous phase dispersions. These compositions are prepared according to the usual methods.

The cosmetic compositions can also contain one or more additives commonly used in the cosmetics field, such as emulsifiers, preservatives, sequestering agents, fragrances, thickeners, oils, waxes or film-forming polymers. In one aspect, in any of the above scenarios, the pharmaceutical, cosmetic, or veterinary composition also includes additional UV-protective compounds or UV-blocking agents such as, for example, zinc oxide, titanium dioxide, carotenoids, oxybenzone, octinoxate, homosalate, octisalate, octocrylene, avobenzone, or a combination thereof.

In one aspect, the composition is a sunscreen. A sunscreen can be formulated with any of the extracts produced herein. In addition to the extract, the sunscreen in certain aspects can be formulated with one or more UV-protective compounds or UV-blocking agents listed above. The sunscreen can be formulated as a paste, lotion, cream, aerosol, or other suitable formulations for topical use. In certain aspects, the sunscreen can be formulated as a transparent composition.

In one aspect, the cosmetic composition can be a film composed of the extracts produced herein that can be directly applied to the skin. For example, the film can be composed of a biocompatible material such as a protein or oligonucleotide, where the extract is coated on one or more surfaces of the film or, in the alternative dispersed throughout the film. For example, the film can be composed of DNA. In this application, the films can be used as a wound covering and provide protection from UV photodamage. The films can also be prepared so that they are optically transparent. Here, it is possible to view the wound without removing the covering and exposing the wound. The films can also include other components useful in cosmetic applications such as, for example, compounds to prevent or reduce wrinkles.

In one aspect, the pharmaceutical, cosmetic, or veterinary compositions described herein are applied to subjects. In one aspect, the subject is a human, another mammal, or a bird. In a further aspect, the mammal is a pet such as a dog or cat or is livestock such as horses, goats, cattle, sheep, and the like. In an alternative aspect, the bird is a pet bird or is poultry such as, for example, a chicken or turkey. In any of these aspects, the compositions can be applied to skin, fur, feathers, wool, hooves, horns, or hair as appropriate and applicable.

In another aspect, provided herein is a paint, dye, stain, or ink containing the UV-protective and/or UV-resistant extract disclosed herein. In one aspect, there are several benefits to having a paint that is resistant to UV irradiation. In a further aspect, imparting UV resistance to a paint slows or stops photodegradation, bleaching, or color fading. In another aspect, a paint with UV resistance prevents chemical modification of exposed paint surfaces. Further in this aspect, chemical modification of exposed paint surfaces includes change in finish, structural changes in binders, flaking, chipping, and the like. In one aspect, the paint provided herein resists these changes.

In still another aspect, provided herein is an article coated with the extracts disclosed herein. In one aspect, the article is made of glass, plastic, metal, wood, fabric, or any combination thereof. In one aspect, the article is a construction material such as, for example, steel, concrete or cement, brick, wood, window or door glass, fiberglass, siding, wallboard, a flooring material, masonry, mortar, grout, stone, artificial stone, stucco, shingles, roofing materials, and the like. In an alternative aspect, the material is an aeronautical or aerospace material such as, for example, the metal or metal alloy body of an aircraft or spacecraft, paint on the body of an aircraft or spacecraft, glass windows on an aircraft or spacecraft, carbon fiber composite, titanium or aluminum, a ceramic heat absorbing tile, and the like. In still another aspect, the article is a fabric article such as, for example, clothing, drapes, outdoor upholstery, a tent or outdoor pavilion, a flag or banner, or the like. In another aspect, the extract can be applied to the article to fine artwork, solid pieces (e.g., vases), and historical documents in order to preserve them. In another aspect, the extract can be applied to outdoor signs such as highway billboards and advertising.

In other aspects, the extract can be incorporated within or throughout the article. In one aspect, the extract can be mixed with molten glass to produce glass article that are UV resistant such as, for example, sunglasses, car windshields, window glass, and eyeglasses. In another aspect, the glass article can be a bottle for storing a beverage or food container in order to increase the shelf-life of the beverage or food. It is contemplated that the extract can be applied externally to the glass articles as well.

In another aspect, the extract can be mixed with fiberglass or plastics in order to reduce negative effects to aircraft, watercraft, boats, jet skis, decking, house siding, motor homes, sunroofs, and moon roofs that are constantly exposed to UV radiation. It is contemplated that the extract can be applied externally to the fiberglass or plastic articles as well.

In another aspect, the extract can be mixed with rubber, silicon, or latex used to make a variety of articles such as water hoses, tires, and the like. It is contemplated that the extract can be applied externally to the rubber, silicone, or latex articles as well.

In another aspect, the extract can be mixed with foams used to make a variety of articles such as automotive dashboard padding, seat cushions, and the like. It is contemplated that the extract can be applied externally to the foam articles as well.

In another aspect, the extracts described herein can be incorporated into an optical film. In one aspect, the extract is applied to at least one surface of the film. In another aspect, the extract can be dispersed throughout the film. The film can be transparent, translucent or opaque. The film can be composed of, but not limited to, polyolefin resin, such as polyethylene (PE) or polypropylene (PP); polyester resin, such as polyethylene terephthalate (PET); polyacrylate resin, such as polymethyl (meth)acrylate (PMMA); polycarbonate resin; polyurethane resin or a mixture thereof. The optical film can be applied to any substrate where it is desirable to reduce or prevent UV exposure or damage. For example, the optical film can be applied to windows to reduce or prevent UV radiation from entering a structure (e.g., building, vehicle, etc.).

In another aspect, provided herein is a method of reducing or preventing the exposure of an item to UV radiation by applying the extracts described herein to the item or incorporating the extract within/throughout the article. Further in this aspect, "reducing" is defined relative to an untreated control. That is, if two like items are exposed to equal amounts of UV radiation for an equal amount of time, but one has been treated with the UV-resistant extracts and the other has not, and some objective response is measured (e.g., color fading, structural degradation, plant size or yield, etc.), the treated item will appear to have been exposed to a lower amount of UV (for example, the color of the treated item will have faded less and will remain closer to the original, or a treated plant will appear larger and more vigorous and will have a greater yield, etc.). In some aspects, treatment with the extracts disclosed herein will prevent UV exposure from occurring. As used herein, "prevent" indicates that a treated item will not be affected, changed, or altered by UV exposure.

In one aspect, the extract blocks from 50% to 100% of UV radiation from contacting the item. Further in this aspect, the extract blocks at least 50%, 55%, 60%, 65%, 70%, 75%, 80%, 85%, 90%, 95%, 99%, or 100% of UV radiation from contacting the item. In another aspect, the extract blocks from 50% to 100% of longwave UV radiation from contacting the item. Further in this aspect, the extract blocks at least 50%, 55%, 60%, 65%, 70%, 75%, 80%, 85%, 90%, 95%, 99%, or 100% of longwave UV radiation from contacting the item. In one aspect, the extract blocks from 50% to 100% of shortwave UV radiation from contacting the item. Further in this aspect, the extract blocks at least 50%, 55%, 60%, 65%, 70%, 75%, 80%, 85%, 90%, 95%, 99%, or 100% of shortwave UV radiation from contacting the item.

Depending upon the application, the extract can prevent or reduce damage cause by UV radiation from limited to extended periods of time. By varying the amount of extract that is applied as well as the number of times the extract is applied, the degree of UV protection can be varied. In certain aspects, it may be desirable for the article to be protected from UV damage for a short period of time then subsequently biodegrade.

In another aspect, the extracts produced herein can be used to reduce or prevent the growth of barnacles on boats and other water vehicles. In one aspect, the extract can be admixed with a paint that is typically applied to water vehicles, where the paint also includes chitosan. In one aspect, the chitosan can be acetylated to a specific degree of acetylation in order to enhance tissue growth during culturing as well as metabolite production. In one aspect, the chitosan is from 60% to about 100%, 70% to 90%, 75% to 85%, or about 80% acetylated. In one aspect, chitosan isolated from the shells of crab, shrimp, lobster, and/or krill is useful herein. The molecular weight of the chitosan can vary, as well. For example, the chitosan comprises about 3, 4, 5, 6, 7, 8, 9, 10, 11, 12, 13, 14, 15, 16, 17, 18, 19, or 20 glucosamine units and/or N-acetylglucosamine units. In another aspect, the chitosan includes 5 to 7 glucosamine units and/or N-acetylglucosamine units.

UV-Resistant Plants

In one aspect, provided herein is a plant that is resistant to UV radiation. As used herein, "plant" is used in a broad sense to include, for example, any species of woody, ornamental, crop, cereal, fruit, or vegetable plant, as well as photosynthetic green algae. "Plant" also refers to a plurality of plant cells that are differentiated into a structure that is present at any stage of a plant's development. Such structures include, but are not limited to, fruits, shoots, stems, leaves, flower petals, roots, tubers, corms, bulbs, seeds, gametes, cotyledons, hypocotyls, radicles, embryos, gametophytes, tumors, and the like. "Plant cell," "plant cells," or "plant tissue" as used herein refers to differentiated and undifferentiated tissues of plants including those present in any of the tissues described above, as well as to cells in culture such as, for example, single cells, protoplasts, embryos, calluses, etc. It is contemplated that any cell from which a fertile plant can be regenerated is useful as a recipient cell. Type I, Type II, and Type III callus can be initiated from tissue sources including, but not limited to, immature embryos, immature inflorescences, seedling apical meristems, microspores, and the like. Those cells that are capable of proliferating as callus are also useful herein. Methods for growing plant cells are known in the art (see U.S. Pat. No. 7,919,679).

In one aspect, plant calluses grown from 2 to 4 weeks can be used herein. The plant cells can be derived from plants varying in age. The plant cells can be contacted with the biological device in a number of different ways. In one aspect, the device can be added to a medium containing the plant cells. In another aspect, the device can be injected into the plant cells via syringe. The amount of device and the duration of exposure to the device can vary as well. In one aspect, the concentration of the device is about $10^3$, $10^4$, $10^5$, $10^6$, $10^7$, $10^8$, or $10^9$ cells/mL of water. In one aspect, when the host cell is a bacterium, the concentration of the device is $10^6$. In another aspect, when the host cell is yeast, the concentration of the device is $10^9$. Different volumes of the biological device can be used as well, ranging from 5 μL to 500 μL.

In certain aspects, any of the biological devices described above can be used in combination with a polysaccharide to enhance one or more physiological properties of the plant. In one aspect, the plant cells are first contacted with the biological device, then subsequently contacted with the polysaccharide. In another aspect, the plant cells are first contacted with the polysaccharide and subsequently contacted with the biological device. In a further aspect, the plant cells are simultaneously contacted with the polysaccharide and the biological device.

In one aspect, the polysaccharide includes chitosan, glucosamine (GlcN), N-acetylglucosamine (NAG), or any combination thereof. Chitosan is generally composed of glucosamine units and N-acetylglucosamine units and can be chemically or enzymatically extracted from chitin, which is a component of arthropod exoskeletons and fungal and microbial cell walls. In certain aspects, the chitosan can be acetylated to a specific degree of acetylation in order to enhance tissue growth during culturing as well as metabolite production. In one aspect, the chitosan is from 60% to about 100%, 70% to 90%, 75% to 85%, or about 80% acetylated. In one aspect, chitosan isolated from the shells of crab, shrimp, lobster, and/or krill is useful herein.

The molecular weight of the chitosan can vary, as well. For example, the chitosan comprises about 3, 4, 5, 6, 7, 8, 9, 10, 11, 12, 13, 14, 15, 16, 17, 18, 19, or 20 glucosamine units and/or N-acetylglucosamine units. In another aspect, the chitosan includes 5 to 7 glucosamine units and/or N-acetylglucosamine units. In one aspect, the chitosan is in a solution of water and acetic acid at less than 1% by weight, less than 0.75% by weight, less than 0.5% by weight, less than 0.25% by weight, or less than 0.1% by weight. In another aspect, the amount of chitosan that is applied to the plant cells is from 0.1% to 0.01% by weight, from 0.075% to 0.025% by weight, or is about 0.05% by weight. The polysaccharides used herein are generally natural polymers and thus present no environmental concerns. Additionally, the polysaccharide can be used in acceptably low concentrations.

The plant cells can be contacted with the polysaccharide using a number of techniques. In one aspect, the plant cells or reproductive organs (e.g., a plant embryo) can be cultured in agar and medium with a solution of the polysaccharide. In other aspects, the polysaccharide can be applied to a plant callus by techniques such as, for example, coating the callus or injecting the polysaccharide into the callus. In this aspect, the age of the callus can vary depending upon the type of plant. The amount of polysaccharide can vary depending upon, among other things, the selection and number of plant cells. The use of the polysaccharide in the methods described herein permits rapid tissue culturing at room temperature. Due to the ability of the polysaccharide to prevent microbial contamination, the tissue cultures can grow for extended periods of time ranging from days to several weeks. Moreover, tissue culturing with the polysaccharide can occur in the dark and/or light. As discussed above, the plant cells can be contacted with any of the biological devices described above. Thus, the use of the polysaccharides and biological devices described herein is a versatile way to culture and grow plant cells—and ultimately, plants of interest—with enhanced physiological properties.

In one aspect, a plant callus such as described above can be planted and allowed to grow and mature into a plant bearing fruit and leaves.

In a further aspect, provided herein is a plant grown by the process of contacting plant gamete cells, a plant reproductive organ, or a plant callus with the biological devices disclosed herein. Also provided herein is a method for producing such a plant. In one aspect, the method includes the steps of:

(a) contacting a plant callus with the biological device;
(b) culturing the plant callus; and
(c) growing a plant from the plant callus.

In some aspects, the plant callus is cultured with chitosan. In a further aspect, the chitosan is from 60%, 65%, 70%, 75%, 80%, 85%, 90%, 95%, or 100% acetylated and has 3, 4, 5, 6, 7, 8, 9, 10, 11, 12, 13, 14, 15, 16, 17, 18, 19, or 20 glucosamine units, N-acetylglucosamine units, or a combination thereof, where any value can be a lower and upper end-point of a range (e.g., 60% to 80% acetylation).

In another aspect, provided herein is a method for increasing the UV-resistance of a plant, the method involving growing a plant from plant cells that have been contacted with the biological devices disclosed herein. In one aspect, increased UV-resistance can be measured by growing plants from a treated and an untreated callus alongside one another and comparing UV-induced damage after a period of time. In a further aspect, an agricultural product harvested from a UV-resistant plant will also be more UV-resistant. Further in this aspect, for example, cotton from a cotton plant grown with the biological devices will be more UV-resistant than cotton grown from an untreated plant.

Solar Cells

In other aspects, zinc oxide produced by the devices herein can be used to produce solar cells. Solar cells typically include a thin film of semiconductive inorganic material. Examples of such materials include titanium oxide and zinc oxide. In one aspect, zinc oxide produced by the biological devices described herein can be used as the semiconductive layer in a solar cell. For example, any of the devices described herein that include a gene that expresses zinc oxidase (e.g., device in FIG. 3) can be used to produce zinc oxide that can subsequently be used to produce solar cells.

Examples

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions, e.g., component concentrations, desired solvents, solvent mixtures, temperatures, pressures, and other reaction ranges and conditions can be used to optimize the product purity and yield obtained from the described process. Only reasonable and routine experimentation will be required to optimize such processes and conditions.

The DNA construct was composed of genetic components described herein and assembled in plasmid vectors (e.g., pYES2 and pBSK). Sequences of genes and/or proteins with desired properties were identified in GenBank; these included a DXP synthase gene, a beta-carotene hydroxylase gene, and a lycopene epsilon-cyclase gene. Other genetic parts were also obtained for inclusion in the DNA constructs including, for example, promoter genes (e.g., GAL1 promoter), reporter genes (e.g., yellow fluorescent reporter protein), and terminator sequences (e.g., CYC1 terminator).

These genetic parts included restriction sites for ease of insertion into plasmid vectors.

The cloning of the DNA construct into the biological devices was performed as follows. Sequences of individual genes were amplified by polymerase chain reaction using primers that incorporated restriction sites at their 5' ends to facilitate construction of the full sequence to be inserted into the plasmid. Genes were then ligated using standard protocols to form an insert. The plasmid was then digested with restriction enzymes according to directions and using reagents provided by the enzyme's supplier (Promega). The complete insert, containing restriction sites on each end, was then ligated into the plasmid. Successful construction of the insert and ligation of the insert into the plasmid were confirmed by gel electrophoresis.

PCR was used to enhance DNA concentration using a Mastercycler Personal 5332 ThermoCycler (Eppendorf North America) with specific sequence primers and the standard method for amplification (Sambrook, J., E. F. Fritsch, and T. Maniatis, 1989, *Molecular Cloning: A Laboratory Manual*, $2^{nd}$ ed., Vol. 1, Cold Spring Harbor Laboratory Press: Cold Spring Harbor, N.Y.). Digestion and ligation were used to ensure assembly of DNA synthesized parts using restriction enzymes and reagents (PCR master mix of restriction enzymes: XhoI, KpnI, XbaI, EcoRI, BamHI, and HindIII, with alkaline phosphatase and quick ligation kit, all from Promega). DNA was quantified using a NanoVue spectrophotometer (GE Life Sciences) and a standard UV/Visible spectrophotometer using the ratio of absorbances at 260 nm versus 280 nm. In order to verify final ligations, DNA was visualized and purified via electrophoresis using a Thermo EC-150 power supply.

The DNA construct was made with gene parts fundamental for expression of sequences such as, for example, ribosomal binding sites, native and constitutive promoters, reporter genes, and transcriptional terminators or stops. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. The DNA constructs in FIGS. 1-3 were assembled using the techniques above.

After the vector comprising the DNA construct has been produced, the resulting vector can be incorporated into the host cells using the methods known in the art (e.g., Gietz, R. D. and R. H. Schiestl, 2007, Nature Protocols, "Quick and easy yeast transformation using the LiAc/SS carrier DNA/PEG method," Vol. 2, 35-37, doi:10.1038/nprot.2007.14).

Production of Anti-UV Extract

Figure 1B:
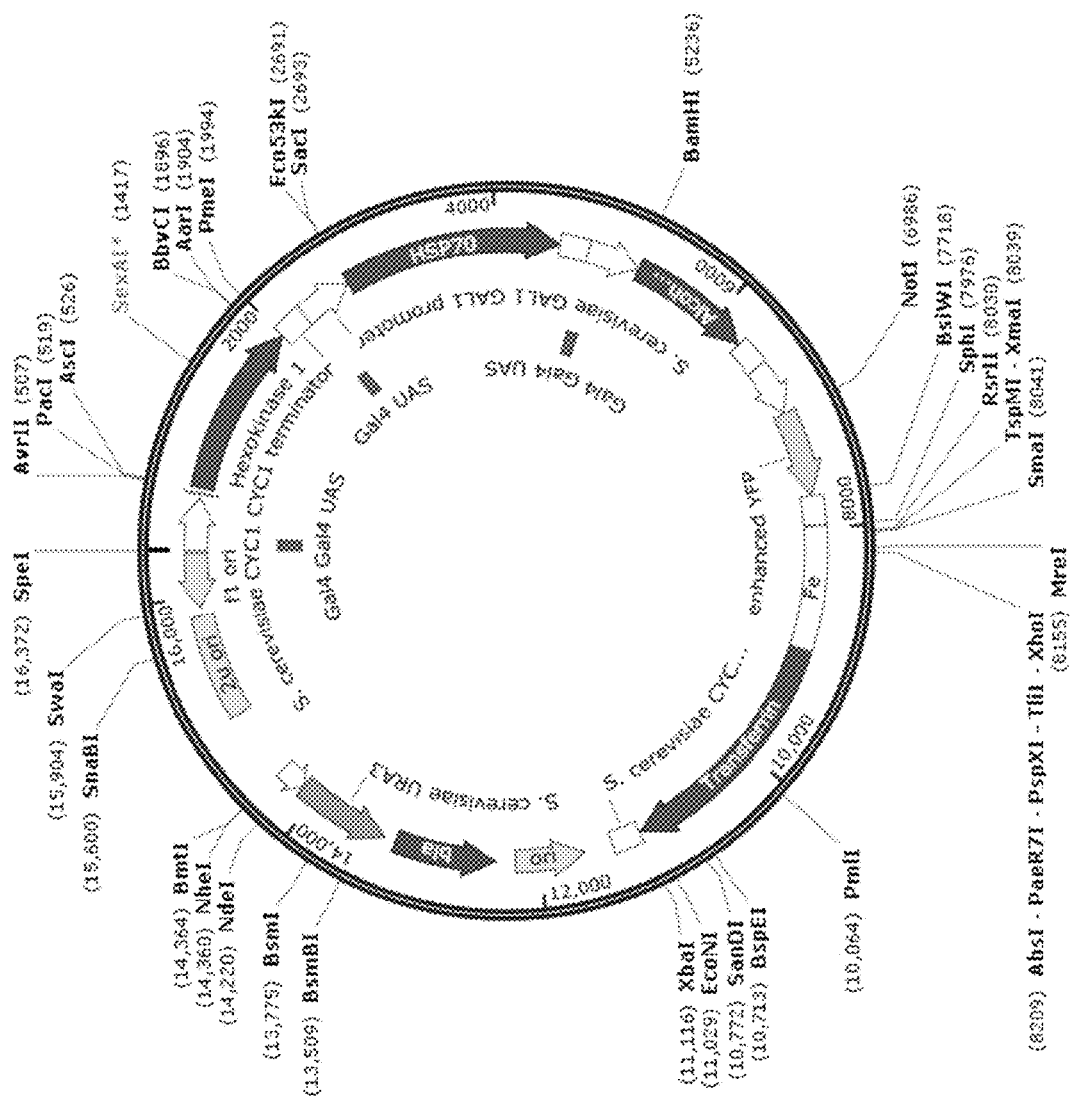

Yeast (*Saccharomyces cerevisiae*) transformed with the construct as provided in FIGS. 1A and 1B was fermented in yeast malt medium with 2% of raffinose, 1 mg/mL of glucosamine, and induced with 1% of galactose at 30° C. for 72 hours. After sonication for 150 minutes, the supernatant was sequentially filtered with 8 µm, 5 µm, 3 um, 2 µm and 1.2 µm filters. The extract isolated from filtrations was used below in the testing below.

Procedure for Biological Test for Anti UV Protection on *Bacillus subtilis* ATCC 82

A culture of Bacteria *Bacillus subtilis* (ATCC 82) was grown at 30° C. for one to two days. Aliquots were taken from this culture and subjected to different bacteria dilutions and the concentration was determined spectrophotometrically at the respective optical density, OD (i.e. 0.5, 1.0, 1.4, 2.0, with 1.4 as the preferred OD). Solutions were made from the above dilutions, and were mixed with different concentrations of the extract produced above at different proportions (i.e. 5:2 vol, extract:bacteria). These solutions were placed in Petri dishes with a total volume of 7 mL. These solutions were made in triplicates. Each solutions was placed in the UV incubator, and samples were taken at different times (i.e. 30 minutes, 1 hour, 2 hours).

Aliquots of 1 mL bacterial samples were taken from each replicate and fully mixed. Then, 500 µL were taken and placed on Nutrient agar by using standard streaking method, with 3 agar plate replicates were used at each time. The agar plates were incubated at 30° C. for 1-4 days. Bacterial colonies of *Bacillus subtilis* were viewed and counted at each time. The samples taken from the mixtures with no extract present showed essentially co colony growth; however, bacteria mixed with anti-UV extract showed considerable growth. The results indicate that the anti-UV extract can protect cells such as bacterial cells from exposure to UV light.

Procedure for Anti UV Protection on Fibroblast Cells ATCC 2522-CRL

Skin fibroblast were used as a model for human skin and were maintained in culture media for propagation and renewal following ATCC recommendations. The propagation medium is based on ATCC-formulated Eagles's Minimum Essential Medium, Catalog No 30-2003—Fetal bovine serum was added to the medium to a final concentration of 10%. The medium was also renewed according to ATCC instructions. This medium is made of 0.025% trypsin, 0.03% EDTA solution. Culture of fibroblast cells (ATCC 2522-CRL) was grown at 37° C. and 5% $CO_2$.

Extracts as produced above were applied to fibroblast culture with different ratios (volume) extract to fibroblast. This mixture was then exposed to UV-B radiation (302 nm) and UV-A (365 nm) for different times, and incubated at 37° C. and 5% of $CO_2$; each experiment was performed in triplicate.

Aliquots of fibroblast cells were harvested and subjected to microscopic analysis, carried out following standard procedure to count dead, living and apoptosis cells by staining the cells with trypan blue and viewing them under a compound microscope. Cells were counted at 20× magnification using several microscopic field views. Tables 9 and 10 provide the results of the experiment. The results indicate that the anti-UV extract can protect fibroblast cells from exposure to UV light.

TABLE 9

Percentage of alive, death, apoptosis fibroblast cells at different times and total survival and protection of experiment.
Protective effect of Anti-UV Extract on Skin Cells, Against UV-A at different times, proportion 5:4 (Extract:Skin cells culture)

| Type of cell | SCC + Water (Control) | | SCC + Anti-UV Extract (Treatment) | |
| --- | --- | --- | --- | --- |
| | 30 minutes | 1 hour | 30 minutes | 1 hour |
| Live Cells (Percentage) | 0 | 0 | 20 | 14 |
| Death Cells (Percentage) | 67 | 87 | 0 | 29 |
| Apoptose Cells (Percentage) | 33 | 13 | 80 | 57 |
| Total Survival (Percentage) | 33 | 13 | 100 | 71 |
| Protection (Percentage) | — | — | 67 | 58 |

TABLE 10

Percentage of alive, death, apoptosis fibroblast cells at different times and total survival and protection of experiment. Protective effect of Anti UV Extract on Skin Cells, Against UV-B at different times, proportion 5:4 (Extract:Skin cells culture)

| Type of cell | SCC + Water (Control) | | SCC + Anti-UV Extract | |
|---|---|---|---|---|
| | 30 minutes | 1 hour | 30 minutes | 1 hour |
| Live Cells (Percentage) | 0 | 0 | 60 | 50 |
| Death Cells (Percentage) | 75 | 90 | 10 | 28 |
| Apoptose Cells (Percentage) | 25 | 10 | 30 | 22 |
| Total Survival (Percentage) | 25 | 10 | 90 | 72 |
| Protection (Percentage) | — | — | 65 | 62 |

Throughout this application, various publications are referenced. The disclosures of these publications in their entireties are hereby incorporated by reference into this application in order to more fully describe the compounds, compositions, and methods described herein.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed:

1. A biological device comprising microbial host cells transformed with a vector, wherein the vector comprises a DNA construct comprising the following genetic components:
    (a) a gene having the nucleic acid sequence of SEQ ID NO: 4 or at least 90% homology thereto that encodes a hexokinase,
    (b) a gene having the nucleic acid sequence of SEQ ID NO: 5 or at least 90% homology thereto that encodes a heat shock protein,
    (c) a gene having the nucleic acid sequence of SEQ ID NO: 6 or at least 90% homology thereto that encodes an alcohol dehydrogenase, and
    (d) a gene having the nucleic acid sequence of SEQ ID NO: 8 or at least 90% homology thereto that encodes a transferrin.

2. The biological device of claim 1, wherein the gene that encodes the hexokinase has the nucleic acid sequence of SEQ ID NO: 4.

3. The biological device of claim 1, wherein the gene that encodes the heat shock protein encodes a HSP70 protein.

4. The biological device of claim 3, wherein the gene that encodes the HSP70 protein has the nucleic acid sequence of SEQ ID NO: 5.

5. The biological device of claim 1, wherein the gene that encodes the alcohol dehydrogenase has the nucleic acid sequence of SEQ ID NO: 6.

6. The biological device of claim 1, wherein the gene that encodes the transferrin has the nucleic acid sequence of SEQ ID NO: 8.

7. The biological device of claim 1, wherein the DNA construct further comprises a promoter.

8. The biological device of claim 7, wherein the promoter comprises a GAL1 promoter, an iron promoter, or both.

9. The biological device of claim 1, wherein the DNA construct further comprises a terminator.

10. The biological device of claim 9, wherein the terminator is CYC1 terminator.

11. The biological device of claim 1, wherein the DNA construct further comprises a gene that confers resistance to an antibiotic.

12. The biological device of claim 11, wherein the antibiotic comprises tetracycline, neomycin, kanamycin, ampicillin, hygromycin, chloramphenicol, amphotericin B, bacitracin, carbapenam, cephalosporin, ethambutol, fluoroquinolones, isonizid, methicillin, oxacillin, vancomycin, streptomycin, quinolines, rifampin, rifampicin, sulfonamides, cephalothin, erythromycin, streptomycin, gentamicin, penicillin, other commonly-used antibiotics, or a combination thereof.

13. The biological device of claim 1, wherein the construct further comprises a gene encoding a reporter protein.

14. The biological device of claim 1, wherein the DNA construct comprises from 5' to 3' the following genetic components in the following order:
    (1) the gene that encodes the hexokinase, (2) the gene that encodes the heat shock protein, (3) the gene that encodes the alcohol dehydrogenase, (4) a gene encodes an iron promoter having the nucleic acid sequence of SEQ ID NO: 7 or at least 90% homology thereto, and (5) the gene that encodes the transferrin.

15. The biological device of claim 1, wherein the vector is a plasmid.

16. The biological device of claim 15, wherein the plasmid is pWLNEO, pSV2CAT, pOG44, pXTI, pSG, pSVK3, pBSK, pBR322, pYES, pYES2, pBSKII, or pUC.

17. The biological device of claim 15 wherein the plasmid is pYES2.

18. The biological device of claim 15, wherein the plasmid is pBSK.

19. The biological device of claim 1, wherein the host cells comprise yeast or bacteria.

* * * * *

SEQUENCE LISTING

```
<160> NUMBER OF SEQ ID NOS: 12

<210> SEQ ID NO 1
<211> LENGTH: 16377
<212> TYPE: DNA
<213> ORGANISM: Artificial Sequence
<220> FEATURE:
<223> OTHER INFORMATION: Synthetic Construct

<400> SEQUENCE: 1
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagcttccta gggtttaatt aagtggcgcg ccatggttca     540
tttaggtcca agaaaccac  aggctagaaa gggttccatg gctgatgtgc ccaaggaatt     600
gatggatgaa attcatcagt tggaagatat gtttacagtt gacagcgaga ccttgagaaa     660
ggttgttaag cactttatcg acgaattgaa taaaggtttg acaaagaagg gaggtaacat     720
tccaatgatt cccggttggg tcatggaatt cccaacaggt aaagaatctg gtaactattt     780
ggccattgat ttgggtggta ctaacttaag agtcgtgttg gtcaagttga gcggtaacca     840
tacctttgac accactcaat ccaagtataa actaccacat gacatgagaa ccactaagca     900
ccaagaggag ttatggtcct ttattgccga ctctttgaag gactttatgg tcgagcaaga     960
attgctaaac accaaggaca ccttaccatt aggtttcacc ttctcgtacc cagcttccca    1020
aaacaagatt aacgaaggta ttttgcaaag atggaccaag ggtttcgata ttccaaatgt    1080
cgaaggccac gatgtcgtcc cattgctaca aaacgaaatt tccaagagag agttgcctat    1140
tgaaattgta gcattgatta atgatactgt tggtactttt attgcctcat actacactga    1200
cccagagact aagatgggtg tgattttcgg tactggtgtc aacggtgctt tctatgatgt    1260
tgtttccgat atcgaaaagt tggagggcaa attagcagac gatattccaa gtaactctcc    1320
aatggctatc aattgtgaat atggttcctt cgataatgaa catttggtct tgccaagaac    1380
```

```
caagtacgat gttgctgtcg acgaacaatc tccaagacct ggtcaacaag cttttgaaaa    1440
gatgacctcc ggttactact tgggtgaatt gttgcgtcta gtgttacttg aattaaacga    1500
gaagggcttg atgttgaagg atcaagatct aagcaagttg aaacaaccat acatcatgga    1560
tacctcctac ccagcaagaa tcgaggatga tccatttgaa acttggaag atactgatga     1620 catcttccaa aaggactttg gtgtcaagac cactctgcca gaacgtaagt tgattagaag    1680
actttgtgaa ttgatcggta ccagagctgc tagattagct gtttgtggta ttgccgctat    1740
ttgccaaaag agaggttaca agactggtca cattgccgct gacggttctg tctataacaa    1800
atacccaggt ttcaaggaag ccgccgctaa gggtttgaga gatatctatg gatgactgg     1860 tgacgcaagc aaagatccaa ttacgattgt tccagctgag gatggttcag gtgcaggtgc    1920
tgctgttatt gctgcattgt ccgaaaaaag aattgccgaa ggtaagtctc ttggtatcat    1980
tggcgcttaa gtttaaactc atgtaattag ttatgtcacg cttacattca cgccctcccc    2040
ccacatccgc tctaaccgaa aaggaaggag ttagacaacc tgaagtctag gtccctattt    2100
atttttttat agttatgtta gtattaagaa cgttatttat atttcaaatt tttctttttt    2160
ttctgtacag acgcgtgtac gcatgtaaca ttatactgaa aaccttgctt gagaaggttt    2220
tgggacgctc gaaggcttta atttgccgga ttagaagccg ccgagcgggt gacagccctc    2280
cgaaggaaga ctctcctccg tgcgtcctcg tcttcaccgg tcgcgttcct gaaacgcaga    2340
tgtgcctcgc gccgcactgc tccgaacaat aaagattcta caatactagc ttttatggtt    2400
atgaagagga aaaattggca gtaacctggc cccacaaacc ttcaaatgaa cgaatcaaat    2460
taacaaccat aggatgataa tgcgattagt ttttagcct tatttctggg gtaattaatc      2520
agcgaagcga tgattttga tctattaaca gatatataaa tgcaaaaact gcataaccac      2580
tttaactaat acttcaaca ttttcggttt gtattacttc ttattcaaat gtaataaaag      2640
tatcaacaaa aaattgttaa tatacctcta tactttaacg tcaaggagga gctcaccatg    2700
gctgaaggtg ttttccaagg tgctatcggt atcgatttag gtacaaccta ctcttgtgtt    2760
gctacttacg aatcctccgt tgaaattatt gccaacgaac aaggtaacag agtcaccca     2820 tctttcgttg ctttcactcc agaagaaaga ttgattggtg atgctgccaa gaaccaagct    2880
gctttgaacc caagaaacac tgtcttcgat gctaagcgtt tgattggtag aagattcgac    2940
gacgaatctg ttcaaaagga catgaagacc tggcctttca aggttatcga cgtcgatggt    3000
aacccagtca tcgaagtcca atacttggaa gaaaccaaga ctttctcccc caagaaatt    3060 tccgctatgg ttttgaccaa gatgaaggaa attgctgaag ctaagattgg taagaaggtt    3120
gaaaaggccg tcattactgt cccagcttac tttaacgacg ctcaaagaca agctaccaag    3180
gatgccggtg ccatttctgg tttgaacgtt ttgcgtatca tcaacgaacc tactgccgct    3240
gctattgctt acggtctagg tgctggtaag tccgaaaagg aaagacatgt tttgatttc     3300 gatttgggtg gtggtacttt cgatgtttcc ttgttgcaca ttgctggtgg tgtttacact    3360
gttaaatcta cttccggtaa cactcacttg ggtggtcaag atttcgacac caacttgttg    3420
gaacacttca aggctgaatt caagaagaag actggtttgg acatctccga cgatgccaga    3480
gctttgagaa gattgagaac tgctgctgaa agagctaaga gaaccttatc ttctgtcact    3540
caaactaccg ttgaagttga ctctttgttt gacggtgaag atttcgaatc ctctttgact    3600
agagctagat ttgaagactt gaacgccgca ttgttcaagt ctactttgga acctgttgaa    3660
caagttttga aggatgctaa gatctctaag tctcaaatcg acgaagttgt cttggttggt    3720
ggttccacca gaattccaaa ggtccaaaag ttgttgtctg acttctttga cggtaagcaa    3780
```

```
ttggaaaaat ctattaaccc agatgaagct gttgcttacg gtgctgctgt tcaaggtgct    3840
atcttgaccg gccaatccac atctgacgaa accaaggact tgttgttgtt agatgttgct    3900
ccattatctc taggtgttgg tatgcaaggt gacatgttcg gtatcgttgt tccaagaaac    3960
actactgttc caaccatcaa gagaagaacc tttactacat gtgctgacaa ccaaaccacc    4020
gttcaattcc cagtctacca aggtgaacgt gttaactgta aagaaaacac tttgttgggt    4080
gaattcgact tgaagaacat cccaatgatg ccagctggtg aaccagtctt ggaagctatc    4140
ttcgaagttg atgctaacgg tatcttgaag gttactgccg tcgaaaagtc taccggtaag    4200
tcttctaaca tcactatctc taacgctgtt ggtagattgt cttctgaaga aattgaaaag    4260
atggttaacc aagctgaaga gttcaaggct gccgatgaag cttttgccaa gaagcacgaa    4320
gctagacaaa gattggaatc ctacgttgcc tccatcgaac aaactgtcac tgacccagtc    4380
ttgtcttcta aattgaagag aggttccaag tccaagattg aagctgcttt gtccgatgct    4440
ttggctgctt tgcaaatcga agacccatct gctgatgaat tgagaaaggc tgaagttggt    4500
ttgaagagag ttgtcaccaa ggccatgtct tctcgttaag gtacctcatg taattagtta    4560
tgtcacgctt acattcacgc cctccccca catccgctct aaccgaaaag gaggagtta    4620 gacaacctga agtctaggtc cctatttatt tttttatagt tatgttagta ttaagaacgt    4680
tatttatatt tcaaatttt cttttttttc tgtacagacg cgtgtacgca tgtaacatta    4740
tactgaaaac cttgcttgag aaggttttgg gacgctcgaa ggctttaatt tgccggatta    4800
gaagccgccg agcgggtgac agccctccga aggaagactc tcctccgtgc gtcctcgtct    4860
tcaccggtcg cgttcctgaa acgcagatgt gcctcgcgcc gcactgctcc gaacaataaa    4920
gattctacaa tactagcttt tatggttatg aagaggaaaa attggcagta acctggcccc    4980
acaaaccttc aaatgaacga atcaaattaa caaccatagg atgataatgc gattagtttt    5040
ttagccttat ttctggggta attaatcagc gaagcgatga ttttgatct attaacagat    5100 atataaatgc aaaaactgca taaccacttt aactaatact ttcaacattt tcggtttgta    5160
ttacttctta ttcaaatgta ataaagtat caacaaaaaa ttgttaatat acctctatac    5220
tttaacgtca aggagggatc catgtctatt ccagaaactc aaaaagccat tatcttctac    5280
gaatccaacg gcaagttgga gcataaggat atcccagttc caaagccaaa gcccaacgaa    5340
ttgttaatca acgtcaagta ctctggtgtc tgccacaccg atttgcacgc ttggcatggt    5400
gactggccat tgccaactaa gttaccatta gttggtggtc acgaaggtgc cggtgtcgtt    5460
gtcggcatgg gtgaaaacgt taagggctgg aagatcggtg actacgccgg tatcaaatgg    5520
ttgaacggtt cttgtatggc ctgtgaatac tgtgaattgg gtaacgaatc caactgtcct    5580
cacgctgact tgtctggtta cacccacgac ggttctttcc aagaatacgc taccgctgac    5640
gctgttcaag ccgctcacat tcctcaaggt actgacttgg ctgaagtcgc gccaatcttg    5700
tgtgctggta tcaccgtata caaggctttg aagtctgcca acttgagagc aggccactgg    5760
gcggccattt ctggtgctgc tggtggtcta ggttctttgg ctgttcaata tgctaaggcg    5820
atgggttaca gagtcttagg tattgatggt ggtccaggaa aggaagaatt gtttacctcg    5880
ctcggtggtg aagtattcat cgacttcacc aaagagaagg acattgttag cgcagtcgtt    5940
aaggctacca acggcggtgc ccacggtatc atcaatgttt ccgttccgga agccgctatc    6000
gaagcttcta ccagatactg tagggcgaac ggtactgttg tcttggttgg tttgccagcc    6060
ggtgcaaagt gctcctctga tgtcttcaac cacgttgtca agtctatctc cattgtcggc    6120
```

```
tcttacgtgg ggaacagagc tgataccaga gaagccttag atttctttgc cagaggtcta    6180
gtcaagtctc caataaaggt agttggctta tccagtttac cagaaattta cgaaaagatg    6240
gagaagggcc aaattgctgg tagatacgtt gttgacactt ctaaataaga attctcatgt    6300
aattagttat gtcacgctta cattcacgcc ctcccccac atccgctcta accgaaaagg     6360
aaggagttag acaacctgaa gtctaggtcc ctatttattt ttttatagtt atgttagtat    6420
taagaacgtt atttatattt caaattttc ttttttttct gtacagacgc gtgtacgcat     6480
gtaacattat actgaaaacc ttgcttgaga aggttttggg acgctcgaag gctttaattt    6540
gccggattag aagccgccga gcgggtgaca gccctccgaa ggaagactct cctccgtgcg    6600
tcctcgtctt caccggtcgc gttcctgaaa cgcagatgtg cctcgcgccg cactgctccg    6660
aacaataaag attctacaat actagctttt atggttatga agaggaaaaa ttggcagtaa    6720
cctggcccca caaaccttca aatgaacgaa tcaaattaac aaccatagga tgataatgcg    6780
attagttttt tagccttatt ctgggtaa ttaatcagcg aagcgatgat ttttgatcta      6840
ttaacagata tataaatgca aaactgcat aaccactta actaatactt tcaacattt       6900 cggtttgtat tacttcttat tcaaatgtaa taaaagtatc aacaaaaaat tgttaatata    6960
cctctatact ttaacgtcaa ggaggcggcc gccatggtga gcaagggcga ggagctgttc    7020
accggggtgg tgcccatcct ggtcgagctg gacggcgacg taaacggcca caagttcagc    7080
gtgtccggcg agggcgaggg cgatgccacc tacggcaagc tgaccctgaa gttcatctgc    7140
accaccggca agctgcccgt gccctggccc accctcgtga ccaccttcgg ctacggcctg    7200
caatgcttcg cccgctaccc cgaccacatg aagctgcacg acttcttcaa gtccgccatg    7260
cccgaaggct acgtccagga gcgcaccatc ttcttcaagg acgacggcaa ctacaagacc    7320
cgcgccgagg tgaagttcga gggcgacacc ctggtgaacc gcatcgagct gaagggcatc    7380
gacttcaagg aggacggcaa catcctgggg cacaagctgg agtacaacta caacagccac    7440
aacgtctata tcatggccga caagcagaag aacggcatca aggtgaactt caagatccgc    7500
cacaacatcg aggacggcag cgtgcagctc gccgaccact accagcagaa cacccccatc    7560
ggcgacggcc ccgtgctgct gcccgacaac cactacctga gctaccagtc cgccctgagc    7620
aaagacccca acgagaagcg cgatcacatg gtcctgctgg agttcgtgac cgccgccggg    7680
atcactctcg gcatggacga gctgtacaag taataatcgt acgcatcatg taattagtta    7740
tgtcacgctt acattcacgc cctccccca catccgctct aaccgaaaag gaaggagtta    7800
gacaacctga gtctaggtc cctatttatt tttttatagt tatgttagta ttaagaacgt     7860
tatttatatt tcaaattttt cttttttttc tgtacagacg cgtgtacgca tgtaacatta    7920
tactgaaaac cttgcttgag aaggttttgg gacgctcgaa ggctttaatt tgcatgctag    7980
tagttaggtg ccctggccgt tcccagcatt ggtggccgcg gccgtggccg gaccggcgcc    8040
cggggtggcg cccagcaccg actgcaggtc aggcttcatc gcctgcagct gcgcgcccca    8100
gtagggccag tcgtgggtgc cgttggcgtc gaagttccac accgcgttgt ggccgccggc    8160
gccgttgtag gcgtcctgga acttcaggtt ggacgtccgc acgaagccct cgaggaactt    8220
ggcgggcagg ttgtcgccac cgaggtcgga cggcttgccg ttgccgcagt acacccagat    8280
ccgggtgttg ttcgcgacca gcttgccgac ctgcagcgac gggtcgttgc gggcccaggc    8340
cgggtcctcc ttcggacccc acatgtcggc ggccttgtag ccaccggcgt cacccatggc    8400
cagcccgatc agcgacgggc ccatgccctg cgacgagtcc agcagcgccg acagcgagcc    8460
ggcgtagacg aactggtcgg ggtggtaggc ggccaggatc agcgccgagg agccggccat    8520
```

-continued

```
cgacaggccg acgacaccgc tgccggtcgg cttgacctgc ttctgcgccg acaggtactg   8580
cggcagctcg ctggtcagga aggtctccca cttgtaggtg gtgcagccgg ccttgccgca   8640
ggcgggcttg taccagtcgg agtagaagct ggactggccg ccgaccggca tggcgaccga   8700
gatgcccgac tggttgtacc actcgaacgc cggggtgttg atgtcccagc cgttgaagtc   8760
gtcttgcgcg cgcatcccgt cgagcaggta caacgcgggc gagttggccc caccgctttg   8820
gaactggacc ttgatgtccc gtcccatggc ggcggaggga acctgcaggt actccaccgg   8880
cagaccgggg cgcgagaagg ccccggcggt cgccgagccc cgacggcgc caatcaggcc    8940 cgagagcagc gccgcaccag cggcccccac cacgagccgg cgcggcatcc ccgccacggc   9000
gccgcgcaat ctgtcgacat gcgtctggcc gttggtgccc tgctggtgtg cgcggtgctg   9060
ggcctgtgcc tggccgtccc agataaaacc gttcgctggt gcgcagtcag tgagcatgaa   9120
gcgacgaagt gccaatcttt ccgcgatcac atgaaaagcg taattccgag cgatggtccg   9180
agtgtagctt gtgttaagaa agcaagctat ctggactgta tccgcgcaat gcagcgaac   9240 gaagctgatg cagttaccct ggacgcaggt ctggtttacg acgcgtacct ggctcctaac   9300
aatctgaaac cggttgtagc ggagttctat ggtagtaaag aagacccgca aactttctat   9360
tatgcagtgg ccgtggtaaa aaggactct ggttttcaga tgaaccagct gcgtgggaag    9420
aaaagttgtc atacgggcct ggggcgttct gcggttgga acattccaat tgggctgctg    9480
tattgcgatc tgccggaacc acgcaagccg ctggagaaag ctgtagcgaa cttcttcagt   9540
ggttcttgtg cgccttgcgc cgatggtact gattttccgc agctgtgtca gctgtgtccg   9600
ggctgcggtt gttctacccct gaatcagtac tttggctata gtggggcgtt taaatgcctg   9660
aaagatgggg cgggtgacgt ggcgttcgtc aaacattcta cgattttcga aacctggcg    9720 aacaaagcag atcgtgacca atatgaactg ctgtgtctgg acaacactcg caagccagtc   9780
gatgaatata aagattgtca tctggcacaa gtgcctagtc atactgtggt cgcgcgtagc   9840
attggtggta aggaggacct gatttgggaa ctgctgaacc aagctcagga gcatttcggc   9900
aaagataaaa gcaaagaatt tcagctgttt tctagccccgc acggcaaaga cctgctgttt   9960
aaagacagcg cccacggctt tctgaaagtg cctccacgca tggatgccaa aatgtatctg  10020
ggttatgaat atgttacggc aattcgcaat ctgcgtgaag gcacgtgccc ggaagctccg  10080
actgacgagt gcaaaccagt aaagtggtgt gccctgtctc atcatgagcg cctgaaatgt  10140
gatgaatgga gtgtgaactc tgttggcaaa attgagtgcg ttagtgctga aaccaccgag  10200
gactgtatcg caaagatcat gaacggcgaa gcagatgcta tgtctctgga tggcggtttt  10260
gtgtatatcg caggtaaatg cggcctggtc ccagttctgg ctgaaaatta acaaaagt    10320 gataactgtg aggatactcc aggggcggc tattttgcgg tcgctgtcgt caagaaatct   10380
gcgagcgatc tgacatggga taacctgaaa gggaagaaat cttgccatac cgcggttggc  10440
cgcaccgctg gtggaacat cccgatgggc ctgctgtata caaaatcaa tcattgccgt    10500 tttgacgagt tcttcagtga ggggtgtgcg cctggtagta agaaagatag cagcctgtgc  10560
aaactgtgca tgggcagcgg cctgaatctg tgcgaaccta caataaaga gggttactac   10620 ggctacaccg gcgcgtttcg ctgcctggtt gagaaaggtg atgttgcgtt tgtaaagcac  10680
caaacagtac cgcagaatac gggtgggaag aatccggacc cgtgggccaa gaatctgaat  10740
gaaaaggatt acgaactgct gtgcctggat gggacccgca agccggttga agaatacgcg  10800
aattgtcacc tggcccgcgc cccgaatcac gccgtggtga cgcgcaaaga taagagggcc  10860
```

-continued

```
tgcgtccaca aaatcctgcg tcagcagcag cacctgttcg gcagcaatgt gacagattgt   10920
agcggtaatt tctgtctgtt ccgtagcgaa accaaggacc tgctgttccg tgacgacacc   10980
gtgtgtctgg ccaaactgca cgaccgtaat acctacgaga aatacctggg cgaggagtac   11040
gtgaaagccg tgggcaatct gcgtaagtgt agcacaagca gcctgctgga agcctgcaca   11100
tttcgtcgtc cgtaatctag agggccgcat catgtaatta gttatgtcac gcttacattc   11160
acgccctccc cccacatccg ctctaaccga aaaggaagga gttagacaac ctgaagtcta   11220
ggtccctatt tattttttta tagttatgtt agtattaaga acgttattta tatttcaaat   11280
ttttcttttt tttctgtaca gacgcgtgta cgcatgtaac attatactga aaaccttgct   11340
tgagaaggtt ttgggacgct cgaaggcttt aatttgcggc cctgcattaa tgaatcggcc   11400
aacgcgcggg gagaggcggt ttgcgtattg ggcgctcttc cgcttcctcg ctcactgact   11460
cgctgcgctc ggtcgttcgg ctgcggcgag cggtatcagc tcactcaaag gcggtaatac   11520
ggttatccac agaatcaggg gataacgcag gaaagaacat gtgagcaaaa ggccagcaaa   11580
agcccaggaa ccgtaaaaag gccgcgttgc tggcgttttt ccataggctc cgcccccctg   11640
acgagcatca aaaaatcga cgctcaagtc agaggtggcg aaacccgaca ggactataaa   11700
gataccaggc gtttccccct ggaagctccc tcgtgcgctc tcctgttccg accctgccgc   11760
ttaccggata cctgtccgcc tttctccctt cgggaagcgt ggcgctttct catagctcac   11820
gctgtaggta tctcagttcg gtgtaggtcg ttcgctccaa gctgggctgt gtgcacgaac   11880
cccccgttca gcccgaccgc tgcgccttat ccggtaacta tcgtcttgag tccaacccgg   11940
taagacacga cttatcgcca ctggcagcag ccactggtaa caggattagc agagcgaggt   12000
atgtaggcgg tgctacagag ttcttgaagt ggtggcctaa ctacggctac actagaagga   12060
cagtatttgg tatctgcgct ctgctgaagc cagttacctt cggaaaaaga gttggtagct   12120
cttgatccgg caaacaaacc accgctggta gcggtggttt ttttgtttgc aagcagcaga   12180
ttacgcgcag aaaaaaagga tctcaagaag atcctttgat cttttctacg ggtctgacg   12240 ctcagtggaa cgaaaactca cgttaaggga ttttggtcat gagattatca aaaaggatct   12300
tcacctagat ccttttaaat taaaaatgaa gttttaaatc aatctaaagt atatatgagt   12360
aaacttggtc tgacagttac caatgcttaa tcagtgaggc acctatctca gcgatctgtc   12420
tatttcgttc atccatagtt gcctgactcc ccgtcgtgta gataactacg atacgggagc   12480
gcttaccatc tggccccagt gctgcaatga taccgcgaga cccacgctca ccggctccag   12540
atttatcagc aataaaccag ccagccgaa gggccgagcg cagaagtggt cctgcaactt   12600
tatccgcctc catccagtct attaattgtt gccgggaagc tagagtaagt agttcgccag   12660
ttaatagttt gcgcaacgtt gttggcattg ctacaggcat cgtggtgtca ctctcgtcgt   12720
ttggtatggc ttcattcagc tccggttccc aacgatcaag gcgagttaca tgatccccca   12780
tgttgtgcaa aaaagcggtt agctccttcg gtcctccgat cgttgtcaga agtaagttgg   12840
ccgcagtgtt atcactcatg gttatggcag cactgcataa ttctcttact gtcatgccat   12900
ccgtaagatg cttttctgtg actggtgagt actcaaccaa gtcattctga gaatagtgta   12960
tgcggcgacc gagttgctct tgcccggcgt caatacggga taatagtgta tcacatagca   13020
gaactttaaa agtgctcatc attggaaaac gttcttcggg gcgaaaactc tcaaggatct   13080
taccgctgtt gagatccagt tcgatgtaac ccactcgtgc acccaactga tcttcagcat   13140
cttttacttt caccagcgtt tctgggtgag caaaaacagg aaggcaaaat gccgcaaaaa   13200
agggaataag ggcgacacgg aaatgttgaa tactcatact cttcctttt caatgggtaa   13260
```

```
taactgatat aattaaattg aagctctaat ttgtgagttt agtatacatg catttactta   13320
taatacagtt ttttagtttt gctggccgca tcttctcaaa tatgcttccc agcctgcttt   13380
tctgtaacgt tcaccctcta ccttagcatc ccttcccttt gcaaatagtc ctcttccaac   13440
aataataatg tcagatcctg tagagaccac atcatccacg gttctatact gttgacccaa   13500
tgcgtctccc ttgtcatcta aacccacacc gggtgtcata atcaaccaat cgtaaccttc   13560
atctcttcca cccatgtctc tttgagcaat aaagccgata acaaaatctt tgtcgctctt   13620
cgcaatgtca acagtaccct tagtatattc tccagtagat agggagccct tgcatgacaa   13680
ttctgctaac atcaaaaggc ctctaggttc ctttgttact tcttctgccg cctgcttcaa   13740
accgctaaca atacctgggc ccaccacacc gtgtgcattc gtaatgtctg cccattctgc   13800
tattctgtat acacccgcag agtactgcaa tttgactgta ttaccaatgt cagcaaattt   13860
tctgtcttcg aagagtaaaa aattgtactt ggcggataat gcctttagcg cttaactgt   13920
gccctccatg gaaaaatcag tcaagatatc cacatgtgtt tttagtaaac aaattttggg   13980
acctaatgct tcaactaact ccagtaattc cttggtggta cgaacatcca atgaagcaca   14040
caagtttgtt tgcttttcgt gcatgatatt aaatagcttg gcagcaacag gactaggatg   14100
agtagcagca cgttccttat atgtagcttt cgacatgatt tatcttcgtt tcctgcaggt   14160
ttttgttctg tgcagttggg ttaagaatac tgggcaattt catgtttctt caacactaca   14220
tatgcgtata tataccaatc taagtctgtg ctccttcctt cgttcttcct tctgttcgga   14280
gattaccgaa tcaaaaaaat ttcaaagaaa ccgaaatcaa aaaaagaat aaaaaaaaaa   14340
tgatgaattg aattgaaaag ctagcttatc gatgataagc tgtcaaagat gagaattaat   14400
tccacggact atagactata ctagatactc cgtctactgt acgatacact tccgctcagg   14460
tccttgtcct ttaacgaggc cttaccactc ttttgttact ctattgatcc agctcagcaa   14520
aggcagtgtg atctaagatt ctatcttcgc gatgtagtaa aactagctag accgagaaag   14580
agactagaaa tgcaaaaggc acttctacaa tggctgccat cattattatc cgatgtgacg   14640
ctgcagcttc tcaatgatat tcgaatacgc tttgaggaga tacagcctaa tatccgacaa   14700
actgttttac agatttacga tcgtacttgt tacccatcat tgaattttga acatccgaac   14760
ctgggagttt tccctgaaac agatagtata tttgaacctg tataataata tatagtctag   14820
cgctttacgg aagacaatgt atgtatttcg gttcctggag aaactattgc atctattgca   14880
taggtaatct tgcacgtcgc atccccggtt cattttctgc gtttccatct tgcacttcaa   14940
tagcatatct ttgttaacga agcatctgtg cttcattttg tagaacaaaa atgcaacgcg   15000
agagcgctaa ttttttcaaac aaagaatctg agctgcatttt ttacagaaca gaaatgcaac   15060
gcgaaagcgc tattttacca acgaagaatc tgtgcttcat ttttgtaaaa caaaaatgca   15120
acgcgacgag agcgctaatt tttcaaacaa agaatctgag ctgcattttt acagaacaga   15180
aatgcaacgc gagagcgcta ttttaccaac aaagaatcta tacttctttt tgttctaca   15240
aaaatgcatc ccgagagcgc tatttttcta caaagcatc ttagattact ttttttctcc   15300
tttgtgcgct ctataatgca gtctcttgat aactttttgc actgtaggtc cgttaaggtt   15360
agaagaaggc tactttggtg tctatttttct cttccataaa aaaagcctga ctccacttcc   15420
cgcgtttact gattactagc gaagctgcgg gtgcattttt tcaagataaa ggcatccccg   15480
attatattct ataccgatgt ggattgcgca ctttgtga acagaaagtg atagcgttga   15540
tgattcttca ttggtcagaa aattatgaac ggtttcttct attttgtctc tatatactac   15600
```

```
gtataggaaa tgtttacatt ttcgtattgt tttcgattca ctctatgaat agttcttact   15660 acaattttt tgtctaaaga gtaatactag agataaacat aaaaaatgta gaggtcgagt    15720
ttagatgcaa gttcaaggag cgaaaggtgg atgggtaggt tatatagga tatagcacag    15780 agatatatag caaagagata cttttgagca atgtttgtgg aagcggtatt cgcaatggga   15840
agctccaccc cggttgataa tcagaaaagc cccaaaaaca ggaagattgt ataagcaaat   15900
atttaaattg taaacgttaa tattttgtta aaattcgcgt taaattttg ttaaatcagc    15960 tcatttttta acgaatagcc cgaaatcggc aaaatccctt ataaatcaaa agaatagacc   16020
gagatagggt tgagtgttgt tccagtttcc aacaagagtc cactattaaa gaacgtggac   16080
tccaacgtca aagggcgaaa aagggtctat cagggcgatg gcccactacg tgaaccatca   16140
ccctaatcaa gttttttggg gtcgaggtgc cgtaaagcag taaatcggaa gggtaaacgg   16200 atgccccat ttagagcttg acggggaaag ccggcgaacg tggcgagaaa ggaagggaag    16260
aaagcgaaag gagcgggggc tagggcggtg ggaagtgtag gggtcacgct gggcgtaacc   16320
accacacccg ccgcgcttaa tggggcgcta cagggcgcgt ggggatgatc cactagt      16377

<210> SEQ ID NO 2
<211> LENGTH: 16292
<212> TYPE: DNA
<213> ORGANISM: Artificial Sequence
<220> FEATURE:
<223> OTHER INFORMATION: Synthetic Construct

<400> SEQUENCE: 2
acggattaga agccgccgag cgggtgacag ccctccgaag gaagactctc ctccgtgcgt     60
cctcgtcttc accggtcgcg ttcctgaaac gcagatgtgc ctcgcgccgc actgctccga   120
acaataaaga ttctacaata ctagctttta tggttatgaa gaggaaaaat tggcagtaac   180
ctggccccac aaaccttcaa atgaacgaat caaattaaca accataggat gataatgcga   240
ttagtttttt agccttattt ctggggtaat taatcagcga agcgatgatt tttgatctat   300
taacagatat ataaatgcaa aaactgcata accactttaa ctaatacttt caacattttc   360
ggtttgtatt acttcttatt caatgtaat aaaagtatca acaaaaaatt gttaatatac    420
ctctatactt taacgtcaag gagaaaaaac cccggatcgg actactagca gctgtaatac   480
gactcactat agggaatatt aagcttccta ggatggaggt cgaaagagtc caagacattt   540
catcttcttc tctactaaca gaagcaatcc cgttggagtt catcagatca gagaaagaac   600
aaccagcgat cacaacattc cgaggtccaa cgccggcgat tcccgtcgtc gatctaagcg   660
atcccgacga agaaagcgtg aggcgcgcgg tggtgaaagc gagtgaagaa tggggggctat  720 tccaagtggt taaccacggg attccgacgg agctgatacg acgtttacaa gacgtcggaa   780
gaaaattctt cgagcttcct tcgtcggaga agaatccgt cgctaaaccg gaagattcga    840
aagacattga aggatacgga acaaagcttc agaaagatcc agaaggtaaa aaagcttggg   900
tcgatcatct cttccatcga atctggccac cgtcatgcgt caattacaga ttctggccta   960
agaatccacc tgaatacagg gaggtgaatg aagagtatgc agtgcatgtg aagaagctat   1020
cggagacgtt attagggatt ctctcggatg gattagggtt aaagcgtgat gcgttgaaag   1080
aaggtctcgg cggagagatg gcggagtata tgatgaagat taactattat ccgccgtgtc   1140
ctcggccgga tttagcttta ggtgtaccgg ctcatacaga tctcagtgga atcactcttc   1200
ttgttcctaa cgaagttcct ggacttcaag ttttcaaaga tgatcactgg ttcgatgcag   1260
agtatattcc ctccgccgtc attgttcaca tcggcgatca gattctgagg ttgagtaatg   1320
```

```
ggaggtataa aaatgtgttg cataggacga cggtggataa agagaagacg aggatgtcgt    1380
ggccggtttt cttggagcct ccccgtgaaa agattgttgg acctttaccg gaactaaccg    1440
gagatgataa tcctccaaag tttaaaccgt ttgctttcaa ggattacagt taccgcaagc    1500
tcaataaact tcctctggat tgattaatta atcatgtaat tagttatgtc acgcttacat    1560
tcacgccctc cccccacatc cgctctaacc gaaaggaag gagttagaca acctgaagtc     1620
taggtcccta tttattttt tatagttatg ttagtattaa gaacgttatt tatatttcaa     1680
attttctttt tttttctgta cagacgcgtg tacgcatgta acattatact gaaaaccttg    1740
cttgagaagg ttttgggacg ctcgaaggct ttaatttgcc ggattagaag ccgccgagcg    1800
ggtgacagcc ctccgaagga agactctcct ccgtgcgtcc tcgtcttcac cggtcgcgtt    1860
cctgaaacgc agatgtgcct cgcgccgcac tgctccgaac aataaagatt ctacaatact    1920 agctttatg gttatgaaga ggaaaaattg gcagtaacct ggccccacaa accttcaaat     1980
gaacgaatca aattaacaac cataggatga taatgcgatt agttttttag ccttatttct    2040
ggggtaatta atcagcgaag cgatgatttt tgatctatta acagatatat aaatgcaaaa    2100
actgcataac cactttaact aatactttca acattttcgg tttgtattac ttcttattca    2160
aatgtaataa aagtatcaac aaaaaattgt taatatacct ctatacttta acgtcaagga    2220
gggcgcgcca tggttcattt aggtccaaag aaaccacagg ctagaaaggg ttccatggct    2280
gatgtgccca aggaattgat ggatgaaatt catcagttgg aagatatgtt tacagttgac    2340
agcgagacct tgagaaaggt tgttaagcac tttatcgacg aattgaataa aggtttgaca    2400
aagaagggag gtaacattcc aatgattccc ggttgggtca tggaattccc aacaggtaaa    2460
gaatctggta actatttggc cattgatttg ggtggtacta acttaagagt cgtgttggtc    2520
aagttgagcg gtaaccatac ctttgacacc actcaatcca agtataaact accacatgac    2580
atgagaacca ctaagcacca agaggagtta tggtcccttta ttgccgactc tttgaaggac   2640
tttatggtcg agcaagaatt gctaaacacc aaggacacct taccattagg tttcaccttc    2700
tcgtacccag cttcccaaaa caagattaac gaaggtattt tgcaaagatg gaccaagggt    2760
ttcgatattc caaatgtcga aggccacgat gtcgtcccat gctacaaaa cgaaatttcc     2820 aagagagagt tgcctattga aattgtagca ttgattaatg atactgttgg tactttaatt    2880
gcctcatact acactgaccc agagactaag atgggtgtga ttttcggtac tggtgtcaac    2940
ggtgctttct atgatgttgt ttccgatatc gaaaagttgg agggcaaatt agcagacgat    3000
attccaagta actctccaat ggctatcaat tgtgaatatg gttccttcga taatgaacat    3060
ttggtcttgc caagaaccaa gtacgatgtt gctgtcgacg aacaatctcc aagacctggt    3120
caacaagctt tgaaaagat gacctccggt tactacttgg gtgaattgtt gcgtctagtg     3180
ttacttgaat taaacgagaa gggcttgatg ttgaaggatc aagatctaag caagttgaaa    3240
caaccataca tcatggatac ctcctaccca gcaagaatcg aggatgatcc atttgaaaac    3300
ttggaagata ctgatgacat cttccaaaag gactttggtg tcaagaccac tctgccagaa    3360
cgtaagttga ttagaagact ttgtgaattg atcggtacca gagctgctag attagctgtt    3420
tgtggtattg ccgctatttg ccaaaagaga ggttacaaga ctggtcacat tgccgctgac    3480
ggttctgtct ataacaaata cccaggtttc aaggaagccg ccgctaaggg tttgagagat    3540
atctatggat ggactggtga cgcaagcaaa gatccaatta cgattgttcc agctgaggat    3600
ggttcaggtg caggtgctgc tgttattgct gcattgtccg aaaaaagaat tgccgaaggt    3660
```

```
aagtctcttg gtatcattgg cgcttaagtt taaactcatg taattagtta tgtcacgctt    3720
acattcacgc cctccccca catccgctct aaccgaaaag gaaggagtta gacaacctga    3780
agtctaggtc cctatttatt tttttatagt tatgttagta ttaagaacgt tatttatatt    3840 tcaaatttt cttttttc tgtacagacg cgtgtacgca tgtaacatta tactgaaaac    3900
cttgcttgag aaggttttgg gacgctcgaa ggctttaatt tgccggatta gaagccgccg    3960
agcgggtgac agccctccga aggaagactc tcctccgtgc gtcctcgtct tcaccggtcg    4020
cgttcctgaa acgcagatgt gcctcgcgcc gcactgctcc gaacaataaa gattctacaa    4080
tactagcttt tatggttatg aagaggaaaa attggcagta acctggcccc acaaaccttc    4140
aaatgaacga atcaaattaa caaccatagg atgataatgc gattagtttt ttagccttat    4200
ttctggggta attaatcagc gaagcgatga ttttgatct attaacagat atataaatgc    4260
aaaaactgca taaccacttt aactaatact ttcaacattt tcggtttgta ttacttctta    4320
ttcaaatgta ataaaagtat caacaaaaaa ttgttaatat acctctatac tttaacgtca    4380
aggaggagct caccatggct gaaggtgttt tccaaggtgc tatcggtatc gatttaggta    4440
caacctactc ttgtgttgct acttacgaat cctccgttga aattattgcc aacgaacaag    4500
gtaacagagt caccccatct ttcgttgctt tcactccaga agaaagattg attggtgatg    4560
ctgccaagaa ccaagctgct ttgaacccaa gaaacactgt cttcgatgct aagcgtttga    4620
ttggtagaag attcgacgac gaatctgttc aaaaggacat gaagacctgg cctttcaagg    4680
ttatcgacgt cgatggtaac ccagtcatcg aagtccaata cttggaagaa accaagactt    4740
tctccccaca agaaatttcc gctatggttt tgaccaagat gaaggaaatt gctgaagcta    4800
agattggtaa gaaggttgaa aaggccgtca ttactgtccc agcttacttt aacgacgctc    4860
aaagacaagc taccaaggat gccggtgcca tttctggttt gaacgttttg cgtatcatca    4920
acgaacctac tgccgctgct attgcttacg gtctaggtgc tggtaagtcc gaaaaggaaa    4980
gacatgtttt gattttcgat ttgggtggtg gtacttccga tgtttccttg ttgcacattg    5040
ctggtggtgt ttacactgtt aaatctactt ccggtaacac tcacttgggt ggtcaagatt    5100
tcgacaccaa cttgttggaa cacttcaagg ctgaattcaa gaagaagact ggtttggaca    5160
tctccgacga tgccagagct ttgagaagat tgagaactgc tgctgaaaga gctaagagaa    5220
ccttatcttc tgtcactcaa actaccgttg aagttgactc tttgtttgac ggtgaagatt    5280
tcgaatcctc tttgactaga gctagatttg aagacttgaa cgccgcattg ttcaagtcta    5340
ctttggaacc tgttgaacaa gttttgaagg atgctaagat tctctaagtct caaatcgacg    5400 aagttgtctt ggttggtggt tccaccagaa ttccaaaggt ccaaagttg ttgtctgact    5460 tctttgacgg taagcaattg gaaaaatcta ttaacccaga tgaagctgtt gcttacggtg    5520
ctgctgttca aggtgctatc ttgaccggcc aatccacatc tgacgaaacc aaggacttgt    5580
tgttgttaga tgttgctcca ttatctctag gtgttggtat gcaaggtgac atgttcggta    5640
tcgttgttcc aagaaacact actgttccaa ccatcaagag aagaaccttt actacatgtg    5700
ctgacaacca aaccaccgtt caattcccag tctaccaagg tgaacgtgtt aactgtaaag    5760
aaaacacttt gttgggtgaa ttcgacttga agaacatccc aatgatgcca gctggtgaac    5820
cagtcttgga agctatcttc gaagttgatg ctaacggtat cttgaaggtt actgccgtcg    5880
aaaagtctac cggtaagtct tctaacatca ctatctctaa cgctgttggt agattgtctt    5940
ctgaagaaat tgaaaagatg gttaaccaag ctgaagagtt caaggctgcc gatgaagctt    6000
ttgccaagaa gcacgaagct agacaaagat tggaatccta cgttgcctcc atcgaacaaa    6060
```

```
ctgtcactga cccagtcttg tcttctaaat tgaagagagg ttccaagtcc aagattgaag    6120
ctgctttgtc cgatgctttg gctgcttttgc aaatcgaaga cccatctgct gatgaattga    6180
gaaaggctga agttggtttg aagagagttg tcaccaaggc catgtcttct cgttaaggta    6240
cctcatgtaa ttagttatgt cacgcttaca ttcacgccct cccccacat ccgctctaac     6300
cgaaaaggaa ggagttagac aacctgaagt ctaggtccct atttattttt ttatagttat    6360
gttagtatta agaacgttat ttatatttca aattttctt ttttttctgt acagacgcgt     6420
gtacgcatgt aacattatac tgaaaacctt gcttgagaag gttttgggac gctcgaaggc    6480
tttaatttgc cggattagaa ccgccgagc gggtgacagc cctccgaagg aagactctcc     6540
tccgtgcgtc ctcgtcttca ccggtcgcgt tcctgaaacg cagatgtgcc tcgcgccgca    6600
ctgctccgaa caataaagat tctacaatac tagcttttat ggttatgaag aggaaaaatt    6660
ggcagtaacc tggccccaca aaccttcaaa tgaacgaatc aaattaacaa ccataggatg    6720
ataatgcgat tagtttttta gccttatttc tggggtaatt aatcagcgaa gcgatgattt    6780
ttgatctatt aacagatata taaatgcaaa aactgcataa ccactttaac taatactttc    6840
aacattttcg gtttgtatta cttcttattc aaatgtaata aaagtatcaa caaaaaattg    6900
ttaatatacc tctatacttt aacgtcaagg agggatccat gtctattcca gaaactcaaa    6960
aagccattat cttctacgaa tccaacggca agttggagca taaggatatc ccagttccaa    7020
agccaaagcc caacgaattg ttaatcaacg tcaagtactc tggtgtctgc cacaccgatt    7080
tgcacgcttg gcatggtgac tggccattgc caactaagtt accattagtt ggtggtcacg    7140
aaggtgccgg tgtcgttgtc ggcatgggtg aaaacgttaa gggctggaag atcggtgact    7200
acgccggtat caaatggttg aacggttctt gtatggcctg tgaatactgt gaattgggta    7260
acgaatccaa ctgtcctcac gctgacttgt ctggttacac ccacgacggt tctttccaag    7320
aatacgctac cgctgacgct gttcaagccg ctcacattcc tcaaggtact gacttggctg    7380
aagtcgcgcc aatcttgtgt gctggtatca ccgtatacaa ggctttgaag tctgccaact    7440
tgagagcagg ccactgggcg gccatttctg gtgctgctgg tggtctaggt tctttggctg    7500
ttcaatatgc taaggcgatg ggttacagag tcttaggtat tgatggtggt ccaggaaagg    7560
aagaattgtt tacctcgctc ggtggtgaag tattcatcga cttcaccaaa gagaaggaca    7620
ttgttagcgc agtcgttaag gctaccaacg gcggtgccca cggtatcatc aatgtttccg    7680
tttccgaagc cgctatcgaa gcttctacca gatactgtag ggcgaacggt actgttgtct    7740
tggttggttt gccagccggt gcaaagtgct cctctgatgt cttcaaccac gttgtcaagt    7800
ctatctccat tgtcggctct tacgtgggga acagagctga taccagagaa gccttagatt    7860
tctttgccag aggtctagtc aagtctccaa taaaggtagt tggcttatcc agttaccag     7920
aaatttacga aaagatggag aagggccaaa ttgctggtag atacgttgtt gacacttcta    7980
aataagaatt ctcatgtaat tagttatgtc acgcttacat tcacgccctc ccccacatc     8040
cgctctaacc gaaaaggaag gagttagaca acctgaagtc taggtcccta tttatttttt    8100
tatagttatg ttagtattaa gaacgttatt tatatttcaa attttctttt ttttctgta     8160
cagacgcgtg tacgcatgta acattatact gaaaaccttg cttgagaagg ttttgggacg    8220
ctcgaaggct ttaatttgcc ggattagaag ccgccgagcg ggtgacagcc ctccgaagga    8280
agactctcct ccgtgcgtcc tcgtcttcac cggtcgcgtt cctgaaacgc agatgtgcct    8340
cgcgccgcac tgctccgaac aataaagatt ctacaatact agcttttatg gttatgaaga    8400
```

```
ggaaaaattg gcagtaacct ggccccacaa accttcaaat gaacgaatca aattaacaac    8460
cataggatga taatgcgatt agttttttag ccttatttct ggggtaatta atcagcgaag    8520
cgatgatttt tgatctatta acagatatat aaatgcaaaa actgcataac cactttaact    8580
aatactttca acattttcgg tttgtattac ttcttattca aatgtaataa agtatcaac     8640
aaaaaattgt taatatacct ctatacttta acgtcaagga ggcggccgcc atggtgagca    8700
agggcgagga gctgttcacc ggggtggtgc ccatcctggt cgagctggac ggcgacgtaa    8760
acggccacaa gttcagcgtg tccggcgagg gcgagggcga tgccacctac ggcaagctga    8820
cccctgaagtt catctgcacc accggcaagc tgcccgtgcc ctggcccacc ctcgtgacca    8880
ccttcggcta cggcctgcaa tgcttcgccc gctaccccga ccacatgaag ctgcacgact    8940
tcttcaagtc cgccatgccc gaaggctacg tccaggagcg caccatcttc ttcaaggacg    9000
acggcaacta caagacccgc gccgaggtga agttcgaggg cgacaccctg gtgaaccgca    9060
tcgagctgaa gggcatcgac ttcaaggagg acggcaacat cctggggcac aagctggagt    9120
acaactacaa cagccacaac gtctatatca tggccgacaa gcagaagaac ggcatcaagg    9180
tgaacttcaa gatccgccac aacatcgagg acggcagcgt gcagctcgcc gaccactacc    9240
agcagaacac ccccatcggc gacggccccg tgctgctgcc cgacaaccac tacctgagct    9300
accagtccgc cctgagcaaa gaccccaacg agaagcgcga tcacatggtc ctgctggagt    9360
tcgtgaccgc cgccgggatc actctcggca tggacgagct gtacaagtaa taatcgtacg    9420
catcatgtaa ttagttatgt cacgcttaca ttcacgccct ccccccacat ccgctctaac    9480
cgaaaaggaa ggagttagac aacctgaagt ctaggtccct atttattttt ttatagttat    9540
gttagtatta agaacgttat ttatatttca aatttttctt ttttttctgt acagacgcgt    9600
gtacgcatgt aacattatac tgaaaacctt gcttgagaag gttttgggac gctcgaaggc    9660
tttaatttgc atgctagtag ttaggtgccc tggccgttcc cagcattggt ggccgcggcc    9720
gtggccggac cggcgcccgg ggtggcgccc agcaccgact gcaggtcagg cttcatcgcc    9780
tgcagctgcg cgccccagta gggccagtcg tgggtgccgt tggcgtcgaa gttccacacc    9840
gcgttgtggc cgccggcgcc gttgtaggcg tcctggaact tcaggttgga cgtccgcacg    9900
aagccctcga ggaacttggc gggcaggttg tcgccaccga ggtcggacgg cttgccgttg    9960
ccgcagtaca cccagatccg ggtgttgttc gcgaccagct tgccgacctg cagcgacggg   10020
tcgttgcggg cccaggccgg gtcctccttc ggaccccaca tgtcggcggc cttgtagcca   10080
ccggcgtcac ccatggccag cccgatcagc gacgggccca tgccctgcga cgagtccagc   10140
agcgccgaca gcgagccggc gtagacgaac tggtcggggt ggtaggcggc caggatcagc   10200
gccgaggagc cggccatcga caggccgacg acaccgctgc cggtcggctt gacctgcttc   10260
tgcgccgaca ggtactgcgg cagctcgctg gtcaggaagg tctcccactt gtaggtggtg   10320
cagccggcct tgccgcaggc gggcttgtac cagtcggagt agaagctgga ctggccgccg   10380
accggcatgg cgaccgagat gcccgactgg ttgtaccact cgaacgccgg ggtgttgatg   10440
tcccagccgt tgaagtcgtc ttgcgcgcgc atcccgtcga gcaggtacaa cgcgggcgag   10500
ttggccccac cgctttggaa ctggaccttg atgtccgtc catggcggc ggagggaacc     10560
tgcaggtact ccaccggcag accggggcgc gagaaggccc cggcggtcgc cgagcccccg   10620
acggcgccaa tcaggcccga gagcagcgcc gcaccagcgg cccccaccac gagccggcgc   10680
ggcatccccg ccacgcgccc gcgcaatctg tcgcacatgt caaaggaacag aacggtacag   10740
agaagccaca gaatttgagt agaagggacg tcttgaaggg tattgcaatc acagcaggtg   10800
```

```
ttgttgctgc tggcgctgta gtgggagtta accctattgg tgctgctcat gctgctggta   10860
agtgcccagg tatcactcct aaggcttcat tacaatacca accacaccct aaaggtaaag   10920
agcaatgctc tgcctgtgca aacttcatcg caccacattg ttgtaaagtg gttgctggtt   10980
ctgttgttcc agaaggatat tgtatggcct tcatcttgaa gcctgcataa tctagagggc   11040
cgcatcatgt aattagttat gtcacgctta cattcacgcc ctcccccac atccgctcta    11100
accgaaaagg aaggagttag acaacctgaa gtctaggtcc ctatttattt ttttatagtt   11160
atgttagtat taagaacgtt atttatattt caaattttc ttttttttct gtacagacgc    11220
gtgtacgcat gtaacattat actgaaaacc ttgcttgaga aggttttggg acgctcgaag   11280
gctttaattt gcggccctgc attaatgaat cggccaacgc gcggggagag gcggtttgcg   11340
tattgggcgc tcttccgctt cctcgctcac tgactcgctg cgctcggtcg ttcggctgcg   11400
gcgagcggta tcagctcact caaaggcggt aatacggtta tccacagaat cagggataa    11460
cgcaggaaag aacatgtgag caaaaggcca gcaaaagccc aggaaccgta aaaaggccgc   11520
gttgctggcg ttttccata ggctccgccc ccctgacgag catcacaaaa atcgacgctc    11580
aagtcagagg tggcgaaacc cgacaggact ataaagatac caggcgtttc ccctggaag    11640
ctccctcgtg cgctctcctg ttccgaccct gccgcttacc ggatacctgt ccgcctttct   11700
cccttcggga agcgtggcgc tttctcatag ctcacgctgt aggtatctca gttcggtgta   11760
ggtcgttcgc tccaagctgg gctgtgtgca cgaaccccc gttcagcccg accgctgcgc    11820
cttatccggt aactatcgtc ttgagtccaa cccggtaaga cacgacttat cgccactggc   11880
agcagccact ggtaacagga ttagcagagc gaggtatgta ggcggtgcta cagagttctt   11940
gaagtggtgg cctaactacg gctacactag aaggacagta tttggtatct gcgctctgct   12000
gaagccagtt accttcggaa aaagagttgg tagctcttga tccggcaaac aaaccaccgc   12060
tggtagcggt ggtttttttg tttgcaagca gcagattacg cgcagaaaaa aaggatctca   12120
agaagatcct ttgatctttt ctacggggtc tgacgctcag tggaacgaaa actcacgtta   12180
agggattttg gtcatgagat tatcaaaaag gatcttcacc tagatccttt taaattaaaa   12240
atgaagtttt aaatcaatct aaagtatata tgagtaaact tggtctgaca gttaccaatg   12300
cttaatcagt gaggcaccta tctcagcgat ctgtctattt cgttcatcca tagttgcctg   12360
actccccgtc gtgtagataa ctacgatacg ggagcgctta ccatctggcc ccagtgctgc   12420
aatgataccg cgagacccac gctcaccggc tccagattta tcagcaataa accagccagc   12480
cggaagggcc gagcgcagaa gtggtcctgc aactttatcc gcctccatcc agtctattaa   12540
ttgttgccgg gaagctagag taagtagttc gccagttaat agtttgcgca acgttgttgg   12600
cattgctaca gcatcgtgg tgtcactctc gtcgtttggt atggcttcat tcagctccgg    12660
ttcccaacga tcaaggcgag ttacatgatc ccccatgttg tgcaaaaaag cggttagctc   12720
cttcggtcct ccgatcgttg tcagaagtaa gttggccgca gtgttatcac tcatggttat   12780
ggcagcactg cataattctc ttactgtcat gccatccgta agatgctttt ctgtgactgg   12840
tgagtactca accaagtcat tctgagaata gtgtatgcgg cgaccgagtt gctcttgccc   12900
ggcgtcaata cgggataata gtgtatcaca tagcagaact ttaaaagtgc tcatcattgg   12960
aaaacgttct cggggcgaa aactctcaag gatcttaccg ctgttgagat ccagttcgat    13020
gtaacccact cgtgcaccca actgatcttc agcatctttt actttcacca gcgtttctgg   13080
gtgagcaaaa acaggaaggc aaaatgccgc aaaaaaggga ataaggggcga cacggaaatg   13140
```

```
ttgaatactc atactcttcc tttttcaatg ggtaataact gatataatta aattgaagct  13200
ctaatttgtg agtttagtat acatgcattt acttataata cagtttttta gttttgctgg  13260
ccgcatcttc tcaaatatgc ttcccagcct gcttttctgt aacgttcacc ctctacctta  13320
gcatcccttc cctttgcaaa tagtcctctt ccaacaataa taatgtcaga tcctgtagag  13380
accacatcat ccacggttct atactgttga cccaatgcgt ctcccttgtc atctaaaccc  13440
acaccgggtg tcataatcaa ccaatcgtaa ccttcatctc ttccacccat gtctctttga  13500
gcaataaagc cgataacaaa atctttgtcg ctcttcgcaa tgtcaacagt acccttagta  13560
tattctccag tagataggga gcccttgcat gacaattctg ctaacatcaa aaggcctcta  13620
ggttcctttg ttacttcttc tgccgcctgc ttcaaaccgc taacaatacc tgggcccacc  13680
acaccgtgtg cattcgtaat gtctgcccat tctgctattc tgtatacacc cgcagagtac  13740
tgcaatttga ctgtattacc aatgtcagca aattttctgt cttcgaagag taaaaaattg  13800
tacttggcgg ataatgcctt tagcggctta actgtgccct ccatggaaaa atcagtcaag  13860
atatccacat gtgtttttag taaacaaatt ttgggaccta atgcttcaac taactccagt  13920
aattccttgg tggtacgaac atccaatgaa gcacacaagt ttgtttgctt ttcgtgcatg  13980
atattaaata gcttggcagc aacaggacta ggatgagtag cagcacgttc cttatatgta  14040
gctttcgaca tgatttatct tcgtttcctg caggtttttg ttctgtgcag ttgggttaag  14100
aatactgggc aatttcatgt ttcttcaaca ctacatatgc gtatatatac caatctaagt  14160
ctgtgctcct tccttcgttc ttccttctgt tcggagatta ccgaatcaaa aaaatttcaa  14220
agaaaccgaa atcaaaaaaa agaataaaaa aaaaatgatg aattgaattg aaaagctagc  14280
ttatcgatga taagctgtca aagatgagaa ttaattccac ggactataga ctatactaga  14340
tactccgtct actgtacgat acacttccgc tcaggtcctt gtcctttaac gaggccttac  14400
cactcttttg ttactctatt gatccagctc agcaaaggca gtgtgatcta agattctatc  14460
ttcgcgatgt agtaaaacta gctagaccga gaaagagact agaaatgcaa aaggcacttc  14520
tacaatggct gccatcatta ttatccgatg tgacgctgca gcttctcaat gatattcgaa  14580
tacgctttga ggagatacag cctaatatcc gacaaactgt tttacagatt tacgatcgta  14640
cttgttaccc atcattgaat tttgaacatc cgaacctggg agttttccct gaaacagata  14700
gtatatttga acctgtataa taatatatag tctagcgctt tacggaagac aatgtatgta  14760
tttcggttcc tggagaaact attgcatcta ttgcataggt aatcttgcac gtcgcatccc  14820
cggttcattt tctgcgtttc catcttgcac ttcaatagca tatctttgtt aacgaagcat  14880
ctgtgcttca ttttgtagaa caaaaatgca acgcgagagc gctaattttt caaacaaaga  14940
atctgagctg catttttaca gaacagaaat gcaacgcgaa agcgctattt taccaacgaa  15000
gaatctgtgc ttcatttttg taaaacaaaa atgcaacgcg acgagagcgc taatttttca  15060
aacaaagaat ctgagctgca tttttacaga acagaaatgc aacgcgagag cgctatttta  15120
ccaacaaaga atctatactt cttttttgtt ctacaaaaat gcatcccgag agcgctattt  15180
ttctaacaaa gcatcttaga ttactttttt tctcctttgt gcgctctata atgcagtctc  15240
ttgataactt tttgcactgt aggtccgtta aggttagaag aaggctactt tggtgtctat  15300
tttctcttcc ataaaaaaag cctgactcca cttcccgcgt ttactgatta ctagcgaagc  15360
tgcgggtgca ttttttcaag ataaaggcat ccccgattat attctatacc gatgtggatt  15420
gcgcatactt tgtgaacaga aagtgatagc gttgatgatt cttcattggt cagaaaatta  15480
tgaacggttt cttctatttt gtctctatat actacgtata ggaaatgttt acattttcgt  15540
```

```
attgttttcg attcactcta tgaatagttc ttactacaat ttttttgtct aaagagtaat    15600
actagagata aacataaaaa atgtagaggt cgagtttaga tgcaagttca aggagcgaaa    15660
ggtggatggg taggttatat agggatatag cacagagata tatagcaaag agatactttt    15720
gagcaatgtt tgtggaagcg gtattcgcaa tgggaagctc caccccggtt gataatcaga    15780
aaagccccaa aaacaggaag attgtataag caaatatttta aattgtaaac gttaatattt    15840
```

```
tgttaaaatt cgcgttaaat ttttgttaaa tcagctcatt ttttaacgaa tagcccgaaa    15900
tcggcaaaat cccttataaa tcaaaagaat agaccgagat agggttgagt gttgttccag    15960
tttccaacaa gagtccacta ttaaagaacg tggactccaa cgtcaagggg cgaaaaaggg    16020
tctatcaggg cgatggccca ctacgtgaac catcacccta atcaagtttt tggggtcga    16080 ggtgccgtaa agcagtaaat cggaagggta aacggatgcc cccatttaga gcttgacggg    16140
gaaagccggc gaacgtggcg agaaaggaag ggaagaaagc gaaggagcg ggggctaggg    16200 cggtgggaag tgtaggggtc acgctgggcg taaccaccac acccgccgcg cttaatgggg    16260
cgctacaggg cgcgtgggga tgatccacta gt                                  16292
```

<210> SEQ ID NO 3
<211> LENGTH: 16760
<212> TYPE: DNA
<213> ORGANISM: Artificial Sequence
<220> FEATURE:
<223> OTHER INFORMATION: Synthetic Construct

<400> SEQUENCE: 3

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagcttccta ggatgacaga tcgttgtcca ggtagggatg     540
ctccacactt agcagtcatt ggagcaggtc cagctggctt agcagcagca ttagctgctg     600
ctgctagagg tgttcgtgta accttgttgg atgctgaacc agaagcagga ggccaattct     660
atagacagcc agcagcagct ttacgtgcta aaggccaca agcattacac catcagtggc      720
gtacctttgc cagattgaga cacgattagc caggcacat tgcagcaggt agagttagac       780
atgctagaga acaccatgtt tggtttgctg agagagctcc tgatggtgga ttcaccgttc      840
atgctttgac tggtccaggt agaggagatc cagcagaagt gagagcagat gcagtcttgt     900
tggcaactgg tggtcacgag actgtgttgc cattcccagg ttggaccttg ccaggtgttg     960
tcacagctgg aggtgcccaa gccatgttga aggcaggttt agttacatct ggcaacaccg    1020
cagtcgtagc tggtactggt ccattgttgt tgccagtagc tacaggttta gctgctgctg    1080
gtgttgacgt aagagcatta gtcgaaagtg ctgatcctgg tgccttacca agacaggcac    1140
gtgctttggc agctcaacct ggcaagttgg ctgaaggtgc tttgtatgct ggtcaattgt    1200
tgaggcacag agtgcgtgtc ttgactagac acactgtcgt tgaagcacat ggtacagaga    1260
```

```
ggttggaagc agttactgtt gcagccttgg atgcaggtgg acgtactaga cctggcactg     1320
ctagaagaat agcatgtgca actttagctg tgggtcatgg tatgttgcca catacagact     1380
tggcagacgc cttaggctgc cgtttagcag gtccagcagt tcatgcagat gatgaacaaa     1440
gaactgatgt tcctggtgtg tgggcagcag agagtgtac tggcgtaggt ggtgcagctt      1500
tgtctttggc tgagggtcat atcgctggca gaagtgcagc agccagattg ttaggagcac     1560
ctccaggtcc cgacgcatgg ccagaggcag ctagaacaag agcaaggttg agagcttcct    1620
ccgctgtatt ggatgctgtt tacactcctc ctcctggttg gggtgagaga gtcaccgacg    1680
caaccgttgt atgcaggtgt gaagaagtta cagcaggtgc aatccgtgct tctgtgaggg   1740
aattgggagc tggtgacgta cgtactgtaa agttgttgac tagagctggc atgggatggt    1800 gtcaggggaag aatgtgtgct cctgctgtcg ctggattggc aggttgtgct ttcactccta  1860
gtcgtagacc attcgctagg ccagtgcctt tgggagtgtt ggccagagct ggtgaagatg    1920
caggtggcga tggaggcaga gctgaggatc aaggtgaagg agatggacgt gctgctggag    1980
caggaggttg attaattaat catgtaatta gttatgtcac gcttacattc acgccctccc   2040
cccacatccg ctctaaccga aaaggaagga gttagacaac ctgaagtcta ggtccctatt   2100
tattttttta tagttatgtt agtattaaga acgttattta tatttcaaat ttttctttt    2160 tttctgtaca gacgcgtgta cgcatgtaac attatactga aaaccttgct tgagaaggtt  2220
ttgggacgct cgaaggcttt aatttgccgg attagaagcc gccagcgggg tgacagccct   2280
ccgaaggaag actctcctcc gtgcgtcctc gtcttcaccg gtcgcgttcc tgaaacgcag  2340
atgtgcctcg cgccgcactg ctccgaacaa taaagattct acaatactag cttttatggt  2400
tatgaagagg aaaaattggc agtaacctgg ccccacaaac cttcaaatga acgaatcaaa   2460
ttaacaacca taggatgata atgcgattag ttttttagcc ttatttctgg ggtaattaat    2520
cagcgaagcg atgattttg atctattaac agatatataa atgcaaaaac tgcataacca    2580
ctttaactaa tactttcaac attttcggtt tgtattactt cttattcaaa tgtaataaaa   2640
gtatcaacaa aaaattgtta atatacctct atactttaac gtcaaggagg gcgcgccatg   2700
gttcatttag gtccaaagaa accacaggct agaaagggtt ccatggctga tgtgcccaag  2760
gaattgatgg atgaaattca tcagttggaa gatatgttta cagttgacag cgagaccttg    2820
agaaaggttg ttaagcactt tatcgacgaa ttgaataaag gtttgacaaa gaagggaggt   2880
aacattccaa tgattcccgg ttgggtcatg gaattcccaa caggtaaaga atctggtaac   2940
tatttggcca ttgatttggg tggtactaac ttaagagtcg tgttggtcaa gttgagcggt   3000
aaccatacct ttgacaccac tcaatccaag tataaactac cacatgacat gagaaccact   3060
aagcaccaag aggagttatg gtcctttatt gccgactctt tgaaggactt tatggtcgag   3120
caagaattgc taaacaccaa ggacaccta ccattaggtt tcaccttctc gtacccagct    3180
tcccaaaaca agattaacga aggtattttg caaagatgga ccaagggttt cgatattcca    3240
aatgtcgaag gccacgatgt cgtcccattg ctacaaaacg aaatttccaa gagagagttg    3300
cctattgaaa ttgtagcatt gattaatgat actgttggta cttaattgc ctcatactac    3360 actgacccag agactaagat gggtgtgatt tcggtactg tgtcaacgg tgctttctat     3420 gatgttgttt ccgatatcga aaagttggag ggcaaattag cagacgatat tccaagtaac   3480
tctccaatgg ctatcaattg tgaatatggt tccttcgata tgaacattt ggtcttgcca    3540 agaaccaagt acgatgttgc tgtcgacgaa caatctccaa gacctggtca acaagctttt   3600 gaaagagatga cctccggtta ctacttgggt gaattgttgc gtctagtgtt acttgaatta   3660
```

```
aacgagaagg gcttgatgtt gaaggatcaa gatctaagca agttgaaaca accatacatc    3720
atggatacct cctacccagc aagaatcgag gatgatccat ttgaaaactt ggaagatact    3780
gatgacatct tccaaaagga ctttggtgtc aagaccactc tgccagaacg taagttgatt    3840
agaagacttt gtgaattgat cggtaccaga gctgctagat tagctgtttg tggtattgcc    3900
gctatttgcc aaaagagagg ttacaagact ggtcacattg ccgctgacgg ttctgtctat    3960
aacaaatacc caggtttcaa ggaagccgcc gctaagggtt tgagagatat ctatggatgg    4020
actggtgacg caagcaaaga tccaattacg attgttccag ctgaggatgg ttcaggtgca    4080
ggtgctgctg ttattgctgc attgtccgaa aaaagaattg ccgaaggtaa gtctcttggt    4140
atcattggcg cttaagttta aactcatgta attagttatg tcacgcttac attcacgccc    4200 tcccccaca tccgctctaa ccgaaaagga aggagttaga caacctgaag tctaggtccc    4260
tatttatttt tttatagtta tgttagtatt aagaacgtta tttatatttc aaattttttct    4320 ttttttctg tacagacgcg tgtacgcatg taacattata ctgaaaacct tgcttgagaa    4380
ggttttggga cgctcgaagg ctttaatttg ccggattaga agccgccgag cgggtgacag    4440
ccctccgaag gaagactctc ctccgtgcgt cctcgtcttc accggtcgcg ttcctgaaac    4500
gcagatgtgc ctcgcgccgc actgctccga acaataaaga ttctacaata ctagctttta    4560
tggttatgaa gaggaaaaat tggcagtaac ctggccccac aaaccttcaa atgaacgaat    4620
caaattaaca accataggat gataatgcga ttagtttttt agccttattt ctggggtaat    4680
taatcagcga agcgatgatt tttgatctat taacagatat ataaatgcaa aaactgcata    4740
accactttaa ctaatacttt caacattttc ggtttgtatt acttcttatt caaatgtaat    4800
aaaagtatca acaaaaaatt gttaatatac ctctatactt taacgtcaag gaggagctca    4860
ccatggctga aggtgttttc caaggtgcta tcggtatcga tttaggtaca acctactctt    4920
gtgttgctac ttacgaatcc tccgttgaaa ttattgccaa cgaacaaggt aacagagtca    4980
ccccatcttt cgttgctttc actccagaag aaagattgat tggtgatgct gccaagaacc    5040
aagctgcttt gaacccaaga aacactgtct tcgatgctaa gcgtttgatt ggtagaagat    5100
tcgacgacga atctgttcaa aaggacatga agacctggcc tttcaaggtt atcgacgtcg    5160
atggtaaccc agtcatcgaa gtccaatact tggaagaaac caagactttc tccccacaag    5220
aaatttccgc tatggttttg accaagatga aggaaattgc tgaagctaag attggtaaga    5280
aggttgaaaa ggccgtcatt actgtcccag cttactttaa cgacgctcaa agacaagcta    5340
ccaaggatgc cggtgccatt tctggttttga acgttttgcg tatcatcaac gaacctactg    5400
ccgctgctat tgcttacggt ctaggtgctg gtaagtccga aaaggaaaga catgttttga    5460
ttttcgattt gggtggtggt actttcgatg tttccttgtt gcacattgct ggtggtgttt    5520
acactgttaa atctacttcc ggtaacactc acttgggtgg tcaagatttc gacaccaact    5580
tgttggaaca cttcaaggct gaattcaaga agaagactgg tttggacatc tccgacgatg    5640
ccagagcttt gagaagattg agaactgctg ctgaaagagc taagagaacc ttatcttctg    5700
tcactcaaac taccgttgaa gttgactctt tgtttgacgg tgaagatttc gaatcctctt    5760
tgactagagc tagatttgaa gacttgaacg ccgcattgtt caagtctact ttggaacctg    5820
ttgaacaagt tttgaaggat gctaagatct ctaagtctca aatcgacgaa gttgtcttgg    5880
ttggtggttc caccagaatt ccaaaggtcc aaaagttgtt gtctgacttc tttgacggta    5940
agcaattgga aaaatctatt aacccagatg aagctgttgc ttacggtgct gctgttcaag    6000
```

```
gtgctatctt gaccggccaa tccacatctg acgaaaccaa ggacttgttg ttgttagatg    6060
ttgctccatt atctctaggt gttggtatgc aaggtgacat gttcggtatc gttgttccaa    6120
gaaacactac tgttccaacc atcaagagaa gaacctttac tacatgtgct gacaaccaaa    6180
ccaccgttca attcccagtc taccaaggtg aacgtgttaa ctgtaaagaa aacactttgt    6240
tgggtgaatt cgacttgaag aacatcccaa tgatgccagc tggtgaacca gtcttggaag    6300
ctatcttcga agttgatgct aacggtatct tgaaggttac tgccgtcgaa aagtctaccg    6360
gtaagtcttc taacatcact atctctaacg ctgttggtag attgtcttct gaagaaattg    6420
aaaagatggt taaccaagct gaagagttca aggctgccga tgaagctttt gccaagaagc    6480
acgaagctag acaaagattg gaatcctacg ttgcctccat cgaacaaact gtcactgacc    6540
cagtcttgtc ttctaaattg aagagaggtt ccaagtccaa gattgaagct gctttgtccg    6600
atgctttggc tgctttgcaa atcgaagacc catctgctga tgaattgaga aaggctgaag    6660
ttggtttgaa gagagttgtc accaaggcca tgtcttctcg ttaaggtacc tcatgtaatt    6720
agttatgtca cgcttacatt cacgccctcc ccccacatcc gctctaaccg aaaaggaagg    6780
agttagacaa cctgaagtct aggtccctat ttattttttt atagttatgt tagtattaag    6840
aacgttattt atatttcaaa ttttctttt ttttctgtac agacgcgtgt acgcatgtaa    6900
cattatactg aaaaccttgc ttgagaaggt tttgggacgc tcgaaggctt taatttgccg    6960
gattagaagc cgccgagcgg gtgacagccc tccgaaggaa gactctcctc cgtgcgtcct    7020
cgtcttcacc ggtcgcgttc ctgaaacgca gatgtgcctc gcgccgcact gctccgaaca    7080
ataaagattc tacaatacta gcttttatgg ttatgaagag gaaaaattgg cagtaacctg    7140
gccccacaaa ccttcaaatg aacgaatcaa attaacaacc ataggatgat aatgcgatta    7200 gtttttagc cttatttctg gggtaattaa tcagcgaagc gatgattttt gatctattaa    7260
cagatatata aatgcaaaaa ctgcataacc actttaacta atactttcaa cattttcggt    7320
ttgtattact tcttattcaa atgtaataaa agtatcaaca aaaaattgtt aatataccct    7380
tatactttaa cgtcaaggag ggatccatgt ctattccaga aactcaaaaa gccattatct    7440
tctacgaatc caacggcaag ttggagcata aggatatccc agttccaaag ccaaagccca    7500
acgaattgtt aatcaacgtc aagtactctg gtgtctgcca caccgatttg cacgcttggc    7560
atggtgactg gccattgcca actaagttac cattagttgg tggtcacgaa ggtgccggtg    7620
tcgttgtcgg catgggtgaa aacgttaagg gctggaagat cggtgactac gccggtatca    7680
aatggttgaa cggttcttgt atggcctgtg aatactgtga attgggtaac gaatccaact    7740
gtcctcacgc tgacttgtct ggttacaccc acgacggttc tttccaagaa tacgctaccg    7800
ctgacgctgt tcaagccgct cacattcctc aaggtactga cttggctgaa gtcgcgccaa    7860
tcttgtgtgc tggtatcacc gtatacaagg ctttgaagtc tgccaacttg agagcaggcc    7920
actgggcggc catttctggt gctgctggtg gtctaggttc tttggctgtt caatatgcta    7980
aggcgatggg ttacagagtc ttaggtattg atggtggtcc aggaaaggaa gaattgttta    8040
cctcgctcgg tggtgaagta ttcatcgact tcaccaaaga gaaggacatt gttagcgcag    8100
tcgttaaggc taccaacggc ggtgcccacg gtatcatcaa tgtttccgtt tccgaagccg    8160
ctatcgaagc ttctaccaga tactgtaggg cgaacggtac tgttgtcttg gttggtttgc    8220
cagccggtgc aaagtgctcc tctgatgtct tcaaccacgt tgtcaagtct atctccattg    8280
tcggctctta cgtggggaac agagctgata ccagagaagc cttagatttc tttgccagag    8340
gtctagtcaa gtctccaata aaggtagttg gcttatccag tttaccagaa atttacgaaa    8400
```

```
agatggagaa gggccaaatt gctggtagat acgttgttga cacttctaaa taagaattct   8460
catgtaatta gttatgtcac gcttacattc acgccctccc cccacatccg ctctaaccga   8520
aaaggaagga gttagacaac ctgaagtcta ggtccctatt tattttttta tagttatgtt   8580
agtattaaga acgttatttta tatttcaaat ttttcttttt tttctgtaca gacgcgtgta   8640
cgcatgtaac attatactga aaaccttgct tgagaaggtt ttgggacgct cgaaggcttt   8700
aatttgccgg attagaagcc gccgagcggg tgacagccct ccgaaggaag actctcctcc   8760
gtgcgtcctc gtcttcaccg gtcgcgttcc tgaaacgcag atgtgcctcg cgccgcactg   8820
ctccgaacaa taaagattct acaatactag cttttatggt tatgaagagg aaaaattggc   8880
agtaacctgg ccccacaaac cttcaaatga acgaatcaaa ttaacaacca taggatgata   8940
atgcgattag ttttttagcc ttatttctgg ggtaattaat cagcgaagcg atgattttg    9000
atctattaac agatatataa atgcaaaaac tgcataacca ctttaactaa tactttcaac   9060
attttcggtt tgtattactt cttattcaaa tgtaataaaa gtatcaacaa aaaattgtta   9120
atatacctct atactttaac gtcaaggagg cggccgccat ggtgagcaag ggcgaggagc   9180
tgttcaccgg ggtggtgccc atcctggtcg agctggacgg cgacgtaaac ggccacaagt   9240
tcagcgtgtc cggcgagggc gagggcgatg ccacctacgg caagctgacc ctgaagttca   9300
tctgcaccac cggcaagctg cccgtgccct ggcccaccct cgtgaccacc ttcggctacg   9360
gcctgcaatg cttcgcccgc tacccgacc acatgaagct gcacgacttc ttcaagtccg    9420
ccatgcccga aggctacgtc caggagcgca ccatcttctt caaggacgac ggcaactaca   9480
agacccgcgc cgaggtgaag ttcgagggcg acaccctggt gaaccgcatc gagctgaagg   9540
gcatcgactt caaggaggac ggcaacatcc tggggcacaa gctggagtac aactacaaca   9600
gccacaacgt ctatatcatg gccgacaagc agaagaacgg catcaaggtg aacttcaaga   9660
tccgccacaa catcgaggac ggcagcgtgc agctcgccga ccactaccag cagaacaccc   9720
ccatcggcga cggccccgtg ctgctgcccg acaaccacta cctgagctac cagtccgccc   9780
tgagcaaaga ccccaacgag aagcgcgatc acatggtcct gctggagttc gtgaccgccg   9840
ccgggatcac tctcggcatg gacgagctgt acaagtaata atcgtacgca tcatgtaatt   9900
agttatgtca cgcttacatt cacgccctcc ccccacatcc gctctaaccg aaaaggaagg   9960
agttagacaa cctgaagtct aggtccctat ttatttttttt atagttatgt tagtattaag  10020
aacgttatttt atatttcaaa ttttttctttt ttttctgtac agacgcgtgt acgcatgtaa  10080
cattatactg aaaaccttgc ttgagaaggt tttgggacgc tcgaaggctt taatttgcat   10140
gctagtagtt aggtgccctg ccgttccca gcattggtgg ccgcggccgt ggccggaccg   10200
gcgcccgggg tggcgcccag caccgactgc aggtcaggct tcatcgcctg cagctgcgcg  10260
ccccagtagg gccagtcgtg ggtgccgttg gcgtcgaagt tccacaccgc gttgtggccg  10320
ccggcgccgt tgtaggcgtc ctggaacttc aggttggacg tccgcacgaa gccctcgagg  10380
aacttggcgg gcaggttgtc gccaccgagg tcggacggct tgccgttgcc gcagtacacc  10440
cagatccggg tgttgttcgc gaccagcttg ccgacctgca gcgacgggtc gttgcgggcc  10500
caggccgggt cctccttcgg accccacatg tcggcggcct tgtagccacc ggcgtcaccc  10560
atggccagcc cgatcagcga cgggcccatg ccctgcgacg agtccagcag cgccgacagc  10620
gagcggcgt agacgaactg gtcggggtgg taggcggcca ggatcagcgc cgaggagccg   10680
gccatcgaca ggccgacgac accgctgccg gtcggcttga cctgcttctg cgccgacagg  10740
```

```
tactgcggca gctcgctggt caggaaggtc tcccacttgt aggtggtgca gccggccttg    10800
ccgcaggcgg gcttgtacca gtcggagtag aagctggact ggccgccgac cggcatggcg    10860
accgagatgc ccgactggtt gtaccactcg aacgccgggg tgttgatgtc ccagccgttg    10920
aagtcgtctt gcgcgcgcat cccgtcgagc aggtacaacg cgggcgagtt ggccccaccg    10980
ctttggaact ggaccttgat gtcccgtccc atggcggcgg agggaacctg caggtactcc    11040
accggcagac cggggcgcga gaaggccccg gcggtcgccg agcccccgac ggcgccaatc    11100
aggcccgaga gcagcgccgc accagcggcc cccaccacga gccggcgcgg catcccgcc     11160 acggcgccgc gcaatctgtc gacatgtcaa aggaacagaa cggtacagag aagccacaga    11220
atttgagtag aagggacgtc ttgaagggta ttgcaatcac agcaggtgtt gttgctgctg    11280
gcgctgtagt gggagttaac cctattggtg ctgctcatgc tgctggtaag tgcccaggta    11340
tcactcctaa ggcttcatta caataccaac cacaccctaa aggtaaagag caatgctctg    11400
cctgtgcaaa cttcatcgca ccacattgtt gtaaagtggt tgctggttct gttgttccag    11460
aaggatattg tatggccttc atcttgaagc ctgcataatc tagagggccg catcatgtaa    11520
ttagttatgt cacgcttaca ttcacgccct ccccccacat ccgctctaac cgaaaaggaa    11580
ggagttagac aacctgaagt ctaggtccct atttattttt ttatagttat gttagtatta    11640
agaacgttat ttatatttca aattttttctt ttttttctgt acagacgcgt gtacgcatgt    11700
aacattatac tgaaaacctt gcttgagaag gttttgggac gctcgaaggc tttaatttgc    11760
ggccctgcat taatgaatcg gccaacgcgc ggggagaggc ggtttgcgta ttgggcgctc    11820
ttccgcttcc tcgctcactg actcgctgcg ctcggtcgtt cggctgcggc gagcggtatc    11880
agctcactca aaggcggtaa tacggttatc cacagaatca ggggataacg caggaaagaa    11940
catgtgagca aaaggccagc aaaagcccag gaaccgtaaa aaggccgcgt tgctggcgtt    12000
tttccatagg ctccgccccc ctgacgagca tcacaaaaat cgacgctcaa gtcagaggtg    12060
gcgaaacccg acaggactat aaagatacca ggcgtttccc cctggaagct ccctcgtgcg    12120
ctctcctgtt ccgaccctgc cgcttaccgg atacctgtcc gcctttctcc cttcgggaag    12180
cgtggcgctt tctcatagct cacgctgtag gtatctcagt tcggtgtagg tcgttcgctc    12240
caagctgggc tgtgtgcacg aaccccccgt tcagcccgac cgctgcgcct tatccggtaa    12300
ctatcgtctt gagtccaacc cggtaagaca cgacttatcg ccactggcag cagccactgg    12360
taacaggatt agcagagcga ggtatgtagg cggtgctaca gagttcttga agtggtggcc    12420
taactacggc tacactagaa ggacagtatt tggtatctgc gctctgctga gccagttac     12480 cttcggaaaa agagttggta gctcttgatc cggcaaacaa accaccgctg gtagcggtgg    12540
tttttttgtt tgcaagcagc agattacgcg cagaaaaaaa ggatctcaag aagatccttt    12600
gatcttttct acggggtctg acgctcagtg gaacgaaaac tcacgttaag ggattttggt    12660
catgagatta tcaaaaagga tcttcaccta gatccttttta aattaaaaat gaagttttaa    12720
atcaatctaa agtatatatg agtaaacttg gtctgacagt taccaatgct taatcagtga    12780
ggcacctatc tcagcgatct gtctatttcg ttcatccata gttgcctgac tccccgtcgt    12840
gtagataact acgatacggg agcgcttacc atctggcccc agtgctgcaa tgataccgcg    12900
agacccacgc tcaccggctc cagatttatc agcaataaac cagccagccg aagggccga     12960 gcgcagaagt ggtcctgcaa ctttatccgc ctccatccag tctattaatt gttgccggga    13020
agctagagta agtagttcgc cagttaatag tttgcgcaac gttgttggca ttgctacagg    13080
catcgtggtg tcactctcgt cgtttggtat ggcttcattc agctccggtt cccaacgatc    13140
```

```
aaggcgagtt acatgatccc ccatgttgtg caaaaaagcg gttagctcct tcggtcctcc    13200
gatcgttgtc agaagtaagt tggccgcagt gttatcactc atggttatgg cagcactgca    13260
taattctctt actgtcatgc catccgtaag atgcttttct gtgactggtg agtactcaac    13320
caagtcattc tgagaatagt gtatgcggcg accgagttgc tcttgcccgg cgtcaatacg    13380
ggataatagt gtatcacata gcagaacttt aaaagtgctc atcattggaa acgttcttc    13440 ggggcgaaaa ctctcaagga tcttaccgct gttgagatcc agttcgatgt aacccactcg    13500
tgcacccaac tgatcttcag catcttttac tttcaccagc gtttctgggt gagcaaaaac    13560
aggaaggcaa aatgccgcaa aaagggaat aagggcgaca cggaaatgtt gaatactcat    13620
actcttcctt tttcaatggg taataactga tataattaaa ttgaagctct aatttgtgag    13680
tttagtatac atgcatttac ttataataca gttttttagt tttgctggcc gcatcttctc    13740
aaatatgctt cccagcctgc ttttctgtaa cgttcaccct ctaccttagc atcccttccc    13800
tttgcaaata gtcctcttcc aacaataata atgtcagatc ctgtagagac cacatcatcc    13860
acggttctat actgttgacc caatgcgtct cccttgtcat ctaaacccac accgggtgtc    13920
ataatcaacc aatcgtaacc ttcatctctt ccacccatgt ctctttgagc aataaagccg    13980
ataacaaaat ctttgtcgct cttcgcaatg tcaacagtac ccttagtata ttctccagta    14040
gatagggagc ccttgcatga caattctgct aacatcaaaa ggcctctagg ttcctttgtt    14100
acttcttctg ccgcctgctt caaaccgcta acaatacctg ggcccaccac accgtgtgca    14160
ttcgtaatgt ctgcccattc tgctattctg tatacacccg cagagtactg caatttgact    14220
gtattaccaa tgtcagcaaa ttttctgtct tcgaagagta aaaaattgta cttggcggat    14280
aatgccttta gcggcttaac tgtgccctcc atggaaaaat cagtcaagat atccacatgt    14340 gttttagta aacaaatttt gggacctaat gcttcaacta actccagtaa ttccttggtg    14400
gtacgaacat ccaatgaagc acacaagttt gtttgctttt cgtgcatgat attaaatagc    14460
ttggcagcaa caggactagg atgagtagca gcacgttcct tatatgtagc tttcgacatg    14520
atttatcttc gtttcctgca ggttttttgtt ctgtgcagtt gggttaagaa tactgggcaa    14580
tttcatgttt cttcaacact acatatgcgt atatatacca atctaagtct gtgctccttc    14640
cttcgttctt ccttctgttc ggagattacc gaatcaaaaa aatttcaaag aaaccgaaat    14700
caaaaaaaag aataaaaaaa aaatgatgaa ttgaattgaa aagctagctt atcgatgata    14760
agctgtcaaa gatgagaatt aattccacgg actatagact atactagata ctccgtctac    14820
tgtacgatac acttccgctc aggtccttgt cctttaacga ggccttacca ctcttttgtt    14880
actctattga tccagctcag caaaggcagt gtgatctaag attctatctt cgcgatgtag    14940
taaaactagc tagaccgaga aagagactag aaatgcaaaa ggcacttcta caatggctgc    15000
catcattatt atccgatgtg acgctgcagc ttctcaatga tattcgaata cgctttgagg    15060
agatacagcc taatatccga caaactgttt tacagattta cgatcgtact tgttacccat    15120
cattgaattt tgaacatccg aacctgggag ttttccctga aacagatagt atatttgaac    15180
ctgtataata atatatagtc tagcgcttta cggaagacaa tgtatgtatt tcggttcctg    15240
gagaaactat tgcatctatt gcataggtaa tcttgcacgt cgcatccccg gttcattttc    15300
tgcgtttcca tcttgcactt caatagcata tcttttgttaa cgaagcatct gtgcttcatt    15360
ttgtagaaca aaaatgcaac gcgagagcgc taatttttca aacaaagaat ctgagctgca    15420
tttttacaga acagaaatgc aacgcgaaag cgctatttta ccaacgaaga atctgtgctt    15480
```

-continued

| | |
|---|---|
| cattttttgta aaacaaaaat gcaacgcgac gagagcgcta attttttcaaa caaagaatct | 15540 |
| gagctgcatt tttacagaac agaaatgcaa cgcgagagcg ctattttacc aacaaagaat | 15600 |
| ctatacttct tttttgttct acaaaaatgc atcccgagag cgctatttt ctaacaaagc | 15660 |
| atcttagatt actttttttc tcctttgtgc gctctataat gcagtctctt gataactttt | 15720 |
| tgcactgtag gtccgttaag gttagaagaa ggctactttg gtgtctattt tctcttccat | 15780 |
| aaaaaaagcc tgactccact tcccgcgttt actgattact agcgaagctg cgggtgcatt | 15840 |
| ttttcaagat aaaggcatcc ccgattatat tctataccga tgtggattgc gcatactttg | 15900 |
| tgaacagaaa gtgatagcgt tgatgattct tcattggtca gaaaattatg aacggtttct | 15960 |
| tctattttgt ctctatatac tacgtatagg aaatgtttac atttttcgtat tgttttcgat | 16020 |
| tcactctatg aatagttctt actacaattt ttttgtctaa agagtaatac tagagataaa | 16080 |
| cataaaaaat gtagaggtcg agtttagatg caagttcaag gagcgaaagg tggatgggta | 16140 |
| ggttatatag ggatatagca cagagatata tagcaaagag atactttga gcaatgtttg | 16200 |
| tggaagcggt attcgcaatg ggaagctcca ccccggttga taatcagaaa agccccaaaa | 16260 |
| acaggaagat tgtataagca aatatttaaa ttgtaaacgt taatattttg ttaaaattcg | 16320 |
| cgttaaattt ttgttaaatc agctcatttt ttaacgaata gcccgaaatc ggcaaaatcc | 16380 |
| cttataaatc aaaagaatag accgagatag ggttgagtgt tgttccagtt ccaacaaga | 16440 |
| gtccactatt aaagaacgtg gactccaacg tcaaagggcg aaaagggtc tatcagggcg | 16500 |
| atggcccact acgtgaacca tcaccctaat caagttttttt ggggtcgagg tgccgtaaag | 16560 |
| cagtaaatcg gaagggtaaa cggatgcccc catttagagc ttgacgggga aagccggcga | 16620 |
| acgtggcgag aaaggaaggg aagaaagcga aggagcggg ggctagggcg gtgggaagtg | 16680 |
| tagggggtcac gctgggcgta accaccacac ccgccgcgct taatgggggcg ctacagggcg | 16740 |
| cgtgggggatg atccactagt | 16760 |

<210> SEQ ID NO 4
<211> LENGTH: 1470
<212> TYPE: DNA
<213> ORGANISM: Saccharomyces cerevisiae

<400> SEQUENCE: 4

| | |
|---|---|
| gagctcatgg ttcatttagg tccaaagaaa ccacaggcta gaaagggttc catggctgat | 60 |
| gtgcccaagg aattgatgga tgaaattcat cagttggaag atatgtttac agttgacagc | 120 |
| gagaccttga gaaaggttgt taagcacttt atcgacgaat tgaataaagg tttgacaaag | 180 |
| aagggaggta acattccaat gattcccggt tgggtcatgg aattcccaac aggtaaagaa | 240 |
| tctggtaact atttggccat tgattgggt ggtactaact taagagtcgt gttggtcaag | 300 |
| ttgagcggta accatacctt tgacaccact caatccaagt ataaactacc acatgacatg | 360 |
| agaaccacta gcaccaaga ggagttatgg tcctttattg ccgactcttt gaaggacttt | 420 |
| atggtcgagc aagaattgct aaacaccaag gacaccttac cattaggttt caccttctcg | 480 |
| tacccagctt cccaaaacaa gattaacgaa ggtatttttgc aaagatggac caagggtttc | 540 |
| gatattccaa atgtcgaagg ccacgatgtc gtcccattgc tacaaaacga aatttccaag | 600 |
| agagagttgc ctattgaaat tgtagcgttg attaatgata ctgttggtac tttaattgcc | 660 |
| tcatactaca ctgacccaga gactaagatg ggtgtgatt tcggtactgg tgtcaacggt | 720 |
| gctttctatg atgttgtttc cgatatcgaa aagttggagg gcaaattagc agacgatatt | 780 |
| ccaagtaact ctccaatggc tatcaattgt gaatatggtt ccttcgataa tgaacatttg | 840 |

```
gtcttgccaa gaaccaagta cgatgttgct gtcgacgaac aatctccaag acctggtcaa    900
caagcttttg aaaagatgac ctccggttac tacttgggtg aattgttgcg tctagtgtta    960
cttgaattaa acgagaaggg cttgatgttg aaggatcaag atctaagcaa gttgaaacaa   1020
ccatacatca tggatacctc ctacccagca agaatcgagg atgatccatt tgttttcttg   1080
gaagatactg atgacatctt ccaaaaggac tttggtgtca agaccactct gccagaacgt   1140
aagttgatta gaagactttg tgaattgact ggtaccagag ctgctagatt agctgtttgt   1200
ggtattgccg ctatttgcca aagagaggt tacaagactg gtcacattgc cgctgacggt    1260
tctgtctata acaaataccc aggtttcaag gaagccgccg ctaagggttt gagagatatc   1320
tatggatgga ctggtgacgc aagcaaagat ccaattacga ttgttccagc tgaggatggt   1380
tcaggtgcag gtgctgctgt tattgctgca ttgtccgaaa aagaattgc cgaaggtaag    1440 tctcttggta tcattggcgc ttaactcgag                                      1470
```

<210> SEQ ID NO 5
<211> LENGTH: 1854
<212> TYPE: DNA
<213> ORGANISM: Saccharomyces cerevisiae

<400> SEQUENCE: 5

```
ggtaccatgg ctgaaggtgt tttccaaggt gctatcggta tcgatttagg tacaacctac     60
tcttgtgttg ctacttacga atcctccgtt gaaattattg ccaacgaaca aggtaacaga    120
gtcaccccat ctttcgttgc tttcactcca gaagaaagat tgattggtga tgctgccaag    180
aaccaagctg ctttgaaccc aagaaacact gtcttcgatg ctaagcgttt gattggtaga    240
agattcgacg acgaatctgt tcaaaaggac atgaagacct ggcctttcaa ggttatcgac    300
gtcgatggta acccagtcat cgaagtccaa tacttggaag aaaccaagac tttctcccca    360
caagaaattt ccgctatggt tttgaccaag atgaaggaaa ttgctgaagc taagattggt    420
aagaaggttg aaaaggccgt cattactgtc ccagcttact taacgacgc tcaaagacaa     480 gctaccaagg atgccggtgc catttctggt ttgaacgttt gcgtatcat caacgaacct     540 actgccgctg ctattgctta cggtctaggt gctggtaagt ccgaaaagga agacatgtt     600 ttgattttcg atttgggtgg tggtactttc gatgtttcct tgttgcacat tgctggtggt    660
gtttacactg ttaaatctac ttccggtaac actcacttgg gtggtcaaga tttcgacacc    720
aacttgttgg aacacttcaa ggctgaattc aagaagaaga ctggtttgga catctccgac    780
gatgccagag ctttgagaag attgagaact gctgctgaaa gagctaagag aaccttatct    840
tctgtcactc aaactaccgt tgaagttgac tcttgttg acggtgaaga tttcgaatcc      900 tcttgacta gagctagatt tgaagacttg aacgccgcat tgttcaagtc tacttggaa      960 cctgttgaac aagttttgaa ggatgctaag atctctaagt ctcaaatcga cgaagttgtc   1020
ttggttggtg gttccaccag aattccaaag gtccaaaagt gttgtctga cttcttgac    1080 ggtaagcaat tggaaaaatc tattaaccca gatgaagctg ttgcttacgg tgctgctgtt   1140
caaggtgcta tcttgaccgg ccaatccaca tctgacgaaa ccaaggactt gttgttgtta   1200
gatgttgctc cattatctct aggtgttggt atgcaaggtc acatgttcgg tatcgttgtt   1260
ccaagaaaca ctactgttcc aaccatcaag agaagaacct tactacatg tgctgacaac    1320 caaaccaccg ttcaattccc agtctaccaa ggtgaacgtg ttaactgtaa agaaaacact   1380
ttgttgggtg aattcgactt gaagaacatc ccaatgatgc cagctggtga accagtcttg   1440
```

-continued

```
gaagctatct tcgaagttga tgctaacggt atcttgaagg ttactgccgt cgaaaagtct   1500
accggtaagt cttctaacat cactatctct aacgctgttg gtagattgtc ttctgaagaa   1560
attgaaaaga tggttaacca agctgaagag ttcaaggctg ccgatgaagc ttttgccaag   1620
aagcacgaag ctagacaaag attggaatcc tacgttgcct ccatcgaaca aactgtcact   1680
gacccagtct tgtcttctaa attgaagaga ggttccaagt ccaagattga agctgctttg   1740
tccgatgctt tggctgcttt gcaaatcgaa gacccatctg ctgatgaatt gagaaaggct   1800
gaagttggtt tgaagagagt tgtcaccaag gccatgtctt ctcgttaact cgag         1854
```

<210> SEQ ID NO 6
<211> LENGTH: 1059
<212> TYPE: DNA
<213> ORGANISM: Saccharomyces cerevisiae

<400> SEQUENCE: 6

```
ggtaccatgt ctattccaga aactcaaaaa gccattatct tctacgaatc caacggcaag     60
ttggagcata aggatatccc agttccaaag ccaaagccca acgaattgtt aatcaacgtc    120
aagtactctg gtgtctgcca caccgatttg cacgcttggc atggtgactg gccattgcca    180
actaagttac cattagttgg tggtcacgaa ggtgccggtg tcgttgtcgg catgggtgaa    240
aacgttaagg gctggaagat cggtgactac gccggtatca aatggttgaa cggttcttgt    300
atggcctgtg aatactgtga attgggtaac gaatccaact gtcctcacgc tgacttgtca    360
ggttacaccc acgacggttc tttccaagaa tacgctaccg ctgacgctgt tcaagccgct    420
cacattcctc aaggtactga cttggctgaa gtcgcgccaa tcttgtgtgc tggtatcacc    480
gtatacaagg ctttgaagtc tgccaacttg agagcaggcc actgggcggc catttctggt    540
gctgctggtg gtctaggttc tttggctgtt caatatgcta aggcgatggg ttacagagtc    600
ttaggtattg atggtggtcc aggaaaggaa gaattgttta cctcgctcgg tggtgaagta    660
ttcatcgact tcaccaaaga gaaggacatt gttagcgcag tcgttaaggc taccaacggc    720
ggtgcccacg gtatcatcaa tgtttccgtt tccgaagccg ctatcgaagc ttctaccaga    780
tactgtaggg cgaacggtac tgttgtcttg gttggtttgc cagccggtgc aaagtgctcc    840
tctgatgtct tcaaccacgt tgtcaagtct atctccattg tcggctctta cgtggggaac    900
agagctgata ccagagaagc cttagatttc tttgccagag gtctagtcaa gtctccaata    960
aaggtagttg gcttatccag tttaccagaa atttacgaaa agatggagaa gggccaaatt   1020
gctggtagat acgttgttga cacttctaaa taactcgag                          1059
```

<210> SEQ ID NO 7
<211> LENGTH: 1097
<212> TYPE: DNA
<213> ORGANISM: Mycobacterium avium subsp. paratuberculosis MAP4

<400> SEQUENCE: 7

```
aagcttctgc agcggccgct actagtagtt aggtgccctg gccgttccca gcattggtgg     60
ccgcggccgt ggccggaccg gcgcccgggg tggcgcccag caccgactgc aggtcaggct    120
tcatcgcctg cagctgcgcg ccccagtagg gccagtcgtg ggtgccgttg gcgtcgaagt    180
tccacaccgc gttgtggccg ccggcgccgt tgtaggcgtc ctggaacttc aggttggacg    240
tccgcacgaa gccctcgagg aacttggcgg gcaggttgtc gccaccgagg tcggacggct    300
tgccgttgcc gcagtacacc cagatccggg tgttgttcgc gaccagcttg ccgacctgca    360
gcgacgggtc gttgcgggcc caggccgggt cctccttcgg accccacatg tcggcggcct    420
```

| | |
|---|---|
| tgtagccacc ggcgtcaccc atggccagcc cgatcagcga cgggcccatg ccctgcgacg | 480 |
| agtccagcag cgccgacagc gagccggcgt agacgaactg gtcggggtgg taggcggcca | 540 |
| ggatcagcgc cgaggagccg gccatcgaca ggccgacgac accgctgccg gtcggcttga | 600 |
| cctgcttctg cgccgacagg tactgcggca gctcgctggt caggaaggtc tcccacttgt | 660 |
| aggtggtgca gccggccttg ccgcaggcgg gcttgtacca gtcggagtag aagctggact | 720 |
| ggccgccgac cggcatggcg accgagatgc ccgactggtt gtaccactcg aacgccgggg | 780 |
| tgttgatgtc ccagccgttg aagtcgtctt gcgcgcgcat cccgtcgagc aggtacaacg | 840 |
| cgggcgagtt ggccccaccg ctttggaact ggaccttgat gtcccgtccc atggcggcgg | 900 |
| agggaacctg caggtactcc accggcagac cggggcgcga aaggccccg gcggtcgccg | 960 |
| agcccccgac ggcgccaatc aggcccgaga gcagcgccgc accagcggcc cccaccacga | 1020 |
| gccggcgcgg catccccgcc acggcgccgc gcaatctgtc gacaagcgtc atctagaagc | 1080 |
| ggccgcgaat tcggatc | 1097 |

<210> SEQ ID NO 8
<211> LENGTH: 2130
<212> TYPE: DNA
<213> ORGANISM: Homo sapiens

<400> SEQUENCE: 8

| | |
|---|---|
| agatctaaag aggagaaaat gcgtctggcc gttggtgccc tgctggtgtg cgcggtgctg | 60 |
| ggcctgtgcc tggccgtccc agataaaacc gttcgctggt gcgcagtcag tgagcatgaa | 120 |
| gcgacgaagt gccaatctt ccgcgatcac atgaaaagcg taattccgag cgatggtccg | 180 |
| agtgtagctt gtgttaagaa agcaagctat ctggactgta tccgcgcaat tgcagcgaac | 240 |
| gaagctgatg cagttaccct ggacgcaggt ctggtttacg acgcgtacct ggctcctaac | 300 |
| aatctgaaac cggttgtagc ggagttctat ggtagtaaag aagacccgca aactttctat | 360 |
| tatgcagtgg ccgtggtaaa aaggactct ggttttcaga tgaaccagct gcgtgggaag | 420 |
| aaaagttgtc atacgggcct ggggcgttct gcggttgga acattccaat ggggctgctg | 480 |
| tattgcgatc tgccggaacc acgcaagccg ctggagaaag ctgtagcgaa cttcttcagt | 540 |
| ggttcttgtg cgccttgcgc cgatggtact gattttccgc agctgtgtca gctgtgtccg | 600 |
| ggctgcggtt gttctaccct gaatcagtac tttggctata gtggggcgtt taaatgcctg | 660 |
| aaagatgggg cgggtgacgt ggcgttcgtc aaacattcta cgattttcga aacctggcg | 720 |
| aacaaagcag atcgtgacca atatgaactg ctgtgtctgg acaacactcg caagccagtc | 780 |
| gatgaatata agattgtca tctggcacaa gtgcctagtc atactgtggt cgcgcgtagc | 840 |
| attggtggta aggaggacct gatttgggaa ctgctgaacc aagctcagga gcatttcggc | 900 |
| aaagataaaa gcaaagaatt tcagctgttt tctagcccgc acggcaaaga cctgctgttt | 960 |
| aaagacagcg cccacggctt tctgaaagtg cctccacgca tggatgccaa atgtatctg | 1020 |
| ggttatgaat atgttacggc aattcgcaat ctgcgtgaag cacgtgccc ggaagctccg | 1080 |
| actgacgagt gcaaaccagt aaagtggtgt gccctgtctc atcatgagcg cctgaaatgt | 1140 |
| gatgaatgga gtgtgaactc tgttggcaaa attgagtgcg ttagtgctga accaccgag | 1200 |
| gactgtatcg caaagatcat gaacggcgaa gcagatgcta tgtctctgga tggcggtttt | 1260 |
| gtgtatatcg caggtaaatg cggcctggtc ccagttctgg ctgaaaatta taacaaaagt | 1320 |
| gataactgtg aggatactcc aggggcgggc tattttgcgg tcgctgtcgt caagaaatct | 1380 |

```
gcgagcgatc tgacatggga taacctgaaa gggaagaaat cttgccatac cgcggttggc    1440
cgcaccgctg gtggaacat cccgatgggc ctgctgtata acaaaatcaa tcattgccgt    1500
tttgacgagt tcttcagtga ggggtgtgcg cctggtagta agaaagatag cagcctgtgc    1560
aaactgtgca tgggcagcgg cctgaatctg tgcgaaccta acaataaaga gggttactac    1620
ggctacaccg gcgcgtttcg ctgcctggtt gagaaaggtg atgttgcgtt tgtaaagcac    1680
caaacagtac cgcagaatac gggtgggaag aatccggacc cgtgggccaa gaatctgaat    1740
gaaaaggatt acgaactgct gtgcctggat gggacccgca agccggttga agaatacgcg    1800
aattgtcacc tggcccgcgc cccgaatcac gccgtggtga cgcgcaaaga taaagaggcc    1860
tgcgtccaca aaatcctgcg tcagcagcag cacctgttcg gcagcaatgt gacagattgt    1920
agcggtaatt tctgtctgtt ccgtagcgaa accaaggacc tgctgttccg tgacgacacc    1980
gtgtgtctgg ccaaactgca cgaccgtaat acctacgaga atacctggg cgaggagtac    2040 gtgaaagccg tgggcaatct gcgtaagtgt agcacaagca gcctgctgga agcctgcaca    2100
tttcgtcgtc cgtaaggatc ctcagaattc                                     2130

<210> SEQ ID NO 9
<211> LENGTH: 1025
<212> TYPE: DNA
<213> ORGANISM: Fragaria x ananassa

<400> SEQUENCE: 9
cctaggatgg aggtcgaaag agtccaagac atttcatctt cttctctact aacagaagca      60
atcccgttgg agttcatcag atcagagaaa gaacaaccag cgatcacaac attccgaggt    120
ccaacgccgg cgattcccgt cgtcgatcta agcgatcccg acgaagaaag cgtgaggcgc    180
gcggtggtga aagcgagtga agaatggggg ctattccaag tggttaacca cgggattccg    240
acggagctga tacgcgtttt acaagacgtc ggaagaaaat tcttcgagct tccttcgtcg    300
gagaaagaat ccgtcgctaa accggaagat tcgaaagaca ttgaaggata cggaacaaag    360
cttcagaaag atccagaagg taaaaaagct tgggtcgatc atctcttcca tcgaatctgg    420
ccaccgtcat gcgtcaatta cagattctgg cctaagaatc cacctgaata cagggaggtg    480
aatgaagagt atgcagtgca tgtgaagaag ctatcggaga cgttattagg gattctctcg    540
gatggattag ggttaaagcg tgatgcgttg aaagaaggtc tcggcggaga gatggcggag    600
tatatgatga agattaacta ttatccgccg tgtcctcggc cggatttagc tttaggtgta    660
ccggctcata cagatctcag tggaatcact cttcttgttc ctaacgaagt tcctggactt    720
caagttttca aagatgatca ctggttcgat gcagagtata ttccctccgc cgtcattgtt    780
cacatcggcg atcagattct gaggttgagt aatgggaggt ataaaaatgt gttgcatagg    840
acgacggtgg ataaagagaa gacgaggatg tcgtggccgg ttttcttgga gcctccccgt    900
gaaaagattg ttggaccttt accggaacta accggagatg ataatcctcc aaagtttaaa    960
ccgtttgctt tcaaggatta cagttaccgc aagctcaata aacttcctct ggattgatta   1020
attaa                                                                1025

<210> SEQ ID NO 10
<211> LENGTH: 327
<212> TYPE: DNA
<213> ORGANISM: Acidithiobacillus ferrivorans

<400> SEQUENCE: 10
gtcgacatgt caaggaaca gaacggtaca gagaagccac agaatttgag tagaagggac      60
```

```
gtcttgaagg gtattgcaat cacagcaggt gttgttgctg ctggcgctgt agtgggagtt      120
aaccctattg gtgctgctca tgctgctggt aagtgcccag gtatcactcc taaggcttca      180
ttacaatacc aaccacaccc taaaggtaaa gagcaatgct ctgcctgtgc aaacttcatc      240
gcaccacatt gttgtaaagt ggttgctggt tctgttgttc cagaaggata ttgtatggcc      300
ttcatcttga agcctgcata atctaga                                          327
```

<210> SEQ ID NO 11
<211> LENGTH: 1493
<212> TYPE: DNA
<213> ORGANISM: Streptomyces zinciresistens

<400> SEQUENCE: 11

```
cctaggatga cagatcgttg tccaggtagg gatgctccac acttagcagt cattggagca       60
ggtccagctg gcttagcagc agcattagct gctgctgcta gaggtgttcg tgtaaccttg      120
ttggatgctg aaccagaagc aggaggccaa ttctatagac agccagcagc agctttacgt      180
gctagaaggc cacaagcatt acaccatcag tggcgtacct ttgccagatt gagacacgga      240
ttagccaggc acattgcagc aggtagagtt agacatgcta gagaacacca tgtttggttt      300
gctgagagag ctcctgatgg tggattcacc gttcatgctt tgactggtcc aggtagagga      360
gatccagcag aagtgagagc agatgcagtc ttgttggcaa ctggtggtca cgagactgtg      420
ttgccattcc caggttggac cttgccaggt gttgtcacag ctggaggtgc ccaagccatg      480
ttgaaggcag gtttagttac atctggcaac accgcagtcg tagctggtac tggtccattg      540
ttgttgccag tagctacagg tttagctgct gctggtgttg acgtaagagc attagtcgaa      600
agtgctgatc ctggtgcctt accaagacag gcacgtgctt tggcagctca acctggcaag      660
ttggctgaag gtgctttgta tgctggtcaa ttgttgaggc acagagtgcg tgtcttgact      720
agacacactg tcgttgaagc acatggtaca gagaggttgg aagcagttac tgttgcagcc      780
ttggatgcag gtggacgtac tagacctggc actgctagaa gaatagcatg tgcaacttta      840
gctgtgggtc atggtatgtt gccacataca gacttggcag acgccttagg ctgccgttta      900
gcaggtccag cagttcatgc agatgatgaa caaagaactg atgttcctgg tgtgtgggca      960
gcaggagagt gtactggcgt aggtggtgca gctttgtctt tggctgaggg tcatatcgct     1020
ggcagaagtg cagcagccag attgttagga gcacctccag gtcccgacgc atggccagag     1080
gcagctagaa caagagcaag gttgagagct ttctccgctg tattggatgc tgtttacact     1140
cctcctcctg gttggggtga gagagtcacc gacgcaaccg ttgtatgcag gtgtgaagaa     1200
gttacagcag gtgcaatccg tgcttctgtg agggaattgg gagctggtga cgtacgtact     1260
gtaaagttgt tgactagagc tggcatggga tggtgtcagg gaagaatgtg tgctcctgct     1320
gtcgctggat tggcaggttg tgctttcact cctagtcgta gaccattcgc taggccagtg     1380
cctttgggag tgttggccag agctggtgaa gatgcaggtg gcgatggagg cagagctgag     1440
gatcaaggtg aaggagatgg acgtgctgct ggagcaggag gttgattaat taa           1493
```

<210> SEQ ID NO 12
<211> LENGTH: 890
<212> TYPE: DNA
<213> ORGANISM: Artificial Sequence
<220> FEATURE:
<223> OTHER INFORMATION: Synthetic Construct

<400> SEQUENCE: 12

-continued

| | | | | | |
|---|---|---|---|---|---|
| ggattcaaag | aggagaaata | ctagatggtg | agcaagggcg | aggagctgtt | caccggggtg | 60
| gtgcccatcc | tggtcgagct | ggacggcgac | gtaaacggcc | acaagttcag | cgtgtccggc | 120
| gagggcgagg | gcgatgccac | ctacggcaag | ctgaccctga | agttcatctg | caccaccggc | 180
| aagctgcccg | tgccctggcc | caccctcgtg | accaccttcg | gctacggcct | gcaatgcttc | 240
| gcccgctacc | ccgaccacat | gaagctgcac | gacttcttca | agtccgccat | gcccgaaggc | 300
| tacgtccagg | agcgcaccat | cttcttcaag | gacgacggca | actacaagac | ccgcgccgag | 360
| gtgaagttcg | agggcgacac | cctggtgaac | cgcatcgagc | tgaagggcat | cgacttcaag | 420
| gaggacggca | acatcctggg | gcacaagctg | gagtacaact | acaacagcca | caacgtctat | 480
| atcatggccg | acaagcagaa | gaacggcatc | aaggtgaact | tcaagatccg | ccacaacatc | 540
| gaggacggca | gcgtgcagct | cgccgaccac | taccagcaga | acaccccccat | cggcgacggc | 600
| cccgtgctgc | tgcccgacaa | ccactacctg | agctaccagt | ccgccctgag | caaagacccc | 660
| aacgagaagc | gcgatcacat | ggtcctgctg | gagttcgtga | ccgccgccgg | gatcactctc | 720
| ggcatggacg | agctgtacaa | gtaataatac | tagagccagg | catcaaataa | aacgaaaggc | 780
| tcagtcgaaa | gactgggcct | ttcgttttat | ctgttgtttg | tcggtgaacg | ctctctacta | 840
| gagtcacact | ggctcacctt | cgggtgggcc | tttctgcgtt | tataaagctt | | 890